United States Patent
Fusil et al.

(10) Patent No.: US 11,623,950 B2
(45) Date of Patent: Apr. 11, 2023

(54) LENTIVIRAL VECTOR EXPRESSING MEMBRANE-ANCHORED OR SECRETED ANTIBODY

(71) Applicants: INSTITUT NATIONAL DE LA SANTE ET DE LA RECHERCHE MEDICALE (INSERM), Paris (FR); UNIVERSITÉ CLAUDE BERNARD LYON 1, Villeurbanne (FR); CENTRE NATIONAL DE LA RECHERCHE SCIENTIFIQUE, Paris (FR); ECOLE NORMALE SUPERIEURE DE LYON, Lyons (FR)

(72) Inventors: Floriane Fusil, Lyons (FR); Els Verhoeyen, Nice (FR); Thierry Defrance, Lyons (FR); François-Loïc Cosset, Lyons (FR)

(73) Assignees: INSTITUT NATIONAL DE LA SANTE ET DE LA RECHERCHE MEDICALE (INSERM), Paris (FR); UNIVERSITÉ CLAUDE BERNARD LYON 1, Villeurbanne (FR); CENTRE NATIONAL DE LA RECHERCHE SCIENTIFIQUE, Paris (FR); ECOLE NORMALE SUPERIEURE DE LYON, Lyons (FR)

( * ) Notice: Subject to any disclaimer, the term of this patent is extended or adjusted under 35 U.S.C. 154(b) by 539 days.

(21) Appl. No.: 15/742,909

(22) PCT Filed: Jul. 8, 2016

(86) PCT No.: PCT/EP2016/066349
§ 371 (c)(1),
(2) Date: Jan. 9, 2018

(87) PCT Pub. No.: WO2017/005923
PCT Pub. Date: Jan. 12, 2017

(65) Prior Publication Data
US 2018/0371064 A1    Dec. 27, 2018

(30) Foreign Application Priority Data
Jul. 9, 2015 (EP) .................................. 15306132

(51) Int. Cl.
*C07K 16/00* (2006.01)
*C07K 16/46* (2006.01)
(Continued)

(52) U.S. Cl.
CPC ............ *C07K 16/109* (2013.01); *A61K 39/29* (2013.01); *A61P 31/00* (2018.01); *A61P 35/00* (2018.01);
(Continued)

(58) Field of Classification Search
None
See application file for complete search history.

(56) References Cited

U.S. PATENT DOCUMENTS 7,732,195 B2 * 6/2010 Akamatsu ............ C07K 16/244
435/320.1
7,741,077 B2 * 6/2010 Grawunder ............ A61P 37/04
435/69.6
(Continued)

FOREIGN PATENT DOCUMENTS

WO    2007/131774 A1    11/2007
WO    2009/059235 A2    5/2009

OTHER PUBLICATIONS

Martensson et al., The pre-B-cell receptor. Current Opinion in Immunology vol. 19, Issue 2, Apr. 2007, pp. 137-142. (Year: 2007).*
(Continued)

*Primary Examiner* — Arthur S Leonard
(74) *Attorney, Agent, or Firm* — WCF IP

(57) ABSTRACT

The invention concerns a multicistronic nucleic acid, in particular an isolated multicistronic nucleic acid, comprising: A) a sequence comprising successively: A1) a sequence
(Continued)

encoding the light chain variable domain of an antibody of interest, fused in the frame with A2) a sequence encoding the constant region of the light chain of an immunoglobulin Ig; and B) a sequence comprising successively: B1) a sequence encoding the heavy chain variable domain of said antibody of interest, fused in the frame with B2) a sequence encoding the constant regions of the heavy chain of an immunoglobulin Ig' in secretory form; B3) an intronic sequence of the gene of the heavy chain of said immunoglobulin Ig', said intronic sequence comprising an internal 5' splice site enabling the splicing of said intronic sequence B3) and a secretory-specific poly(A) (p AS) signal from the 3' terminal exon of said gene; B4) a sequence, in frame with sequence B1), encoding the transmembrane and cytoplasmic domains M1 and M2 of the immunoglobulin Ig' BCR, wherein said sequence B4) comprises, between the coding sequences of the M1 and M2 domains, an intronic sequence containing a splice site enabling the splicing of said intronic sequence between the M1 and M2 domains coding sequences; and B5) a membrane-anchored specific poly(A) signal (p AM), after the stop codon of the M2 domain, wherein the multicistronic nucleic acid enables the co-expression of the sequences A and B into separate proteins.

19 Claims, 21 Drawing Sheets

Specification includes a Sequence Listing.

(51) Int. Cl.
| C12N 15/62 | (2006.01) |
| C12N 15/86 | (2006.01) |
| A61K 48/00 | (2006.01) |
| C07K 16/10 | (2006.01) |
| A61K 39/29 | (2006.01) |
| A61P 37/02 | (2006.01) |
| A61P 31/00 | (2006.01) |
| A61P 35/00 | (2006.01) |
| C12N 15/113 | (2010.01) |
| C12N 15/85 | (2006.01) |
| A61K 39/00 | (2006.01) |

(52) U.S. Cl.
CPC .............. *A61P 37/02* (2018.01); *C07K 16/00* (2013.01); *C12N 15/113* (2013.01); *C12N 15/62* (2013.01); *C12N 15/85* (2013.01); *C12N 15/86* (2013.01); *A61K 2039/505* (2013.01); *A61K 2039/5256* (2013.01); *C07K 2317/10* (2013.01); *C07K 2317/76* (2013.01); *C07K 2319/03* (2013.01); *C12N 2740/15043* (2013.01); *C12N 2810/6054* (2013.01); *C12N 2830/008* (2013.01); *C12N 2830/20* (2013.01); *C12N 2830/42* (2013.01); *C12N 2830/48* (2013.01); *C12N 2830/50* (2013.01)

(56) References Cited

U.S. PATENT DOCUMENTS

| 8,529,903 | B2* | 9/2013 | Daftary | A61P 7/00 424/153.1 |
| 8,680,241 | B2* | 3/2014 | Naparstek | A61P 1/04 530/387.1 |
| 8,771,960 | B2* | 7/2014 | Breitling | C07K 16/40 435/7.1 |
| 8,969,539 | B2* | 3/2015 | Tsurushita | C07K 16/2866 536/23.53 |
| 2006/0099206 | A1* | 5/2006 | Sinacore | C07K 16/00 536/23.53 |
| 2010/0303776 | A1* | 12/2010 | Samulski | C12N 15/63 435/325 |
| 2013/0035472 | A1* | 2/2013 | Horlick | C07K 16/00 530/350 |

OTHER PUBLICATIONS

Tsurushita et al., Effects of Intron Length on Differential Processing of Mouse μ Heavy-Chain mRNA. (Mol Cell Bio, 1987, 7:2602-2605) (Year: 1987).*
Galli et al., Relative position and strengths of poly(A) sites as well as transcription termination are critical to membrane versus secreted mu-chain expression during B-cell development (Genes & Development, 1987, 1:471-481) (Year: 1987).*
Luo et al., "Engineering human hematopoietic stem/progenitor cells to produce a broadly neutralizing anti-HIV antibody after in vitro maturation to human B lymphocytes", Blood, Feb. 12, 2009, pp. 1422-1431, vol. 113, No. 7, American Society of Hematology, US.
Fallot et al., "Alternative-splicing-based bicistronic vectors for ratio-controlled protein expression and application to recombinant antibody production", Nucleic Acids Research, Sep. 3, 2009, pp. e134-1-e134-10, vol. 37, No. 20.
Yu et al., "Use of Mutated Self-Cleaving 2A Peptides as a Molecular Rheostat to Direct Simultaneous Formation of Membrane and Secreted Anti-HIV Immunoglobulins", PLOS ONE, Nov. 28, 2012, p. e50438, vol. 7, No. 11.
Fusil et al., "A Lentiviral Vector Allowing Physiologically Regularted Membrane-anchored and Secreted Antibody Expression Depending on B-cell Maturation Status", Molecular Therapy, Sep. 8, 2015, pp. 1734-1747, vol. 23, No. 11.
Szymczak et al., "Correction of multi-gene deficiency in vivo using a single 'self-cleaving' 2A peptide-based retroviral vector", Nature Biotechnology, Apr. 4, 2004, pp. 589-594, vol. 22, No. 5.
Girard-Gagnepain et al., "Baboon envelope pseudotyped LVs outperform VSV-G-LVs for gene transfer into early-cytokine-stimulated and resting HSCs", Blood, Jun. 20, 2014, pp. 1221-1231, vol. 124, No. 8.
Giang et al., "Human broadly neutralizing antibodies to the envelope glycoprotein complex of hepatitis C virus", Proceedings of the National Academy of Sciences, pp. 6205-6210, vol. 109, No. 16.
Horlick et al., "Simultaneous Surface Display and Secretion of Proteins from Mammalian Cells Facilitate Efficient in Vitro Selection and Maturation of Antibodies", Journal of Biological Chemistry, May 20, 2013, pp. 19861-19869.
Peterson, M., "Mechanisms Controlling Production of Membrane and Secreted Immunoglobulin During B Cell Development", Immunologic Research, Jan. 1, 2007, pp. 33-46, vol. 37, No. 1.

* cited by examiner

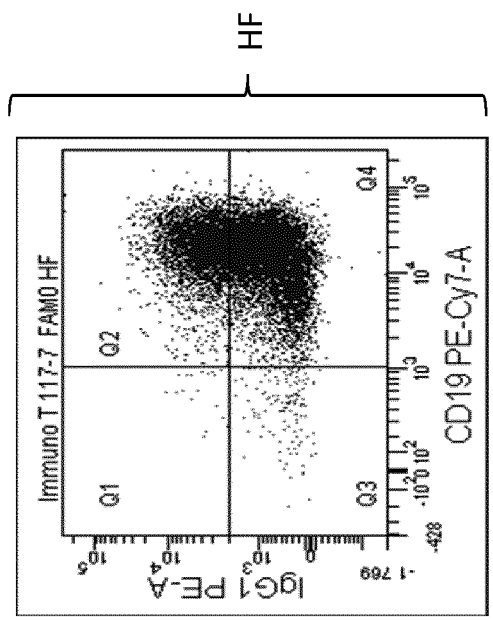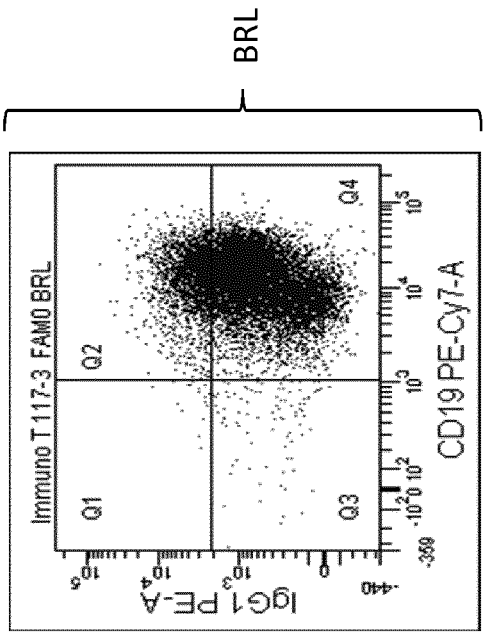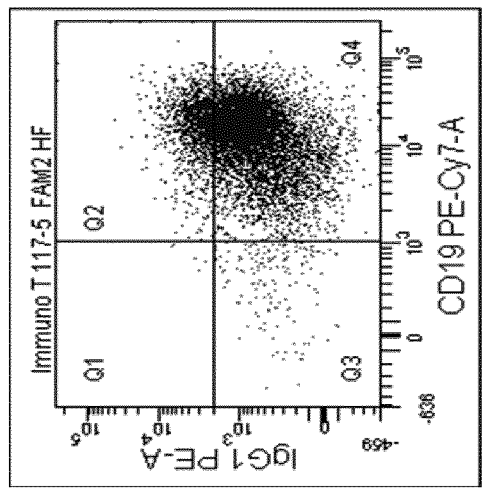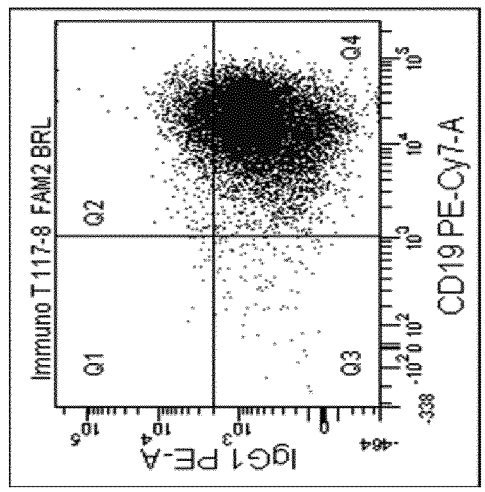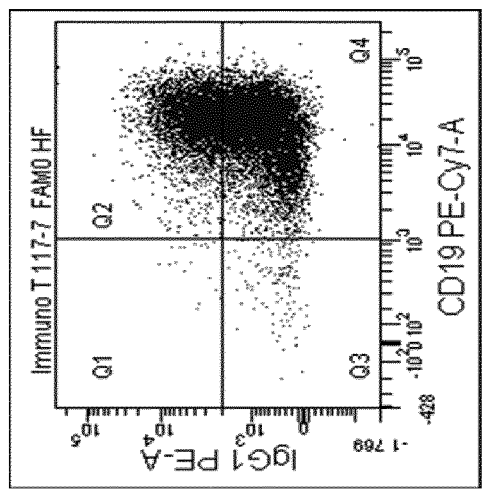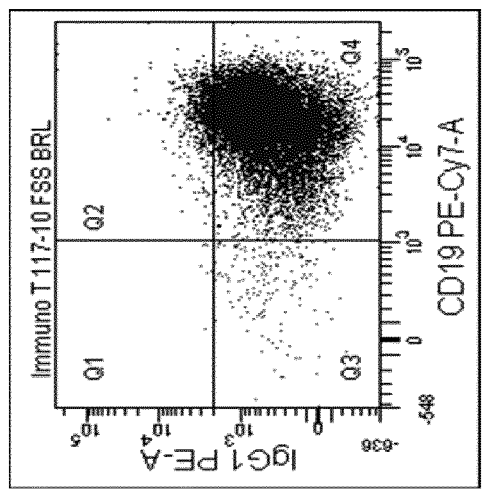
FIG 30

SEQUENCE LISTING

```
<160> NUMBER OF SEQ ID NOS: 32

<210> SEQ ID NO 1
<211> LENGTH: 8
<212> TYPE: PRT
<213> ORGANISM: Artificial Sequence
<220> FEATURE:
<223> OTHER INFORMATION: 2A peptides consensus motif
<220> FEATURE:
<221> NAME/KEY: misc_feature
<222> LOCATION: (2)..(2)
<223> OTHER INFORMATION: Xaa can be any naturally occurring amino acid
<220> FEATURE:
<221> NAME/KEY: misc_feature
<222> LOCATION: (4)..(4)
<223> OTHER INFORMATION: Xaa can be any naturally occurring amino acid

<400> SEQUENCE: 1

Asp Xaa Glu Xaa Asn Pro Gly Pro
1               5

<210> SEQ ID NO 2
```

```
<211> LENGTH: 22
<212> TYPE: PRT
<213> ORGANISM: Foot-and-mouth disease virus

<400> SEQUENCE: 2

Val Lys Gln Thr Leu Asn Phe Asp Leu Leu Lys Leu Ala Gly Asp Val
1               5                   10                  15

Glu Ser Asn Pro Gly Pro
            20

<210> SEQ ID NO 3
<211> LENGTH: 66
<212> TYPE: DNA
<213> ORGANISM: Foot-and-mouth disease virus

<400> SEQUENCE: 3
gtgaaacaga ctttgaattt tgaccttctc aagttggcag agacgttga gtccaaccct      60 gggccc                                                               66

<210> SEQ ID NO 4
<211> LENGTH: 18
<212> TYPE: PRT
<213> ORGANISM: Artificial Sequence
<220> FEATURE:
<223> OTHER INFORMATION: T2A peptide

<400> SEQUENCE: 4

Glu Gly Arg Gly Ser Leu Leu Thr Cys Gly Asp Val Glu Glu Asn Pro
1               5                   10                  15

Gly Pro

<210> SEQ ID NO 5
<211> LENGTH: 51
<212> TYPE: DNA
<213> ORGANISM: Artificial Sequence
<220> FEATURE:
<223> OTHER INFORMATION: sequence encoding T2A peptide

<400> SEQUENCE: 5
ggcaggggaa gtcttctaac atgcggggac gtggaggaaa tcccggcccc                51

<210> SEQ ID NO 6
<211> LENGTH: 19
<212> TYPE: PRT
<213> ORGANISM: Artificial Sequence
<220> FEATURE:
<223> OTHER INFORMATION: P2A peptide

<400> SEQUENCE: 6

Ala Thr Asn Phe Ser Leu Leu Lys Gln Ala Gly Asp Val Glu Glu Asn
1               5                   10                  15

Pro Gly Pro

<210> SEQ ID NO 7
<211> LENGTH: 57
<212> TYPE: DNA
<213> ORGANISM: Artificial Sequence
<220> FEATURE:
<223> OTHER INFORMATION: sequence encoding P2A peptide

<400> SEQUENCE: 7
gccacaaact tttctttact aaaacaagcg ggagatgttg aggaaaaccc cgggcct       57
```

```
<210> SEQ ID NO 8
<211> LENGTH: 20
<212> TYPE: PRT
<213> ORGANISM: Artificial Sequence
<220> FEATURE:
<223> OTHER INFORMATION: E2A peptide

<400> SEQUENCE: 8

Gln Cys Thr Asn Tyr Ala Leu Leu Lys Leu Ala Gly Asp Val Glu Ser
1               5                   10                  15

Asn Pro Gly Pro
            20

<210> SEQ ID NO 9
<211> LENGTH: 60
<212> TYPE: DNA
<213> ORGANISM: Artificial Sequence
<220> FEATURE:
<223> OTHER INFORMATION: sequence encoding E2A peptide

<400> SEQUENCE: 9
cagtgtacta actatgcttt gttgaaatta gctggggatg ttgagagcaa ccccggccct      60

<210> SEQ ID NO 10
<211> LENGTH: 66
<212> TYPE: DNA
<213> ORGANISM: Artificial Sequence
<220> FEATURE:
<223> OTHER INFORMATION: codon optimized sequence encoding F2A peptide

<400> SEQUENCE: 10
gtgaaacaga ctttgaattt tgaccttctc aagttggcgg gagacgtgga gtccaaccca      60
gggccc                                                                66

<210> SEQ ID NO 11
<211> LENGTH: 54
<212> TYPE: DNA
<213> ORGANISM: Artificial Sequence
<220> FEATURE:
<223> OTHER INFORMATION: codon optimized sequence encoding T2A peptide

<400> SEQUENCE: 11
gagggcagag gaagtctgct aacatgcggt gacgtcgagg agaatcctgg ccca            54

<210> SEQ ID NO 12
<211> LENGTH: 60
<212> TYPE: DNA
<213> ORGANISM: Artificial Sequence
<220> FEATURE:
<223> OTHER INFORMATION: codon optimized sequence encoding E2A peptide

<400> SEQUENCE: 12
caatgtacta actacgcttt gttgaaactc gctggcgatg ttgaaagtaa ccccggtcct      60

<210> SEQ ID NO 13
<211> LENGTH: 5
<212> TYPE: PRT
<213> ORGANISM: Artificial Sequence
<220> FEATURE:
<223> OTHER INFORMATION: furin cleavage site consensus sequence
<220> FEATURE:
<221> NAME/KEY: misc_feature
<222> LOCATION: (2)..(2)
<223> OTHER INFORMATION: Xaa can be any naturally occurring amino acid

<400> SEQUENCE: 13
```

Arg Xaa Lys Arg Arg
1               5

<210> SEQ ID NO 14
<211> LENGTH: 4
<212> TYPE: PRT
<213> ORGANISM: Artificial Sequence
<220> FEATURE:
<223> OTHER INFORMATION: furin cleavage site

<400> SEQUENCE: 14

Arg Ala Lys Arg
1

<210> SEQ ID NO 15
<211> LENGTH: 12
<212> TYPE: DNA
<213> ORGANISM: Artificial Sequence
<220> FEATURE:
<223> OTHER INFORMATION: sequence encoding a furin cleavage site

<400> SEQUENCE: 15
cgggctaaga ga                                                         12

<210> SEQ ID NO 16
<211> LENGTH: 1272
<212> TYPE: DNA
<213> ORGANISM: Artificial Sequence
<220> FEATURE:
<223> OTHER INFORMATION: MH promoter

<400> SEQUENCE: 16
ggattgttta tcttaggagg catgcttact gttaaaagac aggatatgtt tgaagtggct       60
tctgagaaaa atggttaaga aaattatgac ttaaaatgt gagagatttt caagtatatt      120
aatttttta actgtccaag tatttgaaat tcttatcatt tgattaacac ccatgagtga      180
tatgtgtctg gaattgaggc caaagcaagc tcagctaaga aatactagca cagtgctgtc      240
ggccccgatg cgggactgcg ttttgaccat cataaatcaa gtttattttt ttaattaatt      300
gagcgaagct ggaagcagat gatgaattag agtcaagatg gctgcatggg ggtctccggc      360
acccacagca ggtggcagga agcaggtcac cgcgagagtc tattttagga agcaaaaaaa      420
cacaattggt aaatttatca cttctggttg tgaagaggtg gttttgccca ggcccagatc      480
tgaaagtgct ctactgagca aaacaacacc tggacaattt gcgtttctaa ataaggcga       540
ggctgaccga aactgaaaag cttttttta actatctgaa tttcatttcc aatcttagct      600
tatcaactgc tagtttgtgc aaacagcata tcaacttcta aactgcattc attttttaaag     660
taagatgttt aagaaattaa acagtcttag ggagagttta tgactgtatt caaaaagttt      720
tttaaattag cttgttatcc cttcatgtga taactaatct caaatacttt ttcgatacct      780
cagagcatta ttttcataat gactgtgttc acaatcttt taggttaact cgttttctct      840
tgtgattaa ggagaaacac tttgatattc tgatagagtg gccttcattt tagtatttttt     900
caagaccact tttcaactac tcactttagg ataagtttta ggtaaaatgt gcatcattat      960
cctgaattat ttcagttaag catgttagtt ggtggcataa agaaaactc aatcagatag     1020
gtaccgcggg cccgggatcc gcaggattta gggcttggtc tctcagcatc ccacacttgt    1080
acagctgatg tggcatctgt gttttctttc tcatcctaga tcaggctttg agctgtgaaa    1140
taccctgcct catgcatatg caaataacct gaggtcttct gagataaata tagatatatt    1200
ggtgccctga gagcatcaca taacaaccac attcctcctc tgaagaagcc cctgggagca    1260

```
cagctcatca cc                                                       1272

<210> SEQ ID NO 17
<211> LENGTH: 904
<212> TYPE: DNA
<213> ORGANISM: Artificial Sequence
<220> FEATURE:
<223> OTHER INFORMATION: FEEK promoter

<400> SEQUENCE: 17
taaaccggtg agtttcatgg ttacttgcct gagaagatta aaaaagtaa tgctaccttaa    60 tgagggagag tcccagggac caagatagca actgtcatag caaccgtcac actgctttgg   120
tcaaggagaa gacccttgg ggaactgaaa acagaacctt gagcacatct gttgctttcg    180
ctcccatcct cctccaacag gctgggtgg agcactccac acctttcac cggtcgtacg     240 gctcagccag agtaaaaatc acacccatga cctggccact gagggcttga tcaattcact   300
ttgaatttgg cattaaatac cattaaggta tattaactga ttttaaaata agatatattc   360
gtgaccatgt ttttaacttt caaaaatgta gctgccagtg tgtgatttta tttcagttgt   420
acaaaatatc taaacctata gcaatgtgat taataaaaac ttaaacatat tttccagtac   480
cttaattctg tgataggaaa atttaatct gagtatttta atttcataat ctctaaaata    540
gtttaatgat tgtcattgt gttgctgtcg ttaccccag ctgatctcaa aagtgatatt     600
taaggagatt attttggtct gcaacaactt gatagggctc agcctctccc acccaacggg   660
tggaatcccc cagaggggga tttccaagag gccacctggc agttgctgag ggtcagaagt   720
gaagctagcc acttcctctt aggcaggtgg ccaagattac agttgacccg tacgtgcagc   780
tgtgcccagc ctgccccatc ccctgctcat ttgcatgttc ccagagcaca acctcctgcc   840
ctgaagcctt attaataggc tggtcacact ttgtgcagga gtcagactca gtcaggacac   900
agct                                                                904

<210> SEQ ID NO 18
<211> LENGTH: 153
<212> TYPE: DNA
<213> ORGANISM: Artificial Sequence
<220> FEATURE:
<223> OTHER INFORMATION: pAM signal

<400> SEQUENCE: 18
aataaatatc tttattttca ttacatctgt gtgttggttt tttgtgtgaa tcgatagtac    60
taacatacgc tctccatcaa aacaaaacga aacaaaacaa actagcaaaa taggctgtcc   120
ccagtgcaag tgcaggtgcc agaacatttc tct                                153

<210> SEQ ID NO 19
<211> LENGTH: 205
<212> TYPE: DNA
<213> ORGANISM: Artificial Sequence
<220> FEATURE:
<223> OTHER INFORMATION: RRE

<400> SEQUENCE: 19
tccttgggtt cttgggagca gcaggaagca ctatgggcgc agcgtcaatg acgctgacgg    60
tacaggccag acaattattg tctggtatag tgcagcagca gaacaatttg ctgagggcta   120
ttgaggcgca acagcatctg ttgcaactca cagtctgggg catcaagcag ctccaggcaa   180
gaatcctggc tgtggaaaga tacct                                         205
```

<210> SEQ ID NO 20
<211> LENGTH: 125
<212> TYPE: DNA
<213> ORGANISM: Artificial Sequence
<220> FEATURE:
<223> OTHER INFORMATION: cPPT

<400> SEQUENCE: 20

```
tccacaattt taaagaaaaa gggggattg ggggtacag tgcagggga agaatagtag    60
acataatagc aacagacata caaactaaag aattacaaaa acaaattaca aaaattcaaa   120
atttt                                                              125
```

<210> SEQ ID NO 21
<211> LENGTH: 589
<212> TYPE: DNA
<213> ORGANISM: Artificial Sequence
<220> FEATURE:
<223> OTHER INFORMATION: WPRE

<400> SEQUENCE: 21

```
aatcaacctc tggattacaa aatttgtgaa agattgactg gtattcttaa ctatgttgct    60
ccttttacgc tatgtggata cgctgcttta atgcctttgt atcatgctat tgcttcccgt   120
atggctttca ttttctcctc cttgtataaa tcctggttgc tgtctcttta tgaggagttg   180
tggcccgttg tcaggcaacg tggcgtggtg tgcactgtgt tgctgacgc aaccccccact   240
ggttggggca ttgccaccac ctgtcagctc ctttccggga cttttcgcttt cccctcccct   300
attgccacgg cggaactcat cgccgcctgc cttgcccgct gctggacagg gctcggctg    360
ttgggcactg acaattccgt ggtgttgtcg gggaagctga cgtccttttcc atggctgctc   420
gcctgtgttg ccacctggat tctgcgcggg acgtccttct gctacgtccc ttcggccctc   480
aatccagcgg accttccttc ccgcggcctg ctgccggctc tgcggcctct ccgcgtctt    540
cgccttcgcc ctcagacgag tcggatctcc ctttgggccg cctccccgc               589
```

<210> SEQ ID NO 22
<211> LENGTH: 594
<212> TYPE: DNA
<213> ORGANISM: Artificial Sequence
<220> FEATURE:
<223> OTHER INFORMATION: optimized WPRE

<400> SEQUENCE: 22

```
aatcaacctc tggattacaa aatttgtgaa agattgactg gtattcttaa ctatgttgct    60
ccttttacgc tatgtggata cgctgcttta atgcctttgt atcatgctat tgcttcccgt   120
atggctttca ttttctcctc cttgtataaa tcctggttgc tgtctcttta tgaggagttg   180
tggcccgttg tcaggcaacg tggcgtggtg tgcactgtgt tgctgacgc aaccccccact   240
ggttggggca ttgccaccac ctgtcagctc ctttccggga cttttcgcttt cccctcccct   300
attgccacgg cggaactcat cgccgcctgc cttgcccgct gctggacagg gctcggctg    360
ttgggcactg acaattccgt ggtgttgtcg gggaaatcat cgtccttttcc ttggctgctc   420
gcctgtgttg ccacctgcat tctgcgcggg acgtccttct gctacgtccc ttcggccctc   480
aatccagcgg accttccttc ccgcggcctg ctgccggctc tgcggcctct ccgcgtctt    540
cgccttcgcc ctcagacgag tcggatctcc ctttgggccg cctccccgca tcga         594
```

<210> SEQ ID NO 23
<211> LENGTH: 546

<212> TYPE: PRT
<213> ORGANISM: Artificial Sequence
<220> FEATURE:
<223> OTHER INFORMATION: modified BaEV envelope glycoprotein

<400> SEQUENCE: 23

Met Gly Phe Thr Thr Lys Ile Ile Phe Leu Tyr Asn Leu Val Leu Val
1               5                   10                  15

Tyr Ala Gly Phe Asp Asp Pro Arg Lys Ala Ile Glu Leu Val Gln Lys
            20                  25                  30

Arg Tyr Gly Arg Pro Cys Asp Cys Ser Gly Gly Gln Val Ser Glu Pro
        35                  40                  45

Pro Ser Asp Arg Val Ser Gln Val Thr Cys Ser Gly Lys Thr Ala Tyr
    50                  55                  60

Leu Met Pro Asp Gln Arg Trp Lys Cys Lys Ser Ile Pro Lys Asp Thr
65                  70                  75                  80

Ser Pro Ser Gly Pro Leu Gln Glu Cys Pro Cys Asn Ser Tyr Gln Ser
                85                  90                  95

Ser Val His Ser Ser Cys Tyr Thr Ser Tyr Gln Gln Cys Arg Ser Gly
            100                 105                 110

Asn Lys Thr Tyr Tyr Thr Ala Thr Leu Leu Lys Thr Gln Thr Gly Gly
        115                 120                 125

Thr Ser Asp Val Gln Val Leu Gly Ser Thr Asn Lys Leu Ile Gln Ser
130                 135                 140

Pro Cys Asn Gly Ile Lys Gly Gln Ser Ile Cys Trp Ser Thr Thr Ala
145                 150                 155                 160

Pro Ile His Val Ser Asp Gly Gly Gly Pro Leu Asp Thr Thr Arg Ile
                165                 170                 175

Lys Ser Val Gln Arg Lys Leu Glu Glu Ile His Lys Ala Leu Tyr Pro
            180                 185                 190

Glu Leu Gln Tyr His Pro Leu Ala Ile Pro Lys Val Arg Asp Asn Leu
        195                 200                 205

Met Val Asp Ala Gln Thr Leu Asn Ile Leu Asn Ala Thr Tyr Asn Leu
    210                 215                 220

Leu Leu Met Ser Asn Thr Ser Leu Val Asp Asp Cys Trp Leu Cys Leu
225                 230                 235                 240

Lys Leu Gly Pro Pro Thr Pro Leu Ala Ile Pro Asn Phe Leu Leu Ser
                245                 250                 255

Tyr Val Thr Arg Ser Ser Asp Asn Ile Ser Cys Leu Ile Ile Pro Pro
            260                 265                 270

Leu Leu Val Gln Pro Met Gln Phe Ser Asn Ser Ser Cys Leu Phe Ser
        275                 280                 285

Pro Ser Tyr Asn Ser Thr Glu Glu Ile Asp Leu Gly His Val Ala Phe
    290                 295                 300

Ser Asn Cys Thr Ser Ile Thr Asn Val Thr Gly Pro Ile Cys Ala Val
305                 310                 315                 320

Asn Gly Ser Val Phe Leu Cys Gly Asn Asn Met Ala Tyr Thr Tyr Leu
                325                 330                 335

Pro Thr Asn Trp Thr Gly Leu Cys Val Leu Ala Thr Leu Leu Pro Asp
            340                 345                 350

Ile Asp Ile Ile Pro Gly Asp Glu Pro Val Pro Ile Pro Ala Ile Asp
        355                 360                 365

His Phe Ile Tyr Arg Pro Lys Arg Ala Ile Gln Phe Ile Pro Leu Leu
    370                 375                 380

-continued

```
Ala Gly Leu Gly Ile Thr Ala Ala Phe Thr Thr Gly Ala Thr Gly Leu
385                 390                 395                 400

Gly Val Ser Val Thr Gln Tyr Thr Lys Leu Ser Asn Gln Leu Ile Ser
            405                 410                 415

Asp Val Gln Ile Leu Ser Ser Thr Ile Gln Asp Leu Gln Asp Gln Val
        420                 425                 430

Asp Ser Leu Ala Glu Val Val Leu Gln Asn Arg Arg Gly Leu Asp Leu
    435                 440                 445

Leu Thr Ala Glu Gln Gly Gly Ile Cys Leu Ala Leu Gln Glu Lys Cys
450                 455                 460

Cys Phe Tyr Val Asn Lys Ser Gly Ile Val Arg Asp Lys Ile Lys Thr
465                 470                 475                 480

Leu Gln Glu Glu Leu Glu Arg Arg Lys Asp Leu Ala Ser Asn Pro
            485                 490                 495

Leu Trp Thr Gly Leu Gln Gly Leu Leu Pro Tyr Leu Leu Pro Phe Leu
        500                 505                 510

Gly Pro Leu Leu Thr Leu Leu Leu Leu Thr Ile Gly Pro Cys Ile
    515                 520                 525

Phe Asn Arg Leu Thr Ala Phe Ile Asn Asp Lys Leu Asn Ile Ile His
530                 535                 540

Ala Met
545

<210> SEQ ID NO 24
<211> LENGTH: 84
<212> TYPE: DNA
<213> ORGANISM: Artificial Sequence
<220> FEATURE:
<223> OTHER INFORMATION: F2A/furin peptide sequence

<400> SEQUENCE: 24
cgggctaaga gagcaccggt gaaacagact ttgaattttg accttctcaa gttggcggga      60
gacgtggagt ccaacccagg gccc                                             84

<210> SEQ ID NO 25
<211> LENGTH: 20
<212> TYPE: DNA
<213> ORGANISM: Artificial Sequence
<220> FEATURE:
<223> OTHER INFORMATION: F primer

<400> SEQUENCE: 25
tgtgtgcccg tctgttgtgt                                                  20

<210> SEQ ID NO 26
<211> LENGTH: 20
<212> TYPE: DNA
<213> ORGANISM: Artificial Sequence
<220> FEATURE:
<223> OTHER INFORMATION: R primer

<400> SEQUENCE: 26
gagtcctgcg tcgagagagc                                                  20

<210> SEQ ID NO 27
<211> LENGTH: 20
<212> TYPE: DNA
<213> ORGANISM: Artificial Sequence
<220> FEATURE:
<223> OTHER INFORMATION: probe
```

<400> SEQUENCE: 27
cagtggcgcc cgaacaggga					20

<210> SEQ ID NO 28
<211> LENGTH: 22
<212> TYPE: DNA
<213> ORGANISM: Artificial Sequence
<220> FEATURE:
<223> OTHER INFORMATION: actin F primer

<400> SEQUENCE: 28
tccgtgtgga tcggcggctc ca				22

<210> SEQ ID NO 29
<211> LENGTH: 21
<212> TYPE: DNA
<213> ORGANISM: Artificial Sequence
<220> FEATURE:
<223> OTHER INFORMATION: actin R primer

<400> SEQUENCE: 29
ctgcttgctg atccacatct g					21

<210> SEQ ID NO 30
<211> LENGTH: 24
<212> TYPE: DNA
<213> ORGANISM: Artificial Sequence
<220> FEATURE:
<223> OTHER INFORMATION: actin probe

<400> SEQUENCE: 30
cctggcctcg ctgtccacct tcca				24

<210> SEQ ID NO 31
<211> LENGTH: 375
<212> TYPE: DNA
<213> ORGANISM: Artificial Sequence
<220> FEATURE:
<223> OTHER INFORMATION: typical B3 sequence

<400> SEQUENCE: 31
tgagtgccac ggccggcaag cccccgctcc ccaggctctc ggggtcgcgc gaggatgctt		60 ggcacgtacc ccgtgtacat acttcccagg cacccagcat ggaaataaag cacccagcgc		120 ttccctgggc ccctgcgaga ctgtgatggt tctttccacg ggtcaggccg agtctgaggc		180 ctgagtggca tgagggaggc agagtgggtc ccactgtccc cacactggcc caggctgtgg		240 tggggagctg acctcaggac attgttggcc catcccggcc gggccctaca tcctgggtcc		300 tgccacagag ggaatcaccc ccagaggccc aagcccaggg ggacacagca ctgaccaccc		360 ccttcctgtc cagag					375

<210> SEQ ID NO 32
<211> LENGTH: 217
<212> TYPE: DNA
<213> ORGANISM: Artificial Sequence
<220> FEATURE:
<223> OTHER INFORMATION: typical B4 sequence

```
<400> SEQUENCE: 32
gtcggccgca cgttgtcccc agctgtcctt gacattgtcc cccatgctgt cacaaactgt        60
ctctgacact gtcccacagg ctgtccccac ctgtccctga cgctgcgggt gggtgggcct       120
tgggggcaga gaggtggcct cagtgccctg aggggtgggt ggggctcggg ggcagggctg       180
tggcctcgct caccctgtg ctgtgccttg cctacag                                217
```

LENTIVIRAL VECTOR EXPRESSING MEMBRANE-ANCHORED OR SECRETED ANTIBODY

The present invention concerns lentiviral vectors enabling the expression of membrane-anchored and secreted antibodies by B cells.

Adaptive immune responses are principally mediated by two pathways, cellular immunity and humoral responses. The latter pathway involves B cells and the production of immunoglobulins (Ig). During B cell lymphopoïesis, immunoglobulins are initially expressed as a membrane-anchored form, the B cell receptor (BCR). Rearrangement of the heavy and light chain loci by the V(D)J recombination process allows the assembly of a functional BCR of IgM and IgD isotypes and its presentation at the cell surface during the early phase of maturation. For protein T-cell-dependent antigens, triggering of the membrane BCR on naïve B cells initiates a maturation process that includes two types of modifications of Ig genes: i) introduction of point mutations in the variable regions (somatic hypermutation/SHM) that allows Ag-driven diversification of the repertoire and ii) Ig class switch recombination (CSR) allowing the Ig variable regions to associate with downstream heavy chain constant regions of G, A or E isotype. Both CSR and SHM for the most part take place in the germinal centers (GC) that form in secondary lymphoid organs. The GC reaction leads to the production of both memory and effector (plasma cells) B lymphocytes. Further encounter of antigen (Ag) by memory B cells through ligation to the BCR leads to rapid clonal expansion and maturation into plasma cells, cells which are specialized in antibody (Ab) secretion. These memory-derived antibody-secreting cells are characterized by the production of high-affinity Abs responsible for the increased efficiency of the secondary humoral response. At the last step of B cell development, plasma cells (PC) produce soluble and secreted forms of the immunoglobulin which conserves the same specificity and isotype as the BCR expressed on their corresponding progenitors.

B cells can be engineered, either directly or through modification of CD34$^+$ hematopoietic stem cells (HSC) differentiated into B cells, to produce specific antibodies, which may provide novel approaches for active immunotherapy strategies against specific pathogens or pathological cells such as cancer cells. However, the continuous delivery of secretory IgG, induced either by gene transfer or by passive immunotherapy, could cause, through Ab-mediated selective pressure, major drawbacks like induction of neutralizing Ab escape virus mutants or resistant tumoral cells.

There is thus an important need of new tools for B cell reprogrammation which mimic the physiological regulation of Ab production, from Ag recognition by B cells to Ab secretion by plasma cells at the right time after specific expansion of the BCR-expressing cells.

The switch from the membrane-associated form to the secreted form of Igs is controlled by mRNA processing. This involves alternative splicing and polyadenylation of a single Ig pre-mRNA that can produce both forms of the Ig proteins (i.e, membrane-anchored vs. secreted), depending on the B cell maturation state. In B cells, this pre-mRNA is preferentially processed to an mRNA encoding the membrane-anchored form of the Ig (BCR), while plasma cells process the same pre-mRNA to allow the production of the secreted protein (Abs) by replacing a hydrophobic transmembrane anchor with a hydrophilic C-terminal tail. Additionally, B cell differentiation into large antibody-secreting plasma cells requires total commitment to protein synthesis through the expansion of the secretory pathway to form a highly developed endomembrane transport network. The complex network of all the above mentioned regulatory elements is responsible for the tightly regulated conditional expression of the BCR vs. the secreted form of Ig.

The present invention results from the development by the present inventors of a new method for reprogramming B cells with ectopic Ab-expressing constructs that can regulate the transition from BCR to secreted Ig in a manner dependent on cell maturation and differentiation.

More particularly, the inventors designed a conditional lentiviral vector coding for the broadly human cross-neutralizing AR3A Ab directed against the E2 envelope glycoprotein of HCV, said antibody being described in Giang et al. (2012) *Proc. Natl. Acad. Sci. USA* 109:6205-6210, wherein said conditional lentiviral vector (LV) recapitulates the natural spatio-temporal regulation of membrane-anchored vs. secreted IgG1 forms in primary B cells. This new conditional lentiviral vector thus enables the LV-mediated modification of human B cells allowing neutralizing antibody expression in a physiological manner.

The present invention thus concerns a multicistronic nucleic acid, in particular an isolated multicistronic nucleic acid, comprising:

A) a sequence comprising successively:
   A1) a sequence encoding the light chain variable domain of an antibody of interest, fused in the frame with
   A2) a sequence encoding the constant region of the light chain of an immunoglobulin Ig;
and
B) a sequence comprising successively:
   B1) a sequence encoding the heavy chain variable domain of said antibody of interest, fused in the frame with
   B2) a sequence encoding the constant regions of the heavy chain of a immunoglobulin Ig' in secretory form;
   B3) an intronic sequence of the gene of the heavy chain of said immunoglobulin Ig', said intronic sequence comprising an internal 5' splice site enabling the splicing of said intronic sequence B3) and a secretory-specific poly(A) (pAS) signal from the 3' terminal exon of said gene;
   B4) a sequence, in frame with sequence B1), encoding the transmembrane and cytoplasmic domains M1 and M2 of the immunoglobulin Ig' BCR, wherein said sequence B4) comprises, between the coding sequences of the M1 and M2 domains, an intronic sequence containing a splice site enabling the splicing of said intronic sequence between the M1 and M2 coding sequences; and
   B5) a membrane-anchored specific poly(A) signal (pAM), after the stop codon of the M2 domain, wherein the multicistronic nucleic acid enables the co-expression of the sequences A and B into separate proteins.

This conditional lentiviral vector may also be used to make B cells express and secrete conditionally effector proteins in order to target cells or micro-organisms expressing specific antigens.

The present invention thus also concerns a nucleic acid, in particular an isolated nucleic acid, encoding an antigen-binding domain/effector protein chimera, said nucleic acid comprising:

A) a sequence encoding an antigen-binding domain AbD specifically interacting with an antigen of interest; and B) a sequence comprising successively:

B2) a sequence encoding an effector protein EfP;

B3) an intronic sequence of the gene of the heavy chain of an immunoglobulin Ig', said intronic sequence comprising an internal 5' splice site enabling the splicing of said intronic sequence B3) and a secretory-specific poly(A) (pAS) signal from the 3' terminal exon of said gene;

B4) a sequence, in frame with sequence B2), encoding the transmembrane and cytoplasmic domains M1 and M2 of the immunoglobulin Ig' BCR, wherein said sequence B4) comprises, between the coding sequences of the M1 and M2 domains, an intronic sequence containing a splice site enabling the splicing of said intronic sequence between the M1 and M2 coding sequences; and B5) a membrane-anchored specific poly(A) signal (pAM), after the stop codon of the M2 domain, wherein the nucleic acid enables the expression of the sequences A and B into a single protein.

In the case where the antigen-binding domain AbD and/or the effector protein are formed by two subunits, the present invention also concerns a multicistronic nucleic acid, in particular an isolated multicistronic nucleic acid, encoding an antigen-binding domain/effector protein chimera, said nucleic acid comprising:

A) a sequence comprising successively:

A1) a sequence encoding a first subunit AbD1 of an antigen-binding domain AbD, fused in the frame with A2) a first subunit EfP1 of an effector protein EfP, or optionally a sequence encoding an effector protein EfP;

and

B) a sequence comprising successively:

B1) a sequence encoding a second subunit AbD2 of the antigen-binding domain AbD, AbD2 forming in combination with AbD1 an antigen-binding domain specifically interacting with an antigen of interest, said sequence 131 being fused in the frame with B2) a sequence encoding a second subunit EfP2 of the effector protein EfP or a sequence encoding the effector protein EfP;

B3) an intronic sequence of the gene of the heavy chain of an immunoglobulin Ig', said intronic sequence comprising an internal 5' splice site enabling the splicing of said intronic sequence B3) and a secretory-specific poly(A) (pAS) signal from the 3' terminal exon of said gene;

B4) a sequence, in frame with sequence B1), encoding the transmembrane and cytoplasmic domains M1 and M2 of the immunoglobulin Ig' BCR, wherein said sequence B4) comprises, between the coding sequences of the M1 and M2 domains, an intronic sequence containing a splice site enabling the splicing of said intronic sequence between the M1 and M2 coding sequences; and B5) a membrane-anchored specific poly(A) signal (pAM), after the stop codon of the M2 domain, wherein the multicistronic nucleic acid enables the co-expression of the sequences A and B into separate proteins.

DETAILED DESCRIPTION OF THE INVENTION

Definitions

In the context of the invention, the term "nucleic acid" refers to polynucleotides such as deoxyribonucleic acid (DNA), and, where appropriate, ribonucleic acid (RNA). Preferably, the nucleic acid of the invention is DNA. The term should also be understood to include, as equivalents, analogs of either RNA or DNA made from nucleotide analogs.

The term "isolated nucleic acid," as used herein, refers to a nucleic acid that is (i) free of sequences that normally flank one or both sides of the nucleic acid in a genome, (ii) incorporated into a vector or into the genomic DNA of an organism such that the resulting molecule is not identical to any naturally occurring vector or genomic DNA, or (iii) a cDNA, a genomic nucleic acid fragment, a fragment produced by polymerase chain reaction (PCR) or a restriction fragment. In addition, an isolated nucleic acid can include an engineered nucleic acid such as a recombinant DNA molecule that is part of a hybrid or fusion nucleic acid.

The nucleic acid of the invention can comprise coding and/or non-coding sequences. Coding nucleic acids have nucleotide sequences that are transcribed into RNA molecules that can be translated to create polypeptides. Non-coding nucleic acids, typically, are transcribed into RNAs that cannot be translated.

In the context of the invention, the term "multicistronic nucleic acid" refers to a nucleic acid, as defined above, comprising at least two cistrons.

All the nucleic acid sequences defined in the present application may be codon optimized. Codon optimization methods are known in the art and may be useful in efforts to achieve one or more of several goals. These goals include to match codon frequencies in target and host organisms to ensure proper folding, bias GC content to increase mRNA stability or reduce secondary structures, minimize tandem repeat codons or base runs that may impair gene construction or expression, customize transcriptional and translational control regions, insert or remove protein trafficking sequences, remove/add post translation modification sites in encoded protein (e.g. glycosylation sites), add, remove or shuffle protein domains, insert or delete restriction sites, modify ribosome binding sites and mRNA degradation sites, to adjust translational rates to allow the various domains of the protein to fold properly, or to reduce or eliminate problem secondary structures within the mRNA, or to avoid cryptic splicing sites as described in Fallot et al. (2009) *Nucleic Acids Res.* 37:e134 or Resse et al. (1997) *J. Comput. Biol.* 4:311-323. Codon optimization tools, algorithms and services are known in the art, non-limiting examples including services from GeneArt (Life Technologies), DNA2.0 (Menlo Park Calif.) and/or proprietary methods. Codon options for each amino acid are given in Table 1.

TABLE 1

Codon options

| Amino acid | Single letter code | Codon options |
|---|---|---|
| Isoleucine | I | ATT, ATC, ATA |
| Leucine | L | CTT, CTC, CTA, CTG, TTA, TTG |

TABLE 1-continued

Codon options

| Amino acid | Single letter code | Codon options |
|---|---|---|
| Valine | V | GTT, GTC, GTA, GTG |
| Phenylalanine | F | TTT, TTC |
| Methionine | M | ATG |
| Cysteine | C | TGT, TGC |
| Alanine | A | GCT, GCC, GCA, GCG |
| Glycine | G | GGT, GGC, GGA, GGG |
| Proline | P | CCT, CCC, CCA, CCG |
| Threonine | T | ACT, ACC, ACA, ACG |
| Serine | S | TCT, TCC, TCA, TCG, AGT, AGC |
| Tyrosine | Y | TAT, TAC |
| Tryptophan | W | TGG |
| Glutamine | Q | CAA, CAG |
| Asparagine | N | AAT, AAC |
| Histidine | H | CAT, CAC |
| Glutamic acid | E | GAA, GAG |
| Aspartic acid | D | GAT, GAC |
| Lysine | K | AAA, AAG |
| Arginine | R | CGT, CGC, CGA, CGG, AGA, AGG |
| Stop codons | Stop | TAA, TAG, TGA |

By "a sequence at least x % identical to a reference sequence", it is intended that the sequence differs from the reference sequence by up to 100-x amino acid, respectively nucleotide, alterations per each 100 amino acids, respectively nucleotides, of the reference sequence.

The alignment and the determination of the percentage of identity may be carried out manually or automatically using for instance the Needle program which is based on the Needleman and Wunsch algorithm, described in Needleman and Wunsch (1970) J. Mol Biol. 48:443-453, with for example the following parameters for polypeptide sequence comparison: comparison matrix: BLOSUM62, gap open penalty: 10 and gap extend penalty: 0.5, end gap penalty: false, end gap open penalty=10, end gap extend penalty=0.5; and the following parameters for polynucleotide sequence comparison: comparison matrix: DNAFULL; gap open penalty=10, gap extend penalty=0.5, end gap penalty: false, end gap open penalty=10, end gap extend penalty=0.5.

In the context of the invention, the term "immunoglobulin" relates to proteins of the immunoglobulin superfamily, preferably to antigen receptors such as antibodies or the B cell receptor (BCR). The immunoglobulins are characterized by a structural domain, i.e., the immunoglobulin domain, having a characteristic immunoglobulin (Ig) fold. The term encompasses membrane-anchored immunoglobulins as well as secretory immunoglobulins. Membrane-anchored or membrane-bound immunoglobulins are also termed surface immunoglobulins or membrane immunoglobulins, which are generally part of the BCR.

Immunoglobulins generally comprise several chains, typically two identical heavy chains and two identical light chains which are linked via disulfide bonds. These chains are primarily composed of immunoglobulin domains, including the $V_L$ domain (light chain variable domain), the $C_L$ domain (light chain constant domain), the $V_H$ domain (heavy chain variable domain) and the $C_H$ domains (heavy chain constant domains) $C_H1$, optionally a hinge region, $C_H2$, $C_H3$, and optionally $C_H4$.

There are five main heavy chain classes (or isotypes) which determine the functional activity of an antibody molecule: mu (μ) for IgM, delta (δ) for IgD, gamma (γ) for IgG, alpha (α) for IgA and epsilon (E) for IgE. In the context of the invention, the immunoglobulin may be an IgM, IgD, IgG, IgA or IgE. Preferably, the immunoglobulin is an IgG. As well-known from the skilled person, the IgG isotype encompasses four subclasses: the subclasses IgG1, IgG2, IgG3 and IgG4. In the context of the invention, the immunoglobulin may be of any IgG subclass. Preferably, the immunoglobulin is an IgG1. As opposed to the heavy chains of secretory immunoglobulins, the heavy chains of membrane-anchored immunoglobulins comprise a transmembrane domain and a short cytoplasmic domain at their carboxy-terminus.

In mammals, there are two types of light chain, lambda (λ) and kappa (κ). Both types of light chains may associate indifferently with any class of heavy chain.

The immunoglobulin chains comprise a variable region and a constant region. The constant region is essentially conserved within the different isotypes of the immunoglobulins, wherein the variable part is highly divers.

The variable regions of both light ($V_L$) and heavy ($V_H$) chains determine binding recognition and specificity to the antigen. The $V_H$ and $V_L$ regions can be further subdivided into regions of hypervariability, termed complementarity determining regions (CDR), interspersed with regions that are more conserved, termed framework regions (FR). Each $V_H$ and $V_L$ is composed of three CDRs and four FRs, arranged from amino-terminus to carboxy-terminus in the following order: FR1, CDR1, FR2, CDR2, FR3, CDR3, FR4.

The constant region domains of the light ($C_L$) and heavy ($C_H$) chains confer important biological properties such as antibody chain association, secretion, trans-placental mobility, complement binding, and binding to Fc receptors (FcR).

As used herein, the term "constant regions of an immunoglobulin heavy chain" preferably refers to the regions of the immunoglobulin heavy chain composed of the $C_H1$, optionally a hinge region, $C_H2$, $C_H3$, and optionally the $C_H4$ domain, preferably comprising one or more, preferably all, potential linker and/or hinge regions. It is particularly preferred that the constant region of an immunoglobulin heavy chain comprises one or more cysteine residues which are capable of mediating the association with another constant region of an immunoglobulin heavy chain by disulfide-bonding.

As used herein, the term "B cell receptor" or "BCR" refers to the antigen receptor at the plasma membrane of B cells. The B cell receptor is generally composed of a membrane-anchored antibody, as defined above, associated with Ig-α and Ig-β heterodimers which are capable of signal transduction.

As used herein, the term "transmembrane and cytoplasmic domain of a B cell receptor" preferably refers to the transmembrane domain of the membrane-anchored immunoglobulin part of the B cell receptor, i.e., the transmembrane and cytoplasmic domain of the membrane-anchored immunoglobulin heavy chain.

As well-known from the skilled person, the transmembrane and cytoplasmic domains M1 and M2 of a membrane-anchored immunoglobulin heavy chain, are important for the anchoring and the BCR signaling after antigen stimulation as they contain a transmembrane sequence and a cytosolic domain that associate with other BCR components at the cell surface to promote signal transduction.

By "antibody of interest" is meant herein an immunoglobulin, as defined above, comprising a light chain variable domain and a heavy chain variable domain which determine its antigen specificity, and a light chain constant domain and heavy chain constant domains, and which is intended to be produced by a cell. Preferably, the amino acid sequence of the antibody of interest and/or the coding sequence of the antibody of interest and/or the sequence of the gene encoding the antibody of interest is known or can be determined by the skilled person.

The antibody of interest is preferably a monoclonal antibody. The antibody of interest may also be a chimeric antibody.

A "chimeric" antibody refers to an antibody made up of components from at least two different sources. In certain embodiments, a chimeric antibody comprises a portion of an antibody derived from a first species fused to another molecule, e.g., a portion of an antibody derived from a second species. In certain such embodiments, a chimeric antibody comprises a portion of an antibody derived from a non-human animal fused to a portion of an antibody derived from a human. In certain such embodiments, a chimeric antibody comprises all or a portion of a variable region of an antibody derived from a non-human animal fused to a constant region of an antibody derived from a human.

In particular, the antibody of interest may be a humanized antibody. A "humanized" antibody refers to a non-human antibody that has been modified so that it more closely matches (in amino acid sequence) a human antibody. In certain embodiments, amino acid residues outside of the antigen binding residues of the variable region of the non-human antibody are modified. For the most part, humanized antibodies are human immunoglobulins (recipient antibody) in which residues from a hypervariable region of the recipient are replaced by residues from a hypervariable region of a non-human species (donor antibody) such as mouse, rat, rabbit or nonhuman primate having the desired specificity, affinity, and capacity. In certain embodiments, a humanized antibody is constructed by replacing all or a portion of a CDR of a human antibody with all or a portion of a CDR from another antibody, such as a non-human antibody, having the desired antigen binding specificity. In certain embodiments, a humanized antibody comprises variable regions in which all or substantially all of the CDRs correspond to CDRs of a non-human antibody and all or substantially all of the framework regions (FRs) correspond to FRs of a human antibody. In certain such embodiments, a humanized antibody further comprises a constant region (Fc) of a human antibody. Furthermore, humanized antibodies may comprise residues that are not found in the recipient antibody or in the donor antibody.

The antibody of interest may further be a human antibody.

The term "human antibody" refers to a monoclonal antibody that contains human antibody sequences and does not contain antibody sequences from a non-human animal. In certain embodiments, a human antibody may contain synthetic sequences not found in native antibodies. The term is not limited by the manner in which the antibodies are made.

For example, in various embodiments, a human antibody may be made in a transgenic mouse, by phage display, by human B-lymphocytes, or by recombinant methods.

As used herein, the term "intronic sequence" or "intron" refers to any nucleotide sequence within a gene that is removed by RNA splicing during maturation of the final RNA product. Alternative splicing of introns within a gene acts to introduce greater variability of protein sequences translated from a single gene, allowing multiple related proteins to be generated from a single gene and a single precursor mRNA transcript. The control of alternative RNA splicing is performed by a complex network of signaling molecules that respond to a wide range of intracellular and extracellular signals. Introns contain several short sequences that are important for efficient splicing, such as acceptor and donor sites at either end of the intron as well as splicing enhancer or silencer sequences, or a branch point site, which are required for proper splicing by the spliceosome.

Intronic sequences of genes encoding immunoglobulin heavy chains are well-known or can be identified by the skilled person. For all genes encoding immunoglobulin heavy chains, there is an exon in the constant region that is either spliced at an internal 5' splice site or cleaved and polyadenylated at the secretory-specific poly(A) signal (pAS). When the pre-mRNA is cleaved at the pAS, the mRNA encodes the secretory immunoglobulin. When the pre-mRNA is spliced to one or two downstream exons and the downstream poly(A) signal (pAM or membrane-anchored specific poly(A)) is used, the mRNA encodes the membrane-anchored immunoglobulin. More specifically, the pAS signal is preferably about 100-150 nucleotides downstream of the last constant region exon which encodes the 3' end of the secretory-specific mRNA.

The 3' end of membrane-anchored specific mRNA is encoded by a large portion of the last constant region and by two downstream exons, M1 and M2. Membrane-anchored specific mRNA is produced when splicing of the last constant region exon to M1 takes place using the internal 5' splice site within the last constant region exon, polyadenylation occurs at the pAM site at the end of M2, and preferably the intronic sequence between the M1 and M2 exons is also spliced.

As well-known from the skilled person, the highly conserved core poly(A) signal sequence 5'-AAUAAA-3' is typically embedded in an AU-rich region (28 of 29 nucleotides surrounding the AAUAAAA are A or U) which enhances pAS signal use. The pAS signal preferably contains two downstream GU-rich sequences that are located at 1 and 38 nucleotides from the cleavage site.

As well-known from the skilled person, splice sites comprise a donor site (at the 5' end of the intron) and an acceptor site (at the 3' end of the intron). The splice donor site preferably includes an almost invariant sequence GU at the 5' end of the intron, within a larger, less highly conserved region. The splice acceptor site at the 3' end of the intron terminates the intron preferably with an almost invariant AG sequence. Upstream from the AG there is preferably a polypyrimidine tract (region rich in C and U), upstream of which is the branchpoint, which preferably includes an adenine nucleotide. The consensus sequence for an intron is thus typically: A-G-[cut]-G-U-R-A-G-U (donor site) . . . intron sequence . . . Y-U-R-A-C (branch sequence 20-50 nucleotides upstream of acceptor site) . . . Y-rich-N-C-A-G-[cut]-G (acceptor site).

As will be clear for the skilled person, the sequences mentioned herein which are involved in mRNA splicing play a role at the mRNA stage. Accordingly, they may be referred to interchangeably as DNA sequences (with A, T, C or G nucleotides) or as RNA sequences (with A, U, C or G nucleotides).

In the context of the invention, the term "antigen-binding domain" refers to any peptide, polypeptide, scaffold-type molecule, peptide display molecule or polypeptide-containing construct that is capable of specifically binding a particular antigen of interest.

Antigen-binding domains include for example antigen-binding portions of antibodies, single-chain antibodies, single domain antibodies (e.g., VHH antibodies from camelid animals), peptides that specifically interact with a particular antigen (e.g. peptibodies), receptor molecules that specifically interact with a particular antigen, proteins comprising a ligand-binding portion of a receptor that specifically binds a particular antigen, antigen-binding scaffolds (e.g. DARPins, HEAT repeat proteins, ARM repeat proteins, tetratricopeptide repeat proteins and other scaffolds based on naturally occurring repeat proteins), and aptamers or portions thereof.

The antigen-binding domain may be formed by a single peptide or protein AbD, or by the combination of two antigen-binding domain subunits, AbD1 and AbD2, the combination of these two subunits enabling the specific interaction of the global antigen-binding domain with an antigen of interest.

In the context of the invention, the term "effector protein" refers to a protein that is involved in the regulation of a biological signaling pathway. Preferably, the effector protein is an immune effector protein or a cell death inducing effector protein.

By "immune effector protein" is meant herein a protein that is involved in the regulation of an immune system pathway. Examples of immune effector proteins include cytokines.

By "cell death inducing effector protein" is meant herein a protein that is involved in cell death signaling pathway, in particular in apoptosis signaling pathway.

The effector protein may be formed by a single peptide or protein EfP, or by the combination of two effector protein subunits, EfP1 and EfP2, the combination of these two subunits forming an active effector protein EfP.

By "combination" is meant herein any interaction linking two subunits defined above, such as a disulfide bond.

As used herein, the term "B cell" refers to a B lymphocyte. B cell precursors reside in the bone marrow where immature B cells are produced. Very briefly, B cell development occurs through several stages, each stage representing a change in the genome content at the antibody loci. In the genomic heavy chain variable region, there are three segments, V, D, and J, which recombine randomly, in a process called VDJ rearrangement to produce a unique variable region in the immunoglobulin of each B cell. Similar rearrangements occur for the light chain variable region except that there are only two segments involved, V and J. After complete rearrangement, the B cell reaches the IgM+ immature stage in the bone marrow. These immature B cells present a membrane-anchored IgM, i.e., BCR, on their surface and migrate to the spleen, where they are called transitional B cells. Some of these cells differentiate into mature B lymphocytes. Mature B cells expressing the BCR on their surface circulate the blood and lymphatic system performing the role of immune surveillance. They do not produce secretory immunoglobulins until they become fully activated. Each B cell has a unique receptor protein that will bind to one particular antigen. Once a B cell encounters its antigen and receives an additional signal from a T helper cell, it can further differentiate into either a plasma B cell expressing and secreting secretory immunoglobulins or a memory B cell.

Multicistronic Nucleic Acid

The present inventors designed a specific multicistronic nucleic acid encoding an antibody of interest capable of:
 driving the co-expression of the sequences encoding respectively the light and heavy chains of this antibody of interest into separate proteins, and
 driving the expression of a membrane-anchored form and/or a secreted form of said antibody of interest depending on the maturation step of the B cell into which it was incorporated.

Preferably, the multicistronic nucleic acid of the invention comprises or consists of at least 1000 nucleotides, more preferably at least 2000 nucleotides, 2500, 3000, 3500, 3600, 3700, 3800, 3900, 4000, 4100 or at least 4180 nucleotides.

Co-Expression of the Sequences A and B

The multicistronic nucleic acid according to the invention enables the co-expression of the sequences A and B which it contains, into separate proteins.

In particular, the sequences A and B can be expressed into separate proteins via the production of separate mRNAs or via the production of a single mRNA.

When the sequences A and B are expressed into separate proteins via the production of separate mRNAs, these sequences A and B are preferably under the control of different promotors or under the control of a unique bidirectional promotor, such as a bidirectional combination of a synthetic sequence composed of the minimal CMV promoter associated with a strong B cell specific promoter/enhancer (B29 or FEEK).

In a preferred embodiment, the sequences A and B are expressed into separate proteins via the production of a single mRNA. More preferably, said sequences A and B are linked by a linking sequence enabling the co-expression of the sequences A and B in a single mRNA.

Such linking sequences are well-known from the skilled person and described for example in Chan et al. (2011) *PLoS One* 6:e28885. Examples of linking sequences enabling the co-expression of two sequences in a single mRNA include viral internal ribosome entry site (IRES) sequences and sequences encoding 2A oligopeptides.

In a preferred embodiment, said sequences A and B are linked by a sequence encoding a 2A oligopeptide.

"2A oligopeptides", "2A peptides" or "CHYSEL" were identified in the Foot and Mouth Disease Virus (FMDV) and later in other genera of Picornaviridae. These peptides "self-cleave" their primary 2A/2B polyproteins by a ribosomal "skipping" mechanism which entails inhibition of the peptide bond formation between the C-terminal glycine residue of the 2A peptide and the N-terminal proline residue of the 2B peptide. These peptides share a consensus motif -DxExNPG↓P- (SEQ ID NO: 1) for the "skipping" function, where ↓ represents the position of "skipping". Examples of 2A peptides include F2A peptide from FMDV, T2A peptide from Thosea asigna virus, P2A peptide from Porcine teschovirus-1 and E2A peptide from Equine rhinitis A virus, these peptides being typically disclosed in Szymczak et al. (2004) *Nature Biotech.* 22:589-594.

F2A peptide typically consists of the sequence VKQTLNFDLLKLAGDVESNPGP (SEQ ID NO: 2). F2A peptide is typically encoded by the nucleotide sequence 5'-gtg aaa cag act ttg aat ttt gac ctt ctc aag ttg gca gga gac gtt gag tcc aac cct ggg ccc-3' (SEQ ID NO: 3). T2A peptide typically consists of the sequence EGRGSLLTCGDVEENPGP (SEQ ID NO: 4). T2A peptide is typically encoded by the nucleotide sequence 5'-ggc agg gga agt ctt cta aca tgc ggg gac gtg gag gaa aat ccc ggc ccc-3' (SEQ ID NO: 5). P2A peptide typically consists of the sequence ATNFSLLKQAGDVEENPGP (SEQ ID NO: 6). P2A peptide is typically encoded by the nucleotide sequence 5'-gcc aca aac ttt tct tta cta aaa caa gcg gga gat gtt gag gaa aac ccc ggg cct-3' (SEQ ID NO: 7). E2A typically consists of the sequence QCTNYALLKLAGDVESNPGP (SEQ ID NO: 8). E2A peptide is typically encoded by the nucleotide sequence 5'-cag tgt act aac tat gct ttg ttg aaa tta gct ggg gat gtt gag agc aac ccc ggc cct-3' (SEQ ID NO: 9).

Preferably said sequences A and B are linked by a nucleotide sequence encoding a 2A peptide consisting of a sequence at least 80% identical, more preferably at least 90%, 95, 96, 97, 98, 99, 99.5, 99.6, 99.7, 99.8, 99.9 identical or 100% identical to the sequence ID NO: 2, 4, 6 or 8, provided that said 2A peptide retains the "skipping" property defined above.

Still preferably, said sequences A and B are linked by a nucleotide sequence at least 80% identical, more preferably at least 90%, 95, 96, 97, 98, 99, 99.5, 99.6, 99.7, 99.8, 99.9 identical or 100% identical to the sequence SEQ ID NO: 3, 5, 7 or 9, provided that the peptide encoding by this nucleotide sequence retains the "skipping" property defined above.

Preferably, said sequences A and B are linked by a nucleotide sequence encoding the FMDV 2A peptide, as defined above.

Codon-optimized sequences of the sequences encoding these 2A peptides are known from the skilled person and for example described in Szymczak et al. (2004) *Nature Biotech.* 22:589-594. A codon-optimized sequence of the sequence encoding the F2A peptide is typically the sequence 5'-gtg aaa cag act ttg aat ttt gac ctt ctc aag ttg gcg gga gac gtg gag tcc aac cca ggg ccc-3' (SEQ ID NO: 10). A codon-optimized sequence of the sequence encoding the T2A peptide is typically the sequence 5'-gag ggc aga gga agt ctg cta aca tgc ggt gac gtc gag gag aat cct ggc cca-3' (SEQ ID NO: 11) A codon-optimized sequence of the sequence encoding the E2A peptide is typically the sequence 5'-caa tgt act aac tac gct ttg ttg aaa ctc gct ggc gat gtt gaa agt aac ccc ggt cct-3' (SEQ ID NO: 12)

Preferably said sequences A and B are linked by a codon-optimized nucleotide sequence of 2A peptide selected from the group consisting of SEQ ID NO: 10, 11 and 12.

Preferably said sequences A and B are linked by a codon-optimized nucleotide sequence encoding the FMDV 2A peptide, in particular of sequence SEQ ID NO: 10, as described for example in Yu et al. (2012) *PLoS One* 7:e50438.

It is particularly useful to include a sequence encoding a furin cleavage site before the sequence encoding the 2A peptide. Indeed, such a furin cleavage site enables withdrawing the residual 2A peptide, as described in Fang et al. (2005) *Nat. Biotechnol.* 23:584-590.

Accordingly, in a particular embodiment, said sequences A and B are linked by a nucleotide sequence including a sequence encoding a furin cleavage site and a sequence, preferably a codon-optimized nucleotide sequence, encoding a 2A peptide, preferably the FMDV 2A peptide.

Furin cleavage sites are well-known from the skilled person and for example described in Fang et al. (2005) *Nat. Biotechnol.* 23:584-590 and Fang et al. (2007) *Mol. Therapy* 15:1153-1159. A furin cleavage site typically consists of the consensus sequence RXK/RR (SEQ ID NO: 13). Preferably, the furin cleavage site consists of the sequence RAKR (SEQ ID NO: 14). Such a furin cleavage site is typically encoded by the nucleotide sequence 5'-cgggctaagaga-3'(SEQ ID NO: 15).

In the particular embodiment where the nucleic acid encodes an antigen-binding domain/effector protein chimera formed by single subunits and where the nucleic acid thus enables the expression of the sequences A and B into a single protein, the sequences A and B are preferably linked by a sequence encoding a protein linker which may be cleavable or not.

Preferably a B-cell specific promoter is operably linked to the sequence A defined above. Accordingly, in a preferred embodiment, the muticistronic nucleic acid of the invention further comprises, before said sequence A, a B-cell specific promoter operably linked to said sequence A.

As used herein, the term "operably linked" is used to describe the connection between regulatory elements and a gene or its coding region. That is, gene expression is typically placed under the control of certain regulatory elements, for example constitutive or inducible promoters, tissue-specific regulatory elements, and enhancers. A gene or coding region is said to be "operably linked to" or "operatively linked to" or "operably associated with" the regulatory elements, meaning that the gene or coding region is controlled or influenced by the regulatory element.

In the context of the invention, the term "B-cell specific promoter" refers to any promoter/enhancer sequences that are capable of directing specific transgene expression in B cells. For example, a B cell-specific promoter may be capable of directing transgene expression in immature, transitional or mature B cells, plasmablasts and/or plasma cells. A B cell-specific promoter may also be capable of directing transgene expression throughout B-cell development from hematopoietic cells in primary and secondary lymphoid organs. A B cell-specific promoter is preferably capable of driving transgene expression without affecting B-cell development.

As used herein, the B cell-specific promoter may be the promoter/enhancer sequence of any B-cell specific gene, and/or variants or engineered portions thereof, that normally controls the expression of genes expressed in a B-cell, examples of which include promoters/enhancers of CD19, CD20, CD21, CD22, CD23, CD24, CD40, CD72, Blimp-1, CD79b (also known as B29 or Ig beta), mb-1 (also known as Ig alpha), tyrosine kinase blk, VpreB, immunoglobulin heavy chain, immunoglobulin κ light chain, immunoglobulin λ light chain and immunoglobulin J-chain. In a particular embodiment, the B cell-specific promoter is an immunoglobulin light chain promoter, in particular an immunoglobulin κ light chain or an immunoglobulin λ light chain, more particularly an immunoglobulin κ light chain; or a CD19 promoter.

Other examples of B cell-specific promoter include synthetic promoters, such as the B29 promoter and enhancer chimera, the MH promoter and the EEK (also called FEEK) promoter.

As well-known from the skilled person and described for example in Sather et al. (2011) *Mol. Ther.* 19:515-525, the B29 promoter and enhancer chimera contains the immunoglobulin β (Igβ) (B29) promoter combined with the immunoglobulin μ enhancer (EμB29).

As well-known from the skilled person and described for example in the international application WO 2010/059876, the MH promoter contains the human μ heavy chain promoter (VHp) preceded by the iEμ enhancer flanked by matrix association regions (MAR), and is typically of sequence 5'-ggattgttta tcttaggagg catgcttact gttaaaagac aggatatgtt tgaagtggct tctgagaaaa atggttaaga aaattatgac ttaaaaatgt gagagatttt caagtatatt aatttttta actgtccaag tatttgaaat tcttatcatt tgattaacac ccatgagtga tatgtgtctg gaattgaggc caaagcaagc tcagctaaga aatactagca cagtgctgtc ggccccgatg cgggactgcg ttttgaccat cataaatcaa gttatttt ttaattaatt gagcgaagct ggaagcagat gatgaattag agtcaagatg gctgcatggg ggtctccggc acccacagca ggtggcagga agcaggtcac cgcgagagtc tattttagga agcaaaaaaa cacaattggt aaatttatca cttctggttg tgaagaggtg gttttgccca ggcccagatc tgaaagtgct ctactgagca aaacaacacc tggacaattt gcgtttctaa aataaggcga ggctgaccga aactgaaaag gcttttttta actatctgaa tttcattttcc aatcttagct tatcaactgc tagtttgtgc aaacagcata tcaacttcta aactgcattc attttaaag taagatgttt aagaaattaa acagtcttag ggagagttta tgactgtatt caaaagttt tttaaattag cttgttatcc cttcatgtga taactaatct caaatacttt ttcgatacct cagagcatta ttttcataat gactgtgttc acaatctttt taggttaact cgttttctct ttgtgattaa ggagaaacac tttgatattc tgatagagtg gccttcattt tagtatttt caagaccact tttcaactac tcactttagg ataagtttta ggtaaaatgt gcatcattat cct- gaattat ttcagttaag catgttagtt ggtggcataa gagaaaactc aatcagatag gtaccgcggg cccgggatcc gcaggattta gggcttggtc tctcagcatc ccacacttgt acagctgatg tggcatctgt gttttcttc tcatcctaga tcaggctttg agctgtgaaa tacctgcct catgcatatg caaataacct gaggtcttct gagataaata tagatatatt ggtgccctga gagcatcaca taacaaccac attcctcctc tgaagaagcc cctgggagca cagctcatca cc-3' (SEQ ID NO: 16). As well-known from the skilled person and described for example in the international application WO 2010/059876, the FEEK promoter contains the human κ light chain promoter (VKp) preceded by an intronic enhancer (iE$_K$), a MAR, and a 3' enhancer (3'E$_K$), and is typically of sequence 5'-taaaccggtg agtttcatgg ttacttgcct gagaagatta aaaaagtaa tgctaccta tgagggagag tcccagggac caagatagca actgtcatag caaccgtcac actgctttgg tcaaggagaa gacccttgg ggaactgaaa acagaaccttt gagcacatct gttgctttcg ctcccatcct cctccaacag ggctgggtgg agcactccac acccttcac cggtcgtacg gctcagccag agtaaaaatc acaccatga cctggccact gagggcttga tcaattcact ttgaatttgg cattaaatac cattaaggta tattaactga ttttaaaata agatatattc gtgaccatgt ttttaacttt caaaaatgta gctgccagtg tgtgatttta tttcagttgt acaaaatatc taaacc- tata gcaatgtgat taataaaaac ttaaacatat tttccagtac cttaattctg tataggaaa attttaatct gagtatttta atttcataat ctctaaaata gtttaatgat ttgtcattgt gttgctgtcg tttaccccag ctgatctcaa aagtgatatt taaggagatt atttttggtct gcaacaactt gataggctc agcctctccc acccaacggg tggaatccc cagagggga tttccaagag gccacctggc agttgctgag ggtcagaagt gaagctagcc acttcctctt aggcaggtgg ccaagattac agttgacccg tacgtgcagc tgtgcccagc ctgccccatc ccctgctcat ttgcatgttc ccagagcaca acctcctgcc ctgaagcctt attaataggc tggtcacact ttgtgcagga gtcagactca gtcaggacac agct-3' (SEQ ID NO: 17). Preferably, said B-cell specific promoter is the FEEK promoter.

More preferably, said B-cell specific promoter consists of a sequence at least 90%, 95, 96, 97, 98, 99, 99.5, 99.6, 99.7, 99.8, 99.9 identical or 100% identical to the sequence ID NO: 17, provided that said sequence retains the properties of the FEEK promoter.

Sequence A

The multicistronic nucleic acid of the invention comprises a sequence (A) comprising successively:
  A1) a sequence encoding the light chain variable domain
of an antibody of interest, as defined above, fused in the
    frame with
  A2) a sequence encoding the constant region of the light
    chain of an immunoglobulin Ig, as defined above.

Preferably, said sequence A1) includes the translation leader sequence of the sequence encoding said light chain variable domain.

As used herein, the "translation leader sequence" refers to a DNA sequence located between the promoter sequence of a gene and the coding sequence. The translation leader sequence is present in the fully processed mRNA upstream of the translation start sequence. The translation leader sequence may affect processing of the primary transcript to mRNA, mRNA stability or translation efficiency. Examples of translation leader sequences are well-known from the skilled person.

The sequence A2) encoding the constant region of the light chain of an immunoglobulin Ig may be the sequence encoding the constant region of the light chain of the antibody of interest or the sequence encoding the constant region of the light chain of a different immunoglobulin.

Preferably, said constant region of the light chain of an immunoglobulin Ig is a κ light chain constant region or a λ light chain constant region. More preferably, said constant region of the light chain of an immunoglobulin Ig is a κ light chain constant region.

In a particular embodiment, when the antigen-binding domain and the effector protein as defined above are respectively formed by a single subunit, the nucleic acid of the invention encoding an antigen-binding domain/effector protein chimera comprises a sequence (A) comprising a sequence encoding an antigen-binding domain AbD specifically interacting with an antigen of interest.

In another particular embodiment, when the antigen-binding domain and/or the effector protein as defined above are respectively formed by two subunits, the multicistronic nucleic acid of the invention encoding an antigen-binding domain/effector protein chimera comprises a sequence (A) comprising successively:
  A1) a sequence encoding a first subunit AbD1 of an
    antigen-binding domain AbD as defined above, fused in the
    frame with
  A2) a first subunit EfP1 of an effector protein EfP, or
    optionally a sequence encoding an effector protein EfP, as
    defined above.

In that specific embodiment, the sequences A1) and A2) may be further linked by a sequence encoding a protein linker which may be cleavable or not.

Preferably, the sequence A of the invention comprises or consists of at least 500 nucleotides, more preferably at least 600 nucleotides, 700, 710 or at least 720 nucleotides.

Sequence B

The multicistronic nucleic acid of the invention comprises a sequence (B) comprising successively:
  B1) a sequence encoding the heavy chain variable domain
    of the antibody of interest, as defined above, fused in
    the frame with
  B2) a sequence encoding the constant regions of the
    heavy chain of an immunoglobulin Ig' in secretory
    form, as defined above;
  B3) an intronic sequence of the gene of the heavy chain
    of said immunoglobulin Ig', said intronic sequence
    comprising an internal 5' splice site enabling the splicing of said intronic sequence B3) and a secretory-specific poly(A) (pAS) signal from the 3' terminal exon
    of said gene;
  B4) a sequence, in frame with sequence B1), encoding the
    transmembrane and cytoplasmic domains M1 and M2
    of the immunoglobulin Ig' BCR, as defined above,
    wherein said sequence B4) comprises, between the
    coding sequences of the M1 and M2 domains, an
    intronic sequence containing a splice site enabling the
    splicing of said intronic sequence between the M1 and
    M2 domains coding sequences;

B5) a membrane-anchored specific poly(A) signal (pAM), after the stop codon of the M2 domain.

Preferably, the sequence B of the invention comprises or consists of at least 1800 nucleotides, more preferably at least 1900 nucleotides, 2000, 2100, 2200, 2300, 2350, 2370, 2380, 2390, 2400, 2410 or at least 2420 nucleotides.

Preferably, said sequence B1) includes the translation leader sequence of the sequence encoding said heavy chain variable domain.

The sequence B2) encoding the constant regions of the heavy chain of an immunoglobulin Ig' in secretory form may be the sequence encoding the constant regions of the heavy chain of said antibody of interest or the sequence encoding the constant regions of the heavy chain of a different immunoglobulin, for example of the immunoglobulin Ig. In particular, the immunoglobulin Ig' heavy chain may be from any isotype. Preferably, the immunoglobulin Ig' heavy chain is from an IgG isotype.

In a preferred embodiment, the constant regions of the heavy chain of an immunoglobulin Ig' in secretory form are the constant regions of a secretory IgG heavy chain, in particular of a secretory $IgG_1$ or $IgG_2$ heavy chain. The use of the constant regions of a secretory $IgG_1$ heavy chain is particularly advantageous because such $IgG_1$ have a longer half-life and can induce opsonization-type or complement activation-type immune reactions.

Accordingly, in a preferred embodiment, the constant regions of a secretory immunoglobulin Ig' heavy chain are the constant regions of a secretory $IgG_1$ heavy chain.

In a particular embodiment, the sequence B2) encodes the three constant regions of a secretory immunoglobulin Ig' heavy chain, as defined above.

More preferably, the sequence B2) encodes successively the $C_1H$, hinge, $C_2H$ and $C_3H$ regions of a secretory immunoglobulin Ig' heavy chain. Still preferably, in the sequence encoding the $C_3H$ regions in the sequence B2), the stop codon of this $C_3H$ region is removed.

In a particular embodiment, when the antigen-binding domain and the effector protein as defined above are respectively formed by a single subunit, the nucleic acid of the invention encoding an antigen-binding domain/effector protein chimera comprises a sequence (B) comprising successively:

B2) a sequence encoding an effector protein EfP;
B3) an intronic sequence of the gene of the heavy chain of an immunoglobulin Ig', said intronic sequence comprising an internal 5' splice site enabling the splicing of said intronic sequence B3) and a secretory-specific poly(A) (pAS) signal from the 3' terminal exon of said gene;
B4) a sequence, in frame with sequence B2), encoding the transmembrane and cytoplasmic domains M1 and M2 of the immunoglobulin Ig' BCR, wherein said sequence B4) comprises, between the coding sequences of the M1 and M2 domains, an intronic sequence containing a splice site enabling the splicing of said intronic sequence between the M1 and M2 coding sequences; and
B5) a membrane-anchored specific poly(A) signal (pAM), after the stop codon of the M2 domain.

In another particular embodiment, when the antigen-binding domain and/or the effector protein as defined above are respectively formed by two subunits, the multicistronic nucleic acid of the invention encoding an antigen-binding domain/effector protein chimera comprises a sequence (B) comprising successively:

B1) a sequence encoding a second subunit AbD2 of the antigen-binding domain AbD, AbD2 forming in combination with AbD1 an antigen-binding domain specifically interacting with an antigen of interest, said sequence B1 being fused in the frame with
B2) a sequence encoding a second subunit EfP2 of the effector protein EfP or a sequence encoding the effector protein EfP;
B3) an intronic sequence of the gene of the heavy chain of an immunoglobulin Ig', said intronic sequence comprising an internal 5' splice site enabling the splicing of said intronic sequence B3) and a secretory-specific poly(A) (pAS) signal from the 3' terminal exon of said gene;
B4) a sequence, in frame with sequence B1), encoding the transmembrane and cytoplasmic domains M1 and M2 of the immunoglobulin Ig' BCR, wherein said sequence B4) comprises, between the coding sequences of the M1 and M2 domains, an intronic sequence containing a splice site enabling the splicing of said intronic sequence between the M1 and M2 coding sequences; and
B5) a membrane-anchored specific poly(A) signal (pAM), after the stop codon of the M2 domain, In that particular embodiment, the sequences B1) and B2) may further be linked by a sequence encoding a protein linker which may be cleavable or not.

The inventors demonstrated that the size of the intronic sequence B3) had an impact on the efficiency of splicing of the mRNA into a membrane-anchored and/or a secretory form. In particular, they demonstrated that optimal splicing could be obtained when the intronic sequence B3) was shortened to 400 to 350 nucleotides compared to the wild-type intronic sequence of the gene of said immunoglobulin Ig' heavy chain.

Accordingly, the intronic sequence B3) preferably comprises or consists of between 200 and 1500 nucleotides, still preferably between 250 and 1500 nucleotides, still preferably between 300 and 150 nucleotides, still preferably between 350 and 1500 nucleotides, still preferably between 360 and 1400 nucleotides, between 365 and 1300 nucleotides, between 366 and 1200 nucleotides, between 367 and 1100 nucleotides, between 368 and 1000 nucleotides, between 369 and 900 nucleotides, between 370 and 800 nucleotides, between 371 and 700 nucleotides, between 372 and 600 nucleotides, between 373 and 550 nucleotides, between 374 and 500 nucleotides, between 375 and 450 nucleotides, between 375 and 400 nucleotides, between 375 and 395 nucleotides, between 375 and 390 nucleotides, 389, 388, 387, 386, 385, 384, 383, 382, 381, 380, 379, 378, 377, 376 or 375 nucleotides. Still preferably, the intronic sequence B3) preferably comprises or consists of between 650 and 850 nucleotides, for example 781 or 681 nucleotides. Alternatively, the intronic sequence B3) comprises or consists of the full-length wild-type intronic sequence of the gene of said immunoglobulin Ig' heavy chain.

The internal 5' splice site included in the sequence B3) enables the splicing of said intronic sequence B3) between the last constant region and the downstream M1 exon to produce a membrane-anchored specific mRNA.

Preferably, the internal 5' splice site included in the sequence B3) comprises a donor site and an acceptor site. In particular embodiments, the internal 5' splice site included in the sequence B3) comprises a donor site located upstream from the sequence B3), typically at the end of the sequence B2), and an acceptor site preferably located at the end of said sequence B3).

Preferably, said donor site comprises a GU sequence. More preferably, said donor site consists of the sequence GU. Preferably, said donor site is located between 10 and 6 nucleotides before the end of the sequence B2), more preferably 8 nucleotides before the end of the sequence B2).

Preferably, said acceptor site comprises an AG sequence. Preferably, the acceptor site further comprises a polypyrimidine tract upstream from the AG sequence. More preferably, said acceptor site consists of the sequence AG. Preferably, said acceptor site is located 3 to 1 nucleotides before the beginning of the sequence B4), more preferably 2 nucleotides before the beginning of the sequence B4).

Preferably, the pAS signal included in the sequence B3) comprises the consensus sequence aataaa. Still preferably, the pAS signal comprises an AU-rich region, preferably comprising or consisting of 5 to 20 nucleotides, and/or a GU-rich region, preferably comprising or consisting of 5 to 20 nucleotides.

Most preferably, the pAS signal comprises or consists of the sequence aataaa or a sequence at least 80% identical, more preferably at least 90%, 95, 96, 97, 98, 99, 99.5, 99.6, 99.7, 99.8 or at least 99.9% identical to the sequence aataaa, provided that said sequence retains the polyadenylation signal property of pAS.

Alternatively, the pAS signal included in the sequence B3) is the natural pAS signal from another gene sequence.

Alternatively, the pAS signal included in the sequence B3) is a synthetic pAS signal. It may further comprise a transcription blocker sequence as defined below.

Still preferably, the sequence B3) further comprises splicing enhancer and/or silencer sequences.

The inventors demonstrated that the intronic sequence included in the sequence B4) between the sequences encoding the domains M1 and M2 was surprisingly necessary to obtain a suitable regulation of the expression of a membrane-anchored form and/or a secreted form of the antibody of interest according to the maturation step of the B cell into which it is incorporated.

They further demonstrated that the size of said intronic sequence had an impact on the efficiency of splicing of the mRNA into a membrane-anchored form. In particular, they demonstrated that optimal splicing could be obtained when said intronic sequence was shortened to 200 to 250 nucleotides compared to the wild-type intronic sequence.

Accordingly, the intronic sequence included in the sequence B4) preferably comprises or consists of between 200 and 1500 nucleotides, still preferably between 205 and 1400 nucleotides, between 206 and 1300 nucleotides, between 207 and 1200 nucleotides, between 208 and 1100 nucleotides, between 209 and 1000 nucleotides, between 210 and 900 nucleotides, between 211 and 800 nucleotides, between 212 and 700 nucleotides, between 213 and 600 nucleotides, between 214 and 500 nucleotides, between 215 and 400 nucleotides, between 216 and 350 nucleotides, between 217 and 300 nucleotides, between 217 and 250 nucleotides, 249, 248, 2487, 246, 245, 244, 243, 242, 241, 240, 239, 238, 237, 236, 235, 234, 233, 232, 231, 230, 229, 228, 227, 225, 224, 223, 221, 220, 219, 218 or 217 nucleotides. Alternatively, the intronic sequence included in the sequence B4) comprises or consists of the full-length corresponding wild-type intronic sequence.

The splice site included in the intronic sequence of said sequence B4) enables the splicing of said intronic sequence between the M1 and M2 exons to produce a membrane-anchored specific mRNA.

Preferably, the splice site included in the sequence B4) comprises a donor site and an acceptor site.

Preferably, said donor site in B4) comprises a GU sequence. More preferably, said donor site in B4) consists of the sequence GU. Preferably, said donor site in B4) is located 3 to 1 nucleotides after the end of the coding sequence of M1, more preferably 2 nucleotides after the end of the coding sequence of M1.

Preferably, said acceptor site in B4) comprises an AG sequence. Preferably, the acceptor site in B4) further comprises a polypyrimidine tract upstream from the AG sequence. More preferably, said acceptor site in B4) consists of the sequence AG. Preferably, said acceptor site in B4) is located 3 to 1 nucleotides before the beginning of the coding sequence of M2, more preferably 2 nucleotides before the beginning of the coding sequence of M2.

Still preferably, the splice site included in the sequence B4) comprises a AATAAA site and/or a branch point, as defined above.

Still preferably, the sequence B4) further comprises splicing enhancer and/or silencer sequences Preferably, the pAM signal included in the sequence B5) comprises the consensus sequence aataaa. Still preferably, the pAM signal further comprises an AT-rich region, preferably comprising or consisting of 5 to 20 nucleotides, and/or a GT-rich region, preferably comprising or consisting of 5 to 20 nucleotides.

The inventors surprisingly showed that the production of membrane-anchored specific mRNA was further optimized when the natural pAM signal was replaced by a synthetic pAM signal.

Preferably, the pAM signal is a synthetic pAM signal. Still preferably, said pAM signal further comprises a transcription blocker sequence. The presence of the transcription blocker sequence enables minimizing risks of mutagenesis associated with polymerase read-through.

Transcription blocker sequences are well-known from the skilled person and described for example in Enriquez-Harris et al. (1991) *EMBO J.* 10:1833-184 and Levitt et al. (1989) *Genes Dev.* 3:1019-1025.

Most preferably, the pAM signal comprises or consists of the sequence 5'-aataaatatctttatlitcattacatctgtgtgttggttttttgtgt-gaatcgatagtactaacatacgctctccatcaaaacaaaacg a aacaaaacaaactagcaaaataggctgtccccagtgcaagtgcaggtgccagaa-catttctct-3' (SEQ ID NO: 18) or a sequence at least 80% identical, more preferably at least 90%, 95, 96, 97, 98, 99, 99.5, 99.6, 99.7, 99.8 or at least 99.9% identical to the sequence SEQ ID NO: 18, provided that said sequence retains the polyadenylation signal property of pAM.

Alternatively, the pAM signal is the wild-type pAM signal of the gene of said immunoglobulin Ig' heavy chain or the natural pAS signal from another gene sequence.

Preferably, the sequences B3), B4) and/or B5) are codon-optimized to limit inappropriate splicing due to the possible presence of cryptic splice donor and acceptor sites. Techniques to identify cryptic splice donor and acceptor sites are well-known from the skilled person and include for example the use of the in silico splicing prediction algorithms, such as the algorithm described in Reese et al. (1997) J. Comput. Biol. 4:311-323. Once such cryptic splice donor and acceptor sites are identified, for example one to five nucleotides of these sites may be typically mutated for example by substitution to suppress them.

Preferably, the sequence B3) comprises or consists of the sequence 5'-tgagtgccacggccggcaagcccccgctccccaggctctc-ggggtcgcgcgaggatgcttggcacgtaccccgtgtacatacttcccag gcac-ccagcatggaaataaagcacccagcgcttccctgggccctgcgagactgtgat-ggttctttccacgggtcaggccgagtctgagg cctgagtggcatgagggagg-cagagtgggtcccactgtccccacactggcccaggctgtggtggggagctgacctcaggacattgttgg cccatcccggccgggccctacatcctgggtcctgc-
cacagagggaatcaccccagaggcccaagcccaggggggacacagcactga
ccacccccttcctgtccagag-3' (SEQ ID NO: 31).

Preferably, the sequence B4) comprises or consists of the sequence 5'-gtcggccgcacgttgtcccagctgtccttgacattgtcccccat-gctgtcacaaactgtctctgacactgtcccacaggctgtccccacctgt ccctgac-gctgcgggtgggtgggcttgggggcagagaggtggcctcagtgccctgagg-ggtgggtggggctcggggggcagggctgtg gcctcgctcacccctgtgct-gtgccttgcctacag-3' (SEQ ID NO: 32).

The inventors demonstrated that shortest the intronic sequences, the best diminution of viral titers was prevented. However, the intronic sequences should remain long enough to include suitable splicing and polyadenylation sites. Accordingly, in particularly preferred embodiments, the intronic sequence B3 comprises or consists of less than 150 nucleotides and more than 125 nucleotides and/or the intronic sequence included in the sequence B4) comprises or consists of less than 250 nucleotides and more than 210 nucleotides.

Most preferably, the multicistronic nucleic acid of the invention comprises successively:
the FEEK promoter,
a Kozak sequence
the translation leader sequence of the sequence encoding the light chain variable domain of the antibody of interest,
the sequence encoding the light chain variable domain of the antibody of interest,
the sequence encoding the constant domain of a κ light chain,
the sequence encoding a furin cleavage site,
an optimized sequence encoding the F2A peptide,
the translation leader sequence of the sequence encoding the heavy chain variable domain of the antibody of interest,
the sequence encoding the heavy chain variable domain of the antibody of interest,
the sequence encoding the $C_1H$ region of an immunoglobulin Ig', preferably of the antibody of interest, optionally optimized to suppress cryptic splice sites,
the sequence encoding the hinge region of Ig', preferably of the antibody of interest,
the sequence encoding the $C_2H$ region of Ig', preferably of the antibody of interest, optionally optimized to suppress cryptic splice sites,
the sequence encoding the $C_3H$ region of the secretory form of Ig', preferably of the antibody of interest, optionally optimized to suppress cryptic splice sites, and wherein the stop codon has been removed,
an optimized intronic sequence of the gene of the heavy chain of Ig', preferably of the antibody of interest, said intronic sequence comprising the internal 5' splice site and the secretory-specific poly(A) (pAS) signal of the 3' terminal exon of said gene,
the sequence encoding the M1 domain of the membrane-anchored version of Ig', preferably of the antibody of interest, optionally optimized to suppress cryptic splice sites,
an optimized intronic sequence of the gene encoding the M1 and M2 domains of the membrane-anchored form of Ig', preferably of the antibody of interest, containing acceptor and donor splicing sites,
the sequence encoding the M2 domain of the membrane-anchored form of Ig', preferably of the antibody of interest, optionally optimized to suppress cryptic splice sites, and including the stop codon, and a synthetic membrane-anchored specific poly(A) (pAM) signal and a transcription blocker.

The multicistronic nucleic acid of the invention may be transferred into a target cell, in particular into $CD34^+$ hematopoietic stem cells or B cells, by any transfection method well-known from the skilled person such as by electroporation, microporation or chemical techniques of transfection.

Alternatively, the multicistronic nucleic acid of the invention may be transferred into a target cell using viral vectors, such as adenovirus vectors, adeno associated virus (AAV) vectors or retrovirus vectors.

Transfer Retroviral Vector

The inventors specifically designed a transfer retroviral vector, which may be part of a retroviral packaging system, enabling the transfer, via retroviral vector particles, of the multicistronic nucleic acid of the invention into target cells, namely $CD34^+$ hematopoietic stem cells or B cells.

The present invention thus also concerns a transfer retroviral vector comprising:
(i) a transfer retroviral backbone, and
(ii) the multicistronic nucleic acid according to the invention or the nucleic acid of the invention in inverse orientation.

The transfer retroviral vector according to the invention is a transfer vector plasmid including the transgene to be transferred to the target cell. The retroviral vector according to the invention thus typically includes a transfer retroviral backbone, containing cis-acting genetic sequences of a retrovirus necessary for the vector to infect the target cell, and the multicistronic nucleic acid according to the invention or the nucleic acid according to the invention, which contains the sequence of interest to be transferred, namely the sequence encoding the antibody of interest. The transfer retroviral backbone thus typically includes the Long Terminal Repeats (LTRs) for the control of transcription and integration, the psi sequence necessary for encapsidation, and the Primer Binding Site (PBS) and polypurine track (PPT) sequences necessary for reverse transcription of the retroviral genome.

By "retrovirus" is meant a virus whose genome consists of a RNA molecule and that comprises a reverse-transcriptase, i.e. a member of the Retroviridae family. Retroviruses are divided into Oncovirus, Lentivirus and Spumavirus. Preferably, said retrovirus is an oncovirus, e.g. MLV, ALS, RSV or MPMV, a lentivirus, e.g. HIV-1, HIV-2, SIV, EIAV or CAEV, or a spumavirus such as HFV. Genomes of these retroviruses are readily available in databanks. More preferably, said retrovirus is a lentivirus, in particular HIV-1, HIV-2 or SIV.

As well-known from the skilled person, different types of transfer retroviral backbones can be used depending on the type of retroviral packaging system for which it is intended, namely the $1^{st}$ generation, $2^{nd}$ generation, $3^{rd}$ generation or $4^{th}$ generation of retroviral packaging system.

As well-known from the skilled person, in the $1^{st}$ generation of retroviral packaging system, live viral particles are produced from one transfer retroviral vector which carries all the retrovirus genes, namely the genes encoding retroviral core proteins, enzymes and accessory factors together with the transgene, and from a separate plasmid bearing an envelope gene. The transgene is typically under control of a wild-type 5'-LTR.

In contrast, as well-known from the skilled person, in the $2^{nd}$ generation of retroviral packaging system, 5 of the 9 retrovirus genes are deleted, leaving only the gag/pol and tat/rev regions. The transgene is typically under control of a wild-type 5'-LTR. The gag/pol/tat/rev regions are typically present on one separate plasmid.

As well-known from the skilled person, the 3$^{rd}$ generation of retroviral packaging system contains only gag, pol and rev genes. The gag/pol and rev genes are typically present on two separate plasmids. The transgene is typically under control of a chimeric 5'-LTR to ensure transcription in the absence of tat. In this chimeric 5'-LTR, the U3 region is typically replaced by a constitutively active promoter/enhancer, such as RSV or CMV.

Finally, as well-known from the skilled person, in the 4$^{th}$ generation of retroviral packaging system, the gag and pol genes are further codon-optimized and present in two separate plasmids.

Preferably, the transfer retroviral backbone contained in the transfer retroviral vector according to the invention is a third-generation or fourth generation retroviral backbone.

In a particularly preferred embodiment, the transfer retroviral backbone contained in the transfer retroviral vector according to the invention is a self-inactivating retroviral backbone.

By "self-inactivating retroviral backbone" is meant herein a retroviral construct which has a deletion in the U3 element of the 3'-LTR of the construct, and which results, after replication, in a deletion also in the 5'-LTR promoter and enhancer and prevents the transcription from the cell-specific internal promoter, which may otherwise activate silent cellular oncogenes.

In a particularly preferred embodiment, the transfer retroviral backbone contained in the transfer retroviral vector according to the invention is a 3$^{rd}$ generation or 4th generation self-inactivating retroviral backbone, more particularly a 3$^{rd}$ generation or 4th generation self-inactivating lentiviral backbone.

Thus, in a particular embodiment, the transfer retroviral backbone contained in the transfer retroviral vector according to the invention comprises successively:

(i1) a modified 5' LTR comprising a CMV enhancer substituted for the U3 region,
(i2) a psi and gag sequence,
(i3) a central polypurine tract (cPPT)/DNA flap sequence,
(i4) a Rev responsive element sequence (RRE),
(i5) a Woodchuck hepatitis virus posttranscriptional regulatory element sequence (WPRE), and
(i6) a self-inactivating 3' LTR comprising a deletion in the U3 region that renders the 5' LTR of the integrated provirus transcriptionally inactive.

By "Rev responsive element sequence" or "RRE" is meant herein a highly structured RNA segment present in the env coding region of unspliced and partially spliced viral mRNAs. In the presence of Rev, the retrovirus mRNAs that contain RRE can be exported from the nucleus to the cytoplasm to be translated and further packaged. The nucleic acid sequence of RRE is typically 5'-tccliggglicligg-gagcagcaggaagcactatgggcgcagcgtcaatgacgctgacggtacagg-ccagacaattattgtct ggtatagtgcagcagcagaacaatttgctgagggctatt-gaggcgcaacagcatctgttgcaactcacagtctggggcatca agcagctcc-aggcaagaatcctggctgtggaaagatacct-3' (SEQ ID NO: 19).

By "central polypurine tract (cPPT)/DNA flap sequence" is meant herein an initiation site, from which, during lentiviral retro-transcription, the DNA synthesis typically starts together with from the polypurine tract (PPT). The plus strand overlap obtained is called the central DNA flap (99 nucleotides), which is known to play a role in enhancing lentiviral provirus nuclear import. In the field of lentivector technology, it is now common knowledge that the introduction of this cis-acting cPPT element in the transfer vector plasmid highly increases the vector transduction efficiency in certain cell types, notably in hematopoietic stem cells, as described for example in Van Maele et al. (2003) *J. Virol.* 77:4685-4694. The nucleic acid sequence of cPPT is typically 5'-tccacaalittaaaagaaaaggggggattgggggtacagtgcaggg-gaaagaatagtagacataatagcaacagacat acaaactaaagaatta-caaaaacaaattacaaaaattcaaaatttt-3' (SEQ ID NO: 20).

By "Woodchuck hepatitis virus posttranscriptional regulatory element" or "WPRE" is meant herein a DNA sequence that, when transcribed, creates a tertiary structure enhancing expression. The presence of WPRE, in particular in combination with cPPT, thus enables increasing transduction efficiency and transgene expression. The nucleic acid sequence of WPRE is typically 5'-aatcaacctctggatta-caaaatttgtgaaagattgactggtattctt aactatgligctcclittacgctatgtg-gatacgctgclitaatgcctligtatcatgctattgcliccccgtatggctlicatlitc-tcctcctt gtataaatcctggttgctgtctclitatgaggagttgtggcccgttgt-caggcaacgtggcgtggtgtgcactgtglitgctgacgca accccccactgg-ttggggcattgccaccacctgtcagctcclitccgggactlicgclitcccctccct-attgccacggcggaact catcgccgcctgccttgcccgctgctggacagggg-ctcggctgttgggcactgacaattccgtggtgligtcggggaagctga cgtc-clitccatggctgctcgcctgtgligccacctggattctgcgcgggacgtcclictgc-tacgtccclicggccctcaatccag cggaccttcclicccgcggcctgctgcc-ggctctgcggcctcttccgcgtcttcgccttcgccctcagacgagtcggatctcc-cttt gggccgcctccccgc-3' (SEQ ID NO: 21). By WPRE is also meant herein an improved WPRE, such as the improved WPRE described in Zanta-Boussif et al. (2009) Gene Therapy 16:605-619, for example an improved WPRE of sequence 5'-aatcaacctctggattacaaaatligtgaaagattgactggtattct-taactatgligctcclittacgctatgtggatacgctgclita atgcctligtatcatgct-attgclicccgtatggctlicattlictcctccligtataaatcctggttgctgtctcli-tatgaggagttgtggc ccgligtcaggcaacgtggcgtggtgtgcactgtglit-gctgacgcaaccccccactggttggggcattgccaccacctgtcagc tcclitc-cgggactttcgctlicccccctccctattgccacggcggaactcatcgccgcct-gccttgcccgctgctggacaggggct cggctgttgggcactgacaattccgtg-gtgligtcggggaaatcatcgtcctlicctlggctgctcgcctgtgligccacctg-cattc tgcgcgggacgtcclictgctacgtcccttcggccctcaatccagcggac-cliccliccccgcggcctgctgccggctctgcggcc tcliccgcgtclicgcctt-cgccctcagacgagtcggatctccctligggccgcctccccgcatcga-3' (SEQ ID NO: 22).

In this particular embodiment, the multicistronic nucleic acid according to the invention is preferably located in inverse orientation between the sequences (i4) and (i5). Accordingly, in a particular embodiment, the transfer retroviral vector of the invention comprises successively:

(i1) a modified 5' LTR comprising a CMV enhancer substituted for the U3 region,
(i2) a psi and gag sequence,
(i3) a central polypurine tract (cPPT)/DNA flap sequence,
(i4) a Rev responsive element sequence (RRE),
(i5) a Woodchuck hepatitis virus posttranscriptional regulatory element sequence (WPRE), and
(i6) a self-inactivating 3' LTR comprising a deletion in the U3 region that renders the 5' LTR of the integrated provirus transcriptionally inactive, wherein the multicistronic nucleic acid or nucleic acid (ii) is located in inverse orientation between the sequences (i4) and (i5).

The fact that multicistronic nucleic acid or nucleic acid is located in inverse orientation in the transfer retroviral vector helps preserving splicing sites during vector particle production.

Conditional Pseudotyped Viral Vector Particle

The transfer retroviral vector defined in the section "Transfer retroviral vector" above is particularly useful for the production of a conditional pseudotyped viral vector particle allowing physiologically-regulated expression of membrane-anchored and/or secreted antibody by B cells.

The present invention thus also concerns a conditional pseudotyped viral vector particle allowing physiologically-regulated expression of membrane-anchored and/or secreted antibody by B cells, wherein said conditional pseudotyped viral vector particle comprises the multicistronic nucleic acid according to the invention and is preferably pseudotyped with a viral envelope glycoprotein targeting B cells or CD34$^+$ hematopoietic stem cells, as defined below.

The present invention also concerns a conditional pseudotyped viral vector particle allowing physiologically-regulated expression of membrane-anchored and/or secreted antigen-binding domain/effector protein chimera by B cells, wherein said conditional pseudotyped viral vector particle comprises the multicistronic nucleic acid or nucleic acid encoding the antigen-binding domain/effector protein chimera according to the invention and is preferably pseudotyped with a viral envelope glycoprotein targeting B cells or CD34$^+$ hematopoietic stem cells, as defined below.

By "conditional pseudotyped viral vector particle allowing physiologically-regulated expression of membrane-anchored and/or secreted antibody by B cells" is meant herein a pseudotyped viral vector particle capable to specifically transfer, into CD34$^+$ hematopoietic stem cells or B cells, a nucleic acid encoding an antibody, said antibody being expressed by said cells under membrane-anchored form and/or secreted form, depending on the maturation status of said cell.

The term "conditional" herein refers to the fact that the antibody is expressed conditionally under membrane-anchored form and/or under secreted form, the condition being the maturation status of the CD34$^+$ hematopoietic stem cell or B cell by which it is expressed.

Typically, the conditional pseudotyped viral vector particles of the invention enables the main expression of an antibody of interest under membrane-anchored form by mature B cells and the main expression of that antibody of interest under secreted form by plasma cells.

In order to specifically target CD34$^+$ hematopoietic stem cells and B cells, it is particularly advantageous to use a conditional viral vector particle pseudotyped with an envelope protein enabling the specific transduction of these cells.

Accordingly, in a particular embodiment, the conditional pseudotyped viral vector particle of the invention further comprises:
  modified measles virus (MV), in particular Edmonston measles virus, hemagglutinin (H) and fusion (F) glycoproteins, wherein the cytoplasmic tail domains are truncated,
  a chimeric envelope glycoprotein which comprises or consists in a fusion of the transmembrane and extracellular domain of a baboon endogenous retrovirus (BaEV) envelope glycoprotein and the cytoplasmic tail domain of a murine leukemia virus (MLV) envelope glycoprotein, or
  a modified BaEV envelope glycoprotein wherein the cytoplasmic tail domain is devoid of the fusion inhibitory R peptide.

Such modified MV H and F glycoproteins are described for example in Frecha et al. (2008) *Blood* 112:4843-4852 and include H glycoproteins in which the cytoplasmic tail domain is truncated of its first 15 (HΔ15), 20 (HΔ20) or 24 (HΔ24) amino acids, and F glycoproteins in which the cytoplasmic tail domain is truncated of its last 30 (FΔ30) amino acids. In a particularly preferred embodiment, the conditional pseudotyped viral vector particle of the invention further comprises modified MV HΔ24 and FΔ30 glycoproteins.

Such chimeric envelope glycoprotein and modified BaEV envelope glycoprotein is for example described in the international application WO 2013/045639.

In a particularly preferred embodiment, the conditional pseudotyped viral vector particle of the invention further comprises a modified BaEV envelope glycoprotein wherein the cytoplasmic tail domain is devoid of the fusion inhibitory R peptide, more particularly a modified BaEV envelope glycoprotein comprising or consisting of the sequence SEQ ID NO: 23.

Viral vector particles can be readily prepared by the skilled person, for example by following the general guidance provided by Sandrin al. (2002) *Blood* 100:823-832. Briefly, the viral vector particles may be generated by co-expressing the packaging elements (i.e. the core and enzyme components), the genome component and the envelope component in a so-called producer cell, e.g. 293 T human embryonic kidney cells. Typically, from three to four plasmids may be employed, but the number may be greater depending upon the degree to which the lentiviral components are broken up into separate units.

In a particularly preferred embodiment, the conditional pseudotyped viral vector particle of the invention is obtainable or obtained by the method of production described in the section "Method of production of viral vector particles" below.

Method of Production of Viral Vector Particles

The present invention also relates to a method for producing a conditional pseudotyped viral vector particle allowing physiologically-regulated expression of membrane-anchored and/or secreted antibody or chimera by B cells, comprising:
  a) transfecting a cell with
    (i) the transfer retroviral vector of the invention defined in the section "Transfer retroviral vector" above,
    (ii) a second nucleic acid comprising a cDNA encoding core proteins from the same retrovirus as the transfer retroviral vector (i), and
    (iii) a third nucleic acid comprising a cDNA encoding a viral envelope glycoprotein targeting B cells or CD34$^+$ hematopoietic stem cells,
  to yield a producer cell;
  b) maintaining the producer cell in culture for sufficient time to allow expression of the cDNAs to produce the encoded viral proteins; and
  c) allowing the encoded viral proteins to form conditional pseudotyped viral vector particles.

The "core protein from a retrovirus" refers to proteins encoded by the gag and pol genes. The gag gene encodes a polyprotein which is further processed by the retroviral protease into structural proteins that comprise the core. The pol gene encodes the retroviral protease, reverse-transcriptase, and integrase.

By "viral envelope glycoprotein targeting B cells or CD34$^+$ hematopoietic stem cells" is meant herein an viral envelope glycoprotein which mediates the transduction of B cells or CD34$^+$ hematopoietic stem cells by the virion or pseudotyped viral vector particle which bears it.

Preferably, the viral envelope glycoprotein targeting B cells or CD34$^+$ hematopoietic stem cells is a modified measles virus (MV), in particular Edmonston measles virus, hemagglutinin (H) and fusion (F) glycoproteins, wherein the cytoplasmic tail domains are truncated, a BaEV envelope glycoprotein, a chimeric envelope glycoprotein which comprises or consists in a fusion of the transmembrane and extracellular domain of a BaEV envelope glycoprotein and the cytoplasmic tail domain of a MLV envelope glycoprotein, or a modified BaEV envelope glycoprotein wherein the cytoplasmic tail domain is devoid of the fusion inhibitory R peptide. More preferably, the viral envelope glycoprotein targeting B cells or CD34$^+$ hematopoietic stem cells is a modified BaEV envelope glycoprotein wherein the cytoplasmic tail domain is devoid of the fusion inhibitory R peptide. Most preferably, the viral envelope glycoprotein targeting B cells or CD34$^+$ hematopoietic stem cells is a modified BaEV envelope glycoprotein comprising or consisting of the sequence SEQ ID NO: 23.

For the purpose of transfection, said transfer retroviral vector, second and third nucleic acid sequences may be carried on a same vector, or on two or three separated vectors. Generally, one plasmid encodes the core retroviral component of the viral vector particle. The origin of the gag and pol genes gives its name to the viral vector particle. For instance the expression "HIV-1-derived vector particle" usually indicates that the gag and pol genes of the vector particle are those of HIV-1.

The term "transfection" means the introduction of a foreign nucleic acid (DNA, cDNA or RNA) into a cell so that the host cell will express the introduced gene or sequence to produce a desired substance, typically a protein coded by the introduced gene or sequence. The introduced gene may include regulatory or control sequences, such as start, stop, promoter, signal, secretion, or other sequences used by a cell's genetic machinery. A host cell that receives and expresses introduced DNA or RNA has been "transfected".

For the production of vector particles, one may employ any cell that is compatible with the expression of retroviral, in particular lentiviral, Gag and Pol genes, or any cell that can be engineered to support such expression. For example, producer cells such as 293T cells and insect cells (in particular for HIV derived vectors), TE 671 and HT1080 cells (in particular for MLV derived vectors) may be used.

The present invention also concerns a kit comprising:
(i) the transfer retroviral vector according to the invention defined in the section "Transfer retroviral vector" above,
(ii) a second nucleic acid comprising a cDNA encoding core proteins from the same retrovirus as the retroviral vector (i), as defined above, and
(iii) a third nucleic acid comprising a cDNA encoding a viral envelope glycoprotein targeting B cells or CD34$^+$ hematopoietic stem cells, as defined above.

The kit may further include a packaging material therefor.
The vector and the two nucleic acids may be supplied in either the same or separate containers within the kit.

Packaging Cell Line

The present invention also concerns a stable virus packaging cell line producing the conditional pseudotyped viral vector particle of the invention.

In the context of the invention, a stable virus packaging cell line refers to a cell line which stably expresses the different components of the pseudotyped viral vector particle of the invention. Typically, the nucleic acids encoding the different components of the pseudotyped viral vector particle of the invention are integrated in the genome of the cell line.

In particular such stable virus packaging cell line may be any cell that is compatible with the expression of retroviral, in particular lentiviral, Gag and Pol genes, or any cell that can be engineered to support such expression. For example, they can be 293T cells, and insect cells (in particular for HIV derived vectors), TE 671 and HT1080 cells (in particular for MLV derived vectors) may be used.

Therapeutic Applications

The present invention also relates to a medicament comprising:
(i) a conditional pseudotyped viral vector particle according to the invention,
(ii) a plasmid comprising the multicistronic nucleic acid or nucleic acid according to the invention,
(iii) CD34$^+$ hematopoietic stem cells and/or B cells transduced with the conditional pseudotyped viral vector particle according to the invention, or
(iv) CD34$^+$ hematopoietic stem cells and/or B cells transfected with a plasmid comprising the multicistronic nucleic acid or nucleic acid according to the invention, as active ingredient.

It also relates to a pharmaceutical composition comprising:
(a1) a conditional pseudotyped viral vector particle according to the invention,
(a2) a plasmid comprising the multicistronic nucleic acid or nucleic acid according to the invention,
(a3) CD34$^+$ hematopoietic stem cells and/or B cells transduced with the conditional pseudotyped viral vector particle according to the invention, or
(a4) CD34$^+$ hematopoietic stem cells and/or B cells transfected with a plasmid comprising the multicistronic nucleic acid or nucleic acid according to the invention, and
(b) a pharmaceutically acceptable carrier.

The present invention also concerns a method for treating disease in a subject comprising administering a therapeutically effective amount of:
(i) a conditional pseudotyped viral vector particle according to the invention,
(ii) a plasmid comprising the multicistronic nucleic acid or nucleic acid according to the invention,
(iii) CD34$^+$ hematopoietic stem cells and/or B cells transduced with the conditional pseudotyped viral vector particle according to the invention, or
(iv) CD34$^+$ hematopoietic stem cells and/or B cells transfected with a plasmid comprising the multicistronic nucleic acid or nucleic acid according to the invention,
to the subject in need thereof.

In the context of the present invention, a "subject" denotes a human or non-human mammal, such as a rodent (rat, mouse, rabbit), a primate (chimpanzee), a feline (cat), a canine (dog). Preferably, the subject is human.

As used herein, the term "pharmaceutically acceptable carrier" refers to a carrier that may be administered to a patient, together with a conditional pseudotyped viral vector particle according to the invention, and does not destroy the pharmacological activity thereof and is non-toxic when administered in doses sufficient to deliver a pharmaceutically effective amount of the viral vector particle.

Pharmaceutically acceptable carriers and vehicles that may be used in the pharmaceutical compositions of this invention include, but are not limited to, ion exchangers, alumina, aluminium stearate, lecithin, self-emulsifying drug delivery systems (SEDDS) such as d-oc-tocopherol polyethyleneglycol 1000 succinate, surfactants used in pharmaceutical dosage forms such as Tweens or other similar polymeric delivery matrices, serum proteins, such as human serum albumin, buffer substances such as phosphates, glycine, sorbic acid, potassium sorbate, partial glyceride mixtures of saturated vegetable fatty acids, water, salts or electrolytes, such as protamine sulfate, disodium hydrogen phosphate, potassium hydrogen phosphate, sodium chloride, zinc salts, colloidal silica, magnesium trisilicate, polyvinyl pyrrolidone, cellulose-based substances, polyethylene glycol, sodium carboxymethylcellulose, polyacrylates, waxes, polyethylene-polyoxypropylene-block polymers, polyethylene glycol and wool fat. Cyclodextrins such as $\alpha$-, $\beta$-, and $\gamma$-cyclodextrin, or chemically modified derivatives such as hydroxyalkylcyclodextrins, including 2- and 3-hydroxypropyl-cyclodextrins, or other solubilized derivatives may also be advantageously used to enhance delivery of compositions according to the invention.

Any suitable method of administration known from one skilled in the art may be used. In particular, the pseudotyped viral vector particle according to the invention or the transduced or transfected cells may be administered for example by the parenteral route (in particular by intravenous injection and intra-femur (bone marrow cavity) injection). When the parenteral route is selected, the pseudotyped viral vector particles may be in the form of injectable solutions and suspensions, conditioned in ampoules or flasks. The forms for parenteral delivery are conventionally obtained by mixing the pseudotyped viral vector particles according to the invention with buffers, stabilizers, preservatives, solubilizing agents, isotonic agents and slurrying agents. According to known techniques, these mixtures can then be sterilized and conditioned in the form of intravenous injections. One of skill in the art may use organic phosphate salts-based buffers as buffer. Examples of slurrying agents include methylcellulose, acacia and sodium carboxymethylcellulose. Examples of stabilizers include sodium sulphite and sodium metasulphite, and examples of preservatives include sodium p-hydroxybenzoate, sorbic acid, cresol and chlorocresol.

The plasmid comprising the multicistronic nucleic acid or nucleic acid according to the invention may typically be administered by electroporation, in particular after linearization.

The present invention also relates to a vaccine composition comprising:
(a1) a conditional pseudotyped viral vector particle according to the invention,
(a2) a plasmid comprising the multicistronic nucleic acid according to the invention,
(a3) CD34$^+$ hematopoietic stem cells and/or B cells transduced with the conditional pseudotyped viral vector particle according to the invention, or
(a4) CD34$^+$ hematopoietic stem cells and/or B cells transfected with a plasmid comprising the multicistronic nucleic acid according to the invention, and (b) a pharmaceutically acceptable carrier. The vaccine composition of the invention may further comprise an adjuvant.

The present invention further concerns the conditional pseudotyped viral vector particle according to the invention, a plasmid comprising the multicistronic nucleic acid according to the invention, CD34$^+$ hematopoietic stem cells and/or B cells transduced with the conditional pseudotyped viral vector particle according to the invention, or CD34$^+$ hematopoietic stem cells and/or B cells transfected with a plasmid comprising the multicistronic nucleic acid according to the invention, for use as a vaccine.

It also concerns a method of vaccination of a subject comprising administering in a subject in need thereof a prophylactically effective amount of:
(i) the conditional pseudotyped viral vector particle according to the invention,
(ii) a plasmid comprising the multicistronic nucleic acid according to the invention,
(iii) CD34$^+$ hematopoietic stem cells and/or B cells transduced with the conditional pseudotyped viral vector particle according to the invention, or
(iv) CD34$^+$ hematopoietic stem cells and/or B cells transfected with a plasmid comprising the multicistronic nucleic acid according to the invention.

The present invention further concerns the conditional pseudotyped viral vector particle of the invention, a plasmid comprising the multicistronic nucleic acid according to the invention, CD34$^+$ hematopoietic stem cells and/or B cells transduced with the conditional pseudotyped viral vector particle according to the invention, or CD34$^+$ hematopoietic stem cells and/or B cells transfected with a plasmid comprising the multicistronic nucleic acid according to the invention, for use as a vectored immunoprophylaxis medicament.

It further concerns the use of the conditional pseudotyped viral vector particle of the invention, a plasmid comprising the multicistronic nucleic acid according to the invention, CD34$^+$ hematopoietic stem cells and/or B cells transduced with the conditional pseudotyped viral vector particle according to the invention, or CD34$^+$ hematopoietic stem cells and/or B cells transfected with a plasmid comprising the multicistronic nucleic acid according to the invention, for the manufacture of a medicament intended for vectored immunoprophylaxis.

The present invention also concerns a method of providing vectored immunoprophylaxis to a subject, comprising administering to said subject a therapeutically effective amount of the conditional pseudotyped viral vector particle of the invention, a plasmid comprising the multicistronic nucleic acid according to the invention, CD34$^+$ hematopoietic stem cells and/or B cells transduced with the conditional pseudotyped viral vector particle according to the invention, or CD34$^+$ hematopoietic stem cells and/or B cells transfected with a plasmid comprising the multicistronic nucleic acid according to the invention.

A "therapeutically effective amount" refers to a quantity of a viral vector particle that confers a therapeutic effect on the treated subject. A "prophylactically effective amount" refers to a quantity of a viral vector particle that confers a prophylactic effect on the treated subject. The therapeutic or prophylactic effect may be objective (i.e., measurable by some test or marker) or subjective (i.e., subject gives an indication of or feels an effect). As known from the skilled person, effective doses will vary depending on route of administration, the size and/or weight of the subject, as well as the possibility of co-usage with other agents.

Where the pseudotyped viral vector particle is used as a medicament and is administered to a subject in a therapeutic method, administration through the intravenous route or by the medullar route, in particular the femur or humerus medullar route, is preferred.

In a particular embodiment, the conditional pseudotyped viral vector particle of the invention, the plasmid comprising the multicistronic nucleic acid or nucleic acid according to the invention, CD34$^+$ hematopoietic stem cells and/or B cells transduced with the conditional pseudotyped viral vector particle according to the invention, or CD34$^+$ hematopoietic stem cells and/or B cells transfected with a plasmid comprising the multicistronic nucleic acid or nucleic acid according to the invention, is for use for treating and/or preventing an infectious disease, an inflammatory disease or a cancer.

The invention also relates to the use of the conditional pseudotyped viral vector particle of the invention, a plasmid comprising the multicistronic nucleic acid or nucleic acid according to the invention, CD34+ hematopoietic stem cells and/or B cells transduced with the conditional pseudotyped viral vector particle according to the invention, or CD34+ hematopoietic stem cells and/or B cells transfected with a plasmid comprising the multicistronic nucleic acid or nucleic acid according to the invention, for the manufacture of a medicament intended for the treatment and/or the prevention of an infectious disease, an inflammatory disease or a cancer. It further relates to a method for treating and/or preventing an infectious disease, an inflammatory disease or a cancer in a subject, comprising administering a prophylactically or therapeutically effective amount of the conditional pseudotyped viral vector particle of the invention, a plasmid comprising the multicistronic nucleic acid or nucleic acid according to the invention, CD34+ hematopoietic stem cells and/or B cells transduced with the conditional pseudotyped viral vector particle according to the invention, or CD34+ hematopoietic stem cells and/or B cells transfected with a plasmid comprising the multicistronic nucleic acid or nucleic acid according to the invention, in a subject in need thereof.

As used herein, the term "infectious disease" refers to a condition in which an infectious organism or agent is present in a detectable amount in the blood or in a normally sterile tissue or normally sterile compartment of a subject. Infectious organisms and agents include viruses, mycobacteria, bacteria, fungi, and parasites. The terms encompass both acute and chronic infections, as well as sepsis.

As used herein, the term "cancer" refers to a condition in which abnormally replicating cells of host origin are present in a detectable amount in a subject. The cancer can be a malignant or non-malignant cancer. Cancers include, but are not limited to, biliary tract cancer; brain cancer; breast cancer; cervical cancer; choriocarcinoma; colon cancer; endometrial cancer; esophageal cancer; gastric cancer; intraepithelial neoplasms; leukemias; lymphomas; liver cancer; lung cancer; melanoma; neuroblastomas; oral cancer; ovarian cancer; pancreatic cancer; prostate cancer; rectal cancer; renal cancer; sarcomas; skin cancer; testicular cancer; thyroid cancer; as well as other carcinomas and sarcomas. Cancers can be primary or metastatic.

The antibody of interest encoded by the multicistronic nucleic acid included in the conditional pseudotyped viral vector particle of the invention will depend on the infectious disease or cancer to be treated or prevented. Such antibodies of interest are well-known from the skilled person.

Transducing and Transfecting Methods

The present invention also relates to the use of the conditional pseudotyped viral vector particle according to the invention or of a plasmid comprising the multicistronic nucleic acid or nucleic acid according to the invention to induce the physiologically-regulated expression of the membrane-anchored and/or secreted antibody or chimera of interest by a B cell, as defined above, ex vivo.

In a preferred embodiment, the expression of the membrane-anchored form of the antibody or chimera of interest is induced when the B cell is a BCR-expressing B cell.

In another preferred embodiment, the expression of the secreted form of the antibody or chimera of interest is induced when the B cell is a plasma-cell like B cell.

The present invention will be further illustrated by the figures and examples below.

LTR: long terminal repeats; F: HIV-1 flap element; WRE: woodchuck hepatitis virus posttranscriptional regulatory element. SA and SD: splicing acceptor and donor site, respectively. pAS and pAM: polyAdenylation sequence for the secreted and membrane-anchored forms, respectively.

Figure 2:
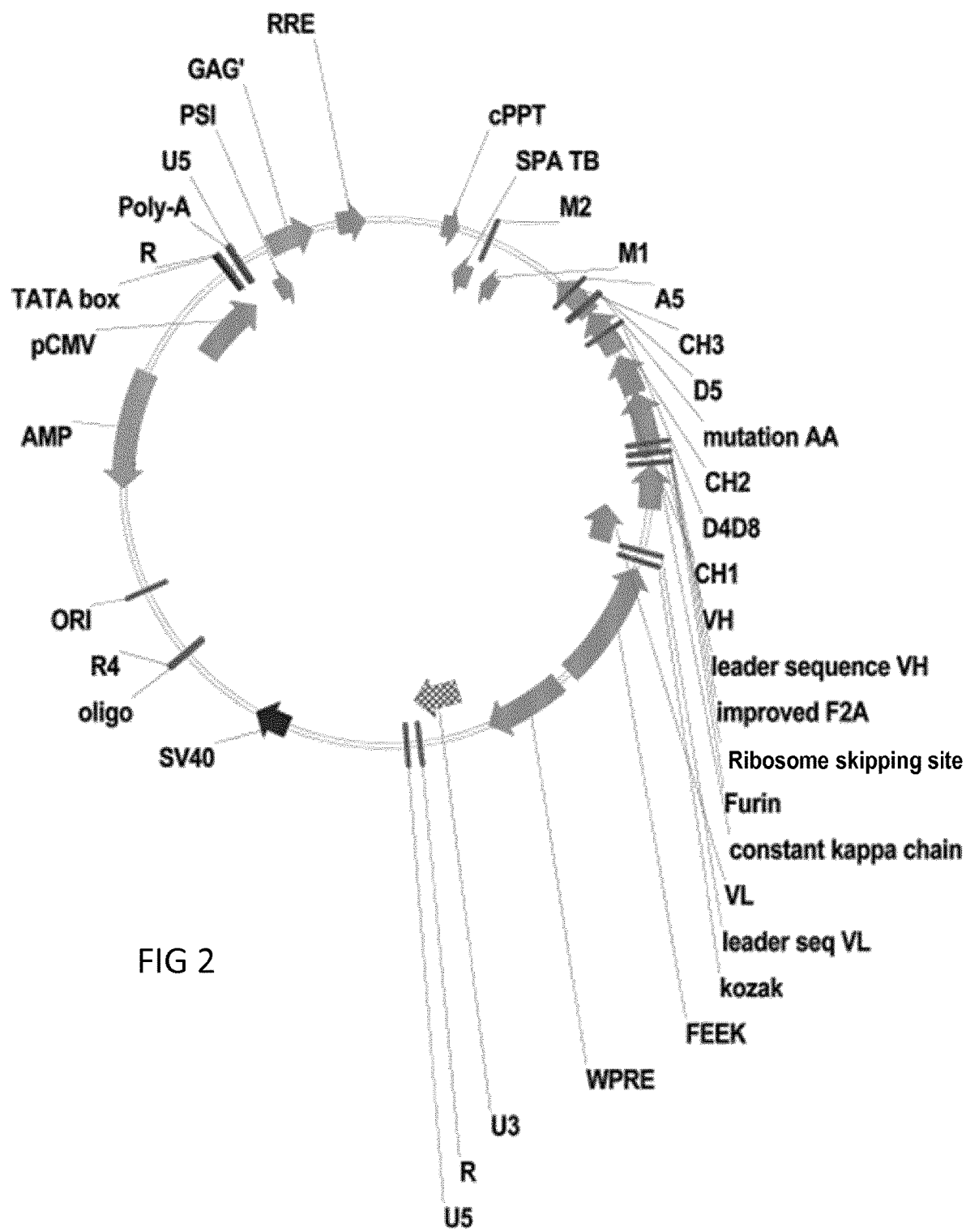

FIG. 2: plasmid card of the FAM1 vector described in the example.

Figure 3:
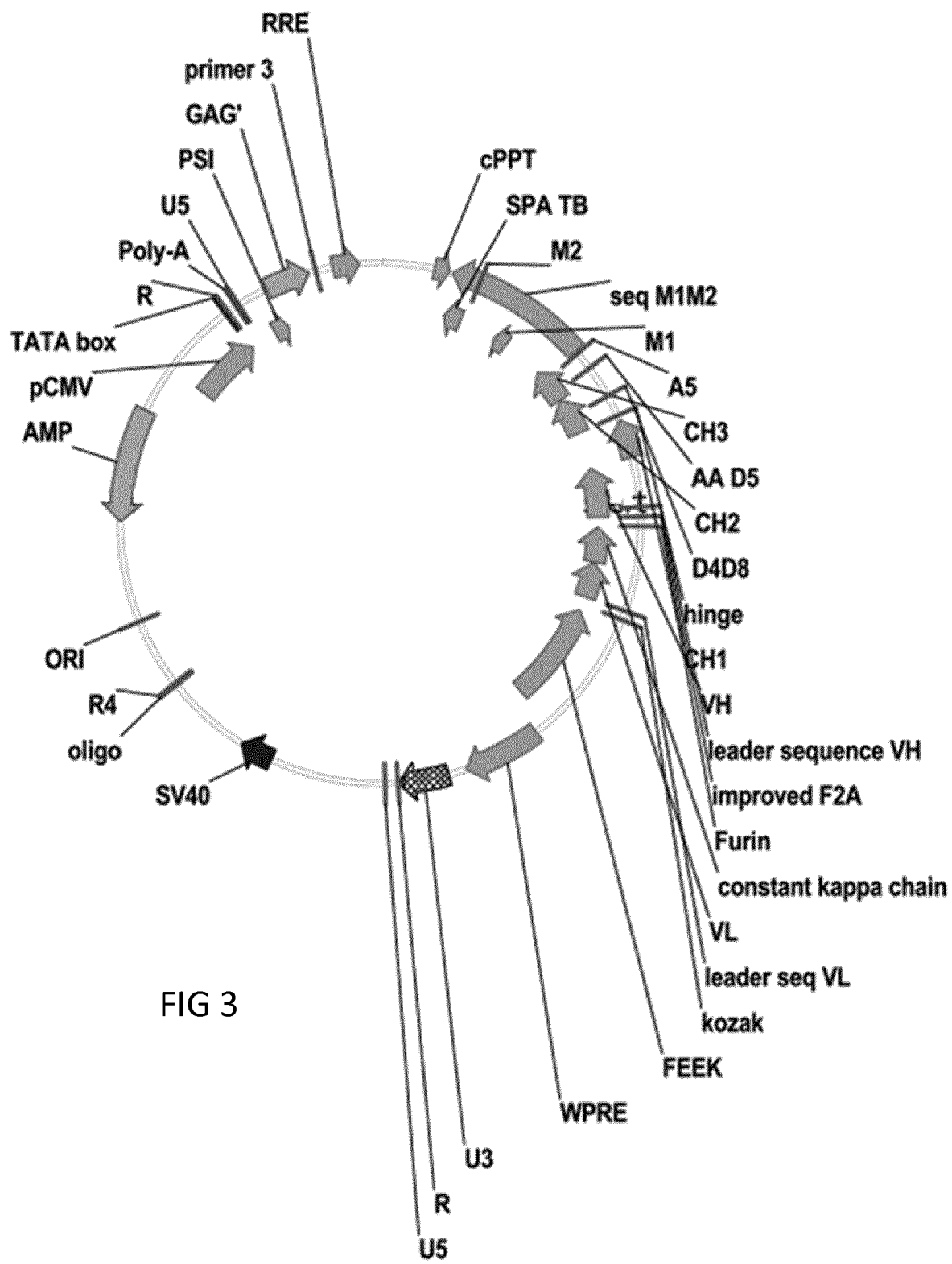

FIG. 3: plasmid card of the FAM2 vector described in the example.

Figure 4:
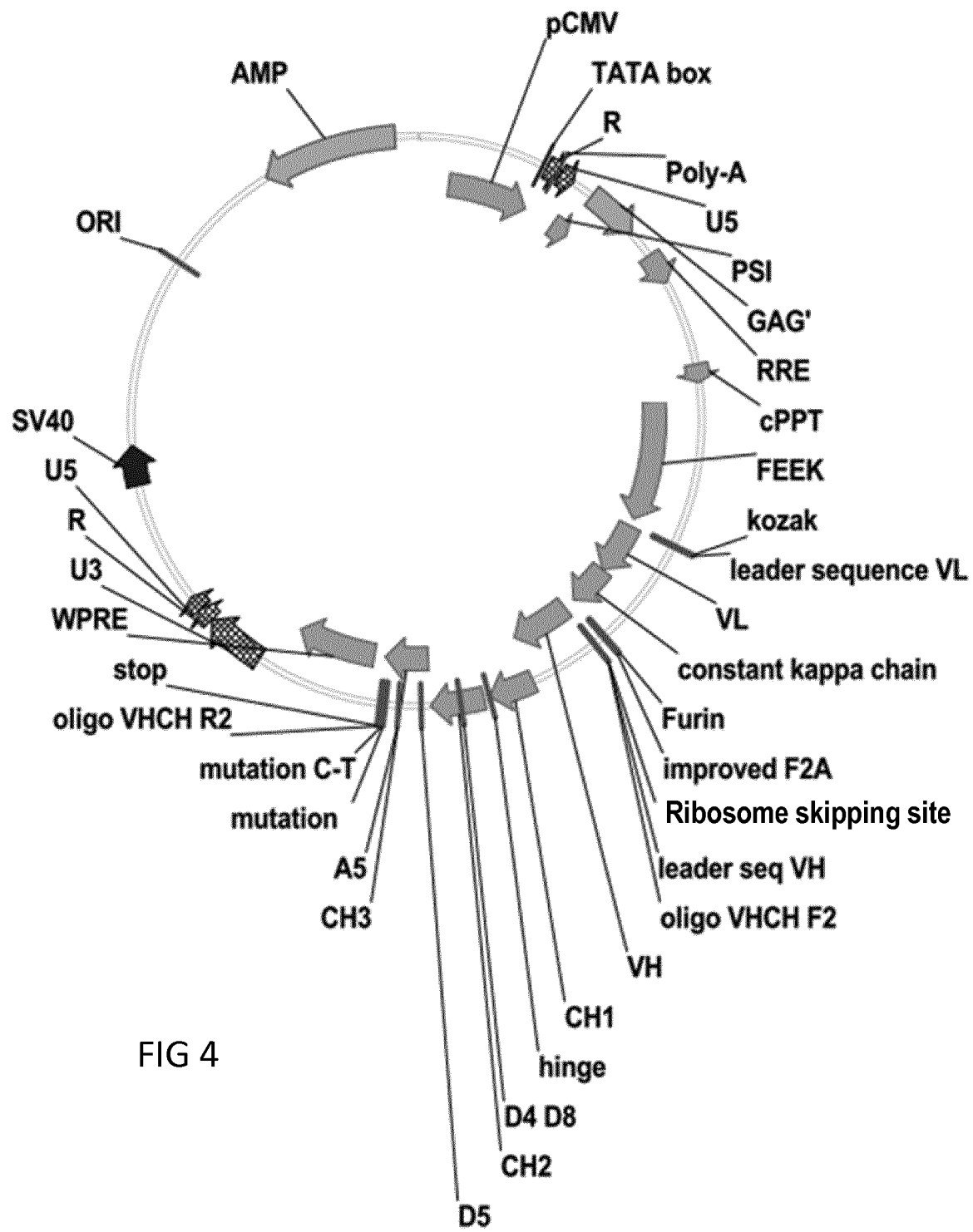

FIG. 4: plasmid card of the FSS vector described in the example.

Figure 5:
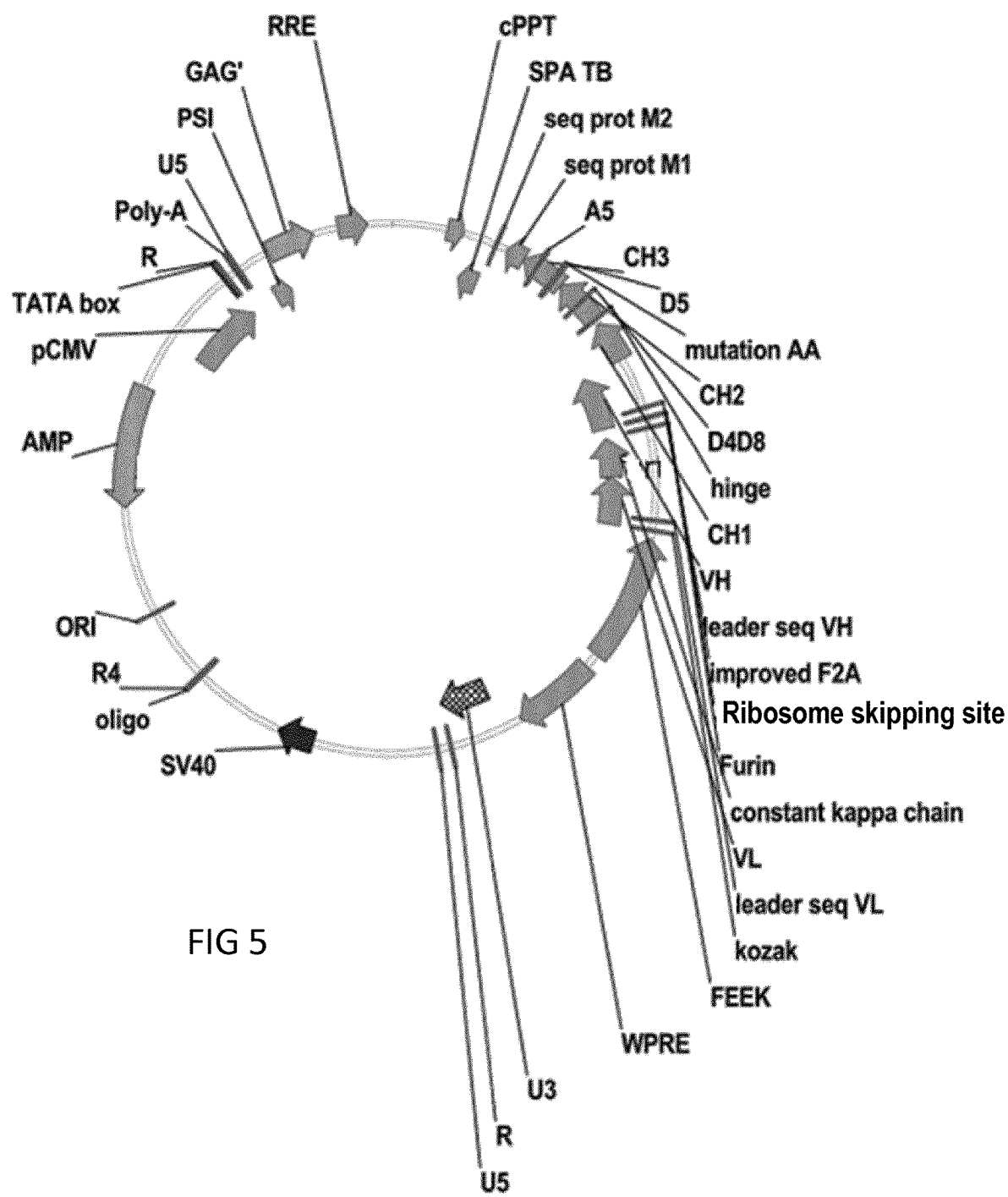

FIG. 5: plasmid card of the FAM0 vector described in the example.

Figure 6:
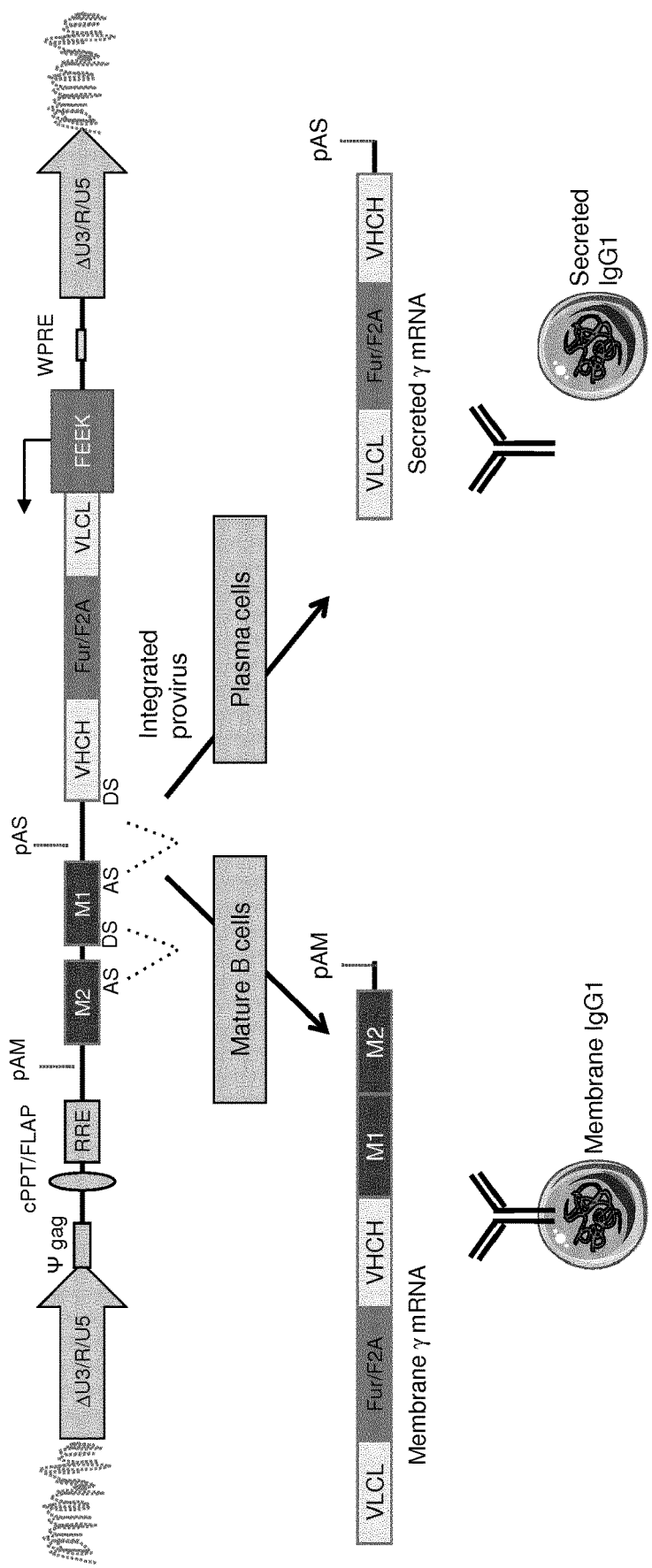

FIG. 6: Conditional LVs for AR3A antibody production mimicking the natural expression of the two distinct immunoglobulin (Ig) forms which is tightly controlled by alternative splicing and polyadenylation mechanisms during B cell lymphopoïesis.

FIGS. 7-10: Evaluation of the transgenic IgG1 anti-E2 antibody expression in the non-secreting Namalwa Burkitt lymphoma (BL) cell line.

Figure 7:
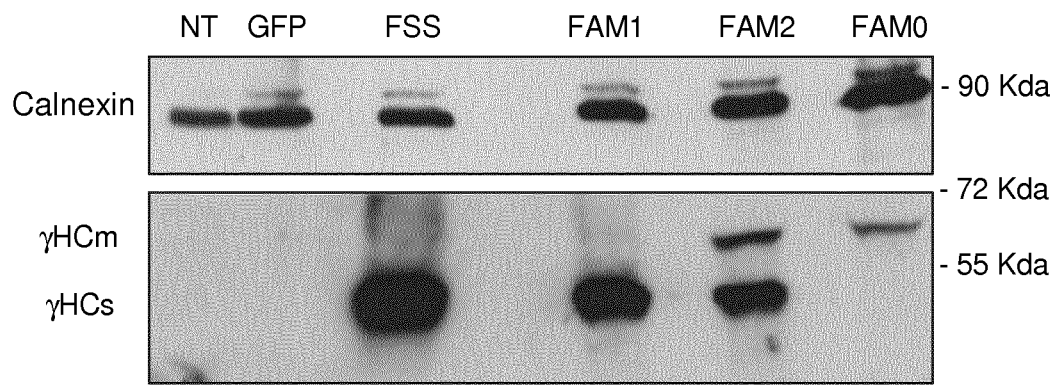
Figure 8:
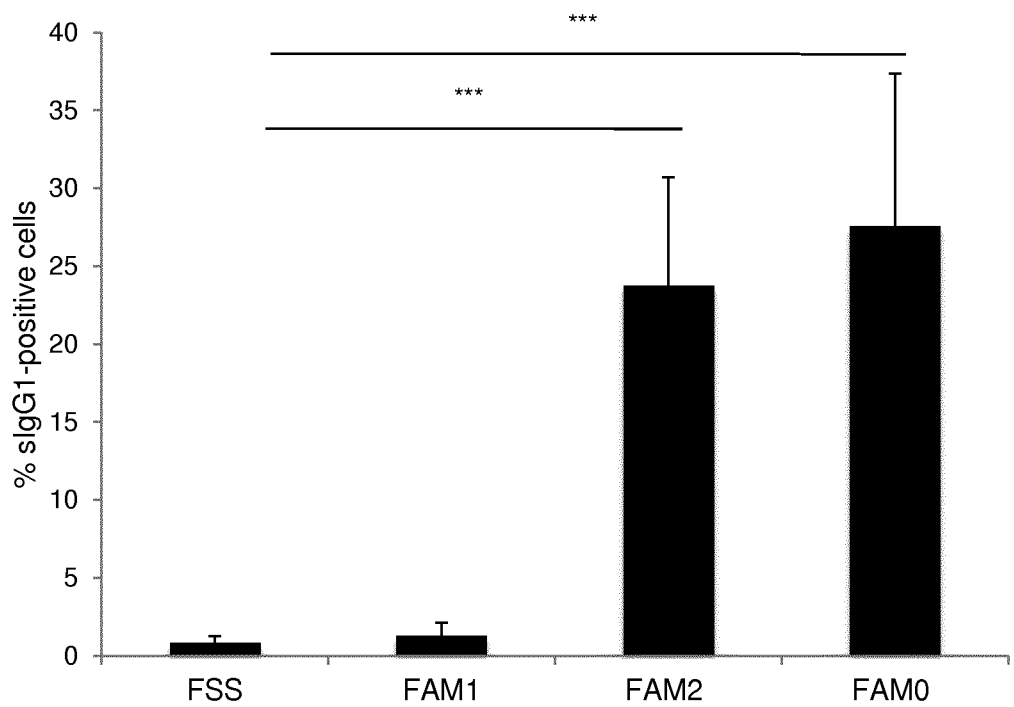

Namalwa B cells were transduced with each of the four LVs as indicated at MOI of 10 to 20 and harvested 5 days post-transduction for western blot analysis (FIG. 7) and the expression of the membrane-bound IgG1 form (FIG. 10 and FIG. 9) and the secreted form of the AR3A antibody (FIG. 8).

FIG. 7—Whole cell lysates were analyzed by Western Blot. Proteins were separated in SDS-PAGE under reducing conditions and probed with a goat anti-human IgG (H+L) polyclonal antibody and anti-calnexin. HCm: Membrane-form of the IgG1 HC. HCs: secreted form of the IgG1 HC. The approximate sizes of the various heavy chain isovariants are indicated.

FIG. 8—The percentage of surface γ1 HC (sIgG1) expressing cells were determined by FACS analysis (intracellular LC Igκ+ gating) (means±standard deviation [SD], n≥9; *** P≤0.001).

Figure 9:
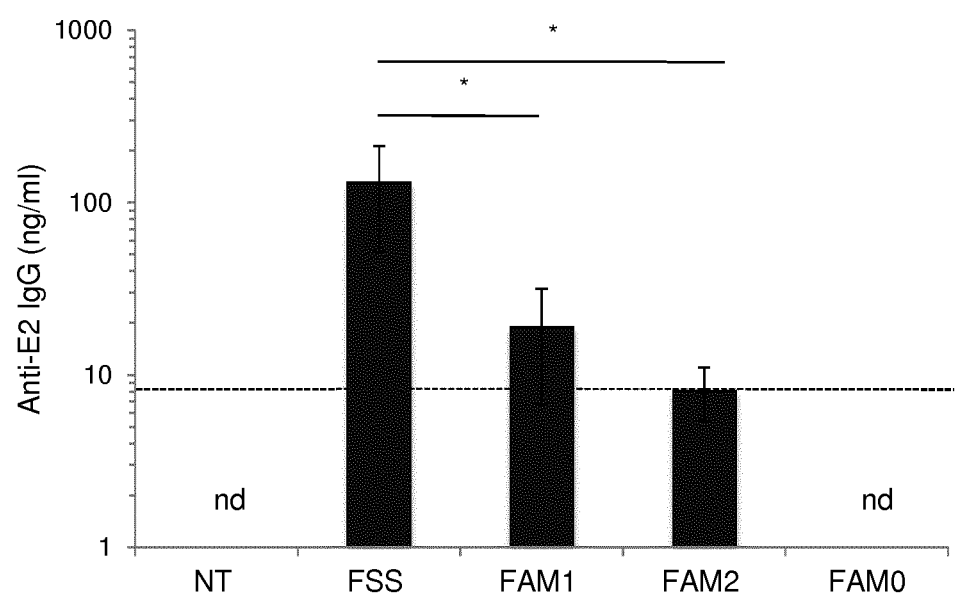

FIG. 9—Levels of secreted anti-E2-specific IgGs in culture supernatants quantified by specific anti-E2 ELISA. The anti-E2 IgG1 secretion in B cells transduced with the GFP and FAM0 construct was consistently not detectable (nd) (means±SD, n≥3; *P≤0.05).

Figure 10:
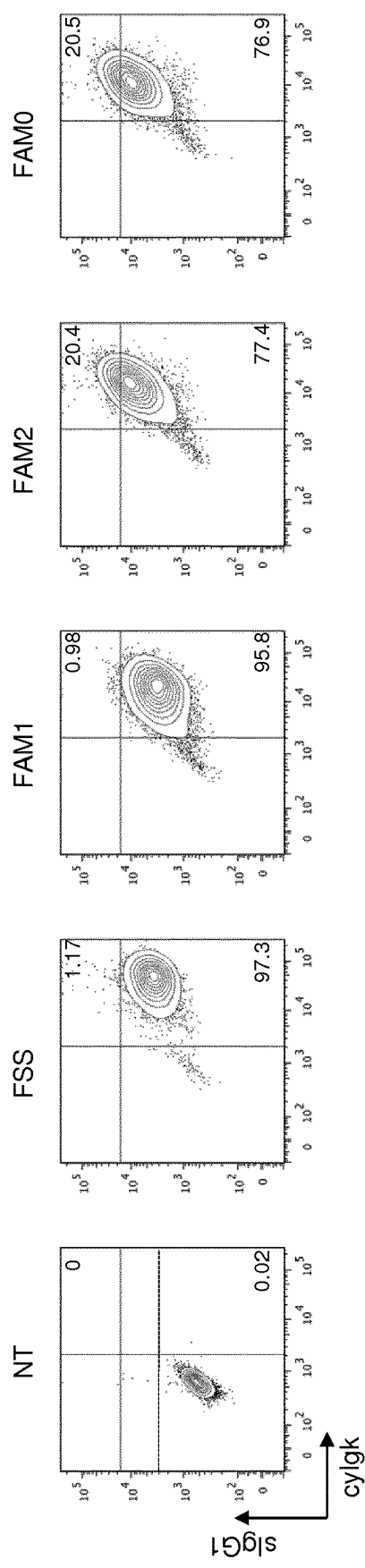

FIG. 10—Flow cytometry analysis of transduced BL cells for intracellular and surface expression of anti-E2 antibody. Since the population FSS probably shows binding of the soluble form to the FcR CD32 (shown on the FIG. 7 where the FSS transduced cells do not produce the 62 KDa band of the membrane-form of IgG1), the effective gate was shifted taking into account this background surface staining on FSS as negative control to clearly reveal the BCR membrane form (sIgG1: membrane staining of the IgG1 HC; cyκ: intracellular staining of the k LC).

Figure 11:
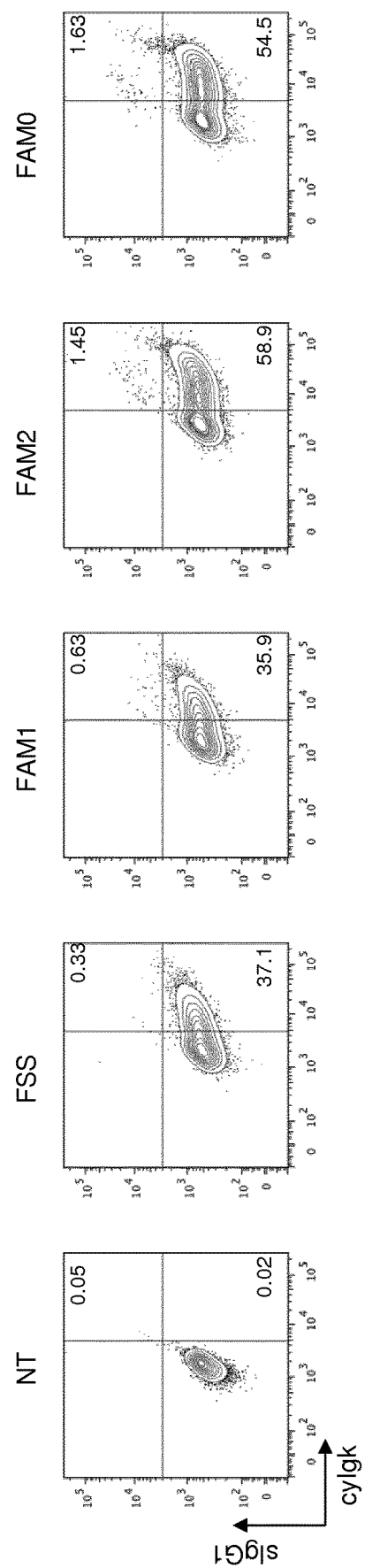
Figure 12:
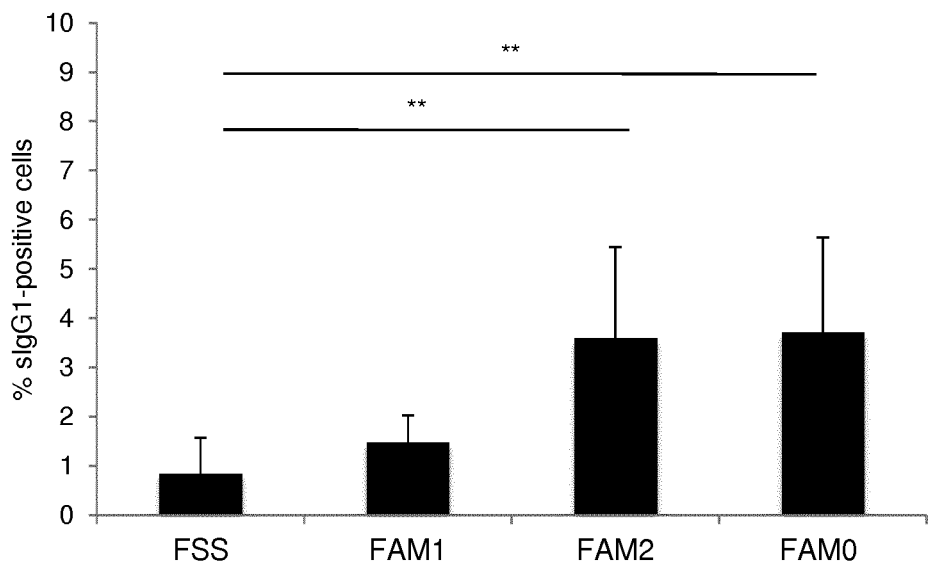
Figure 13:
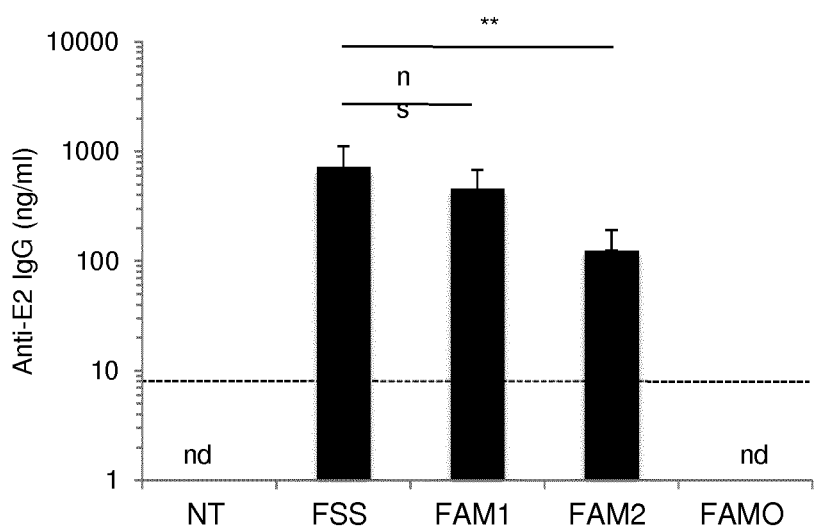

FIGS. 11-13: Evaluation of the transgenic IgG1 anti-E2 antibody expression in the U266 plasmocytic B cell line.

Human plasmocytoma U266 cells were transduced the indicated LVs pseudotyped with VSV-G at MOI of 10 to 20 and harvested 5 days post-transduction for analysis.

FIG. 11: Flow cytometry analysis of transduced U266 cells for intracellular and surface expression of anti-E2 antibody (sIgG1: membrane staining of the IgG1 HC; cyκ: intracellular staining of the k LC).

FIG. 12: Statistical analysis of the percentages of γ1 HC (sIgG1) expressing cells as determined by FACS analysis (intracellular LC Igκ+ gating) (means±SD, n=7; **P≤0.01).

FIG. 13: Levels of secreted anti-E2-specific IgGs in culture supernatants were quantified by specific anti-E2 ELISA (normalization for 100% transduction and cell number). The anti-E2 IgG1 secretion in B cells transduced with the GFP and FAM0 construct was consistently not detectable (nd) (means±SD, n≥6; **P≤0.01).

FIGS. 14-17: Expression of the membrane-bound form of the transgenic IgG1 anti-E2 antibody slightly affects the pattern of the endogenous IgM surface expression.

Figure 14:
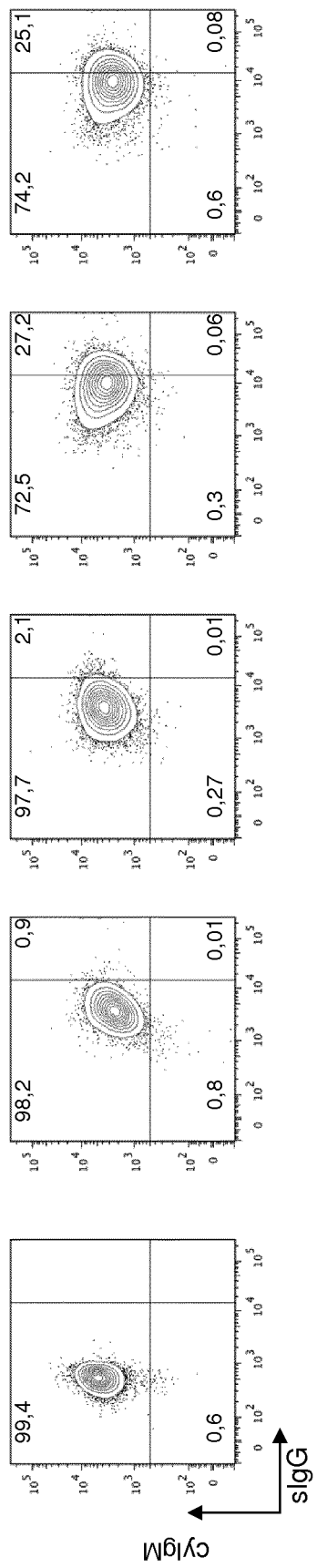

FIG. 14: FACS analysis of endogenous IgM at the intracellular level (cyIgM) and transgenic γ1 HC expression at the cell surface (sIgG1) of transduced (intracellular LC Igκ+ gating) Namalwa cells.

Figure 15:
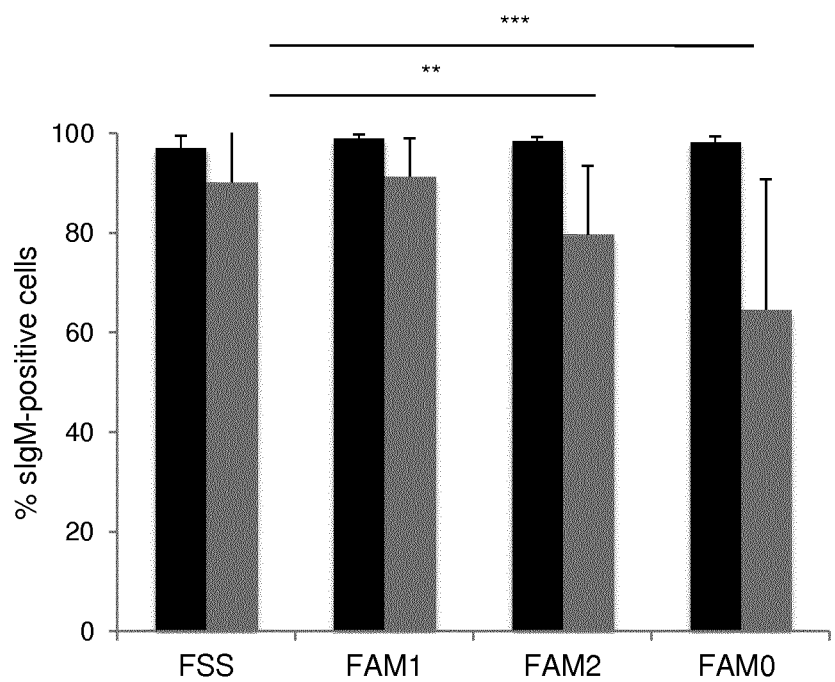

FIG. 15: Percentage of the intracellular endogenous IgM (cyIgM) (black bars, n≥16) and membrane-anchored endogenous IgM (sIgM) (grey bars, n≥10) (means±SD,  P≤0.01; * P≤0.001).

Figure 16:
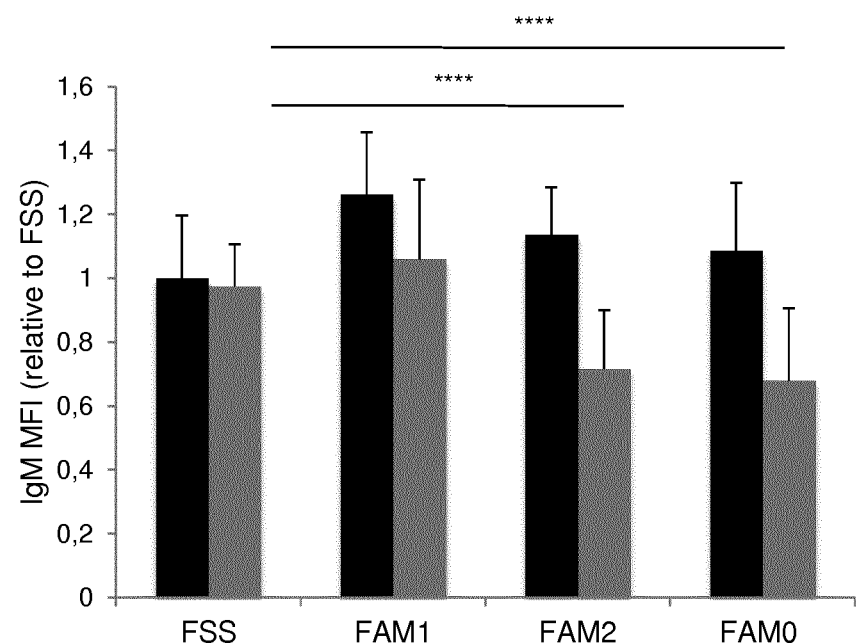

FIG. 16: Expression levels (MFI) of the intracellular endogenous IgM (cyIgM) (black bars, n≥7) and membrane-anchored endogenous IgM (sIgM) (grey bars, n≥13), relative to the FSS values for which MFI was set to 1 (means±SD, ****P≤0.0001).

Figure 17:
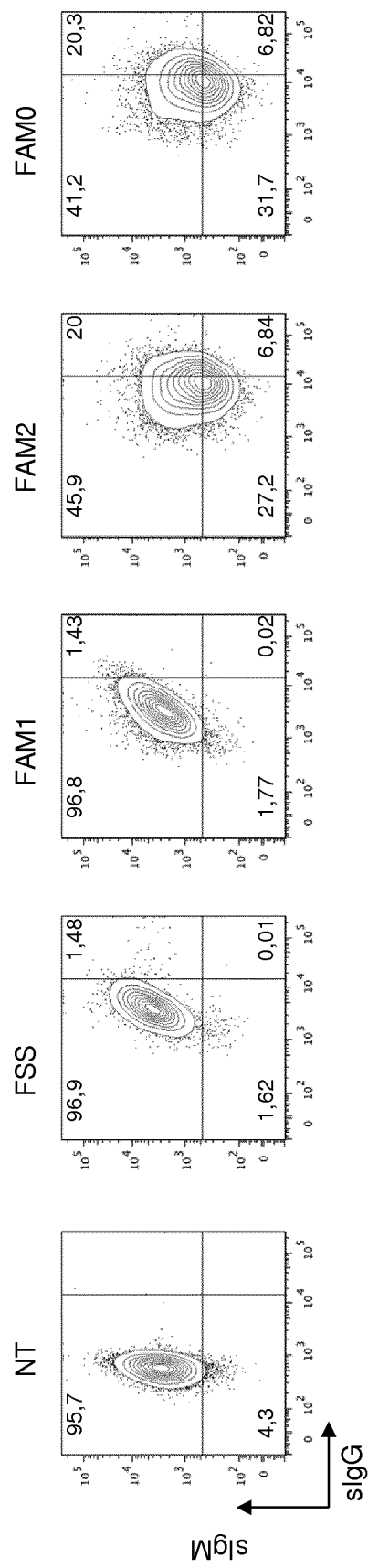

FIG. 17: FACS analysis of endogenous IgM (sIgM) and transgenic γ1 HC (sIgG1) expression at the cell surface for transduced (intracellular LC κ+ gating) Namalwa cells.

Since the population FSS showed staining for the membrane HC form although the FSS transduced cells do not produce the 62 KDa band of the membrane-form of γ1 HC the effective gate was shifted on FSS as negative control to clearly reveal the BCR membrane form.

Figure 18:
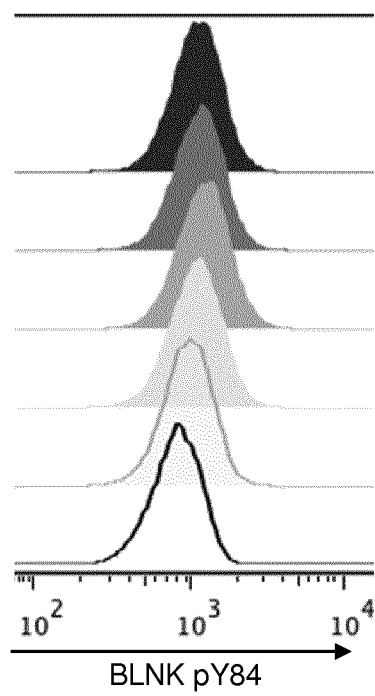
Figure 19:
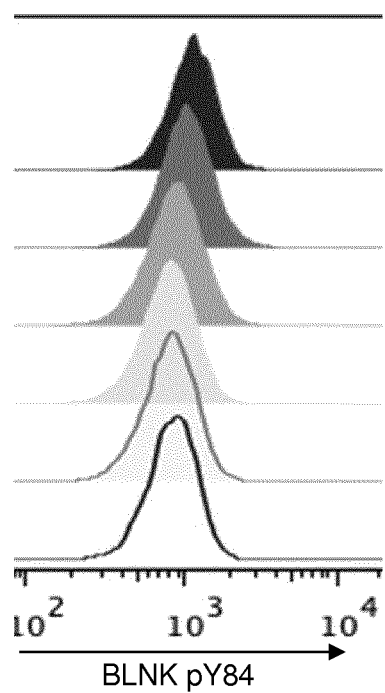
Figure 20:
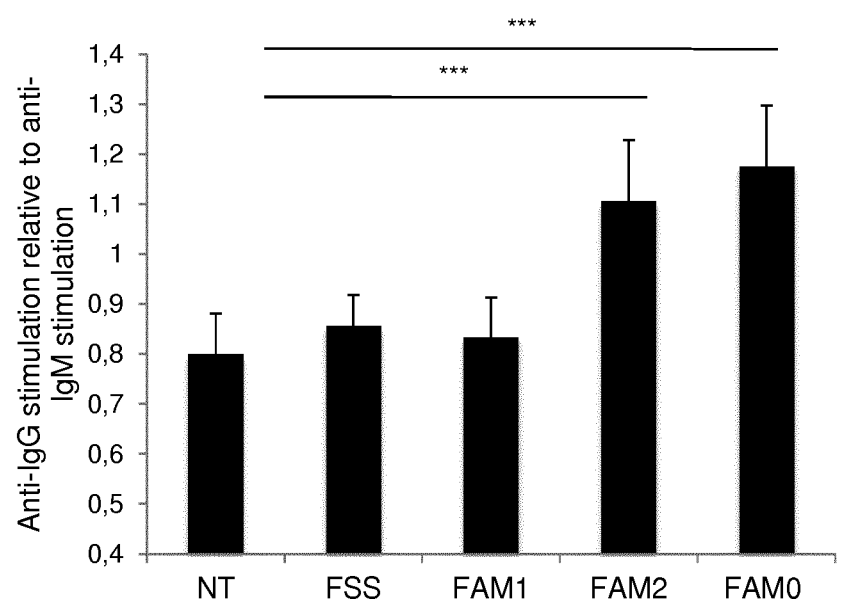

FIGS. 18-20: Functionality of the transgenic BCR after polyclonal stimulation/Contrasting IgM and IgG BCR signaling.

Transduced cells were stimulated by anti-μ (FIG. 18) or anti-γ (FIG. 19) BCR cross-linking using either anti-IgM (endogenous BCR in a) or anti-IgG (Fab')2 (ectopic BCR in FIG. 19) and compared with unstimulated cells. The level of BLNK-Y84 phosphorylation is shown for cells positive for intracellular kappa staining.

FIG. 20: Stimulation was determined by the increase in MFI of stimulated samples relative to unstimulated and the ratio γ/μ was determined (means±SD, n≥4; *** P≤0.001).

Figure 21:
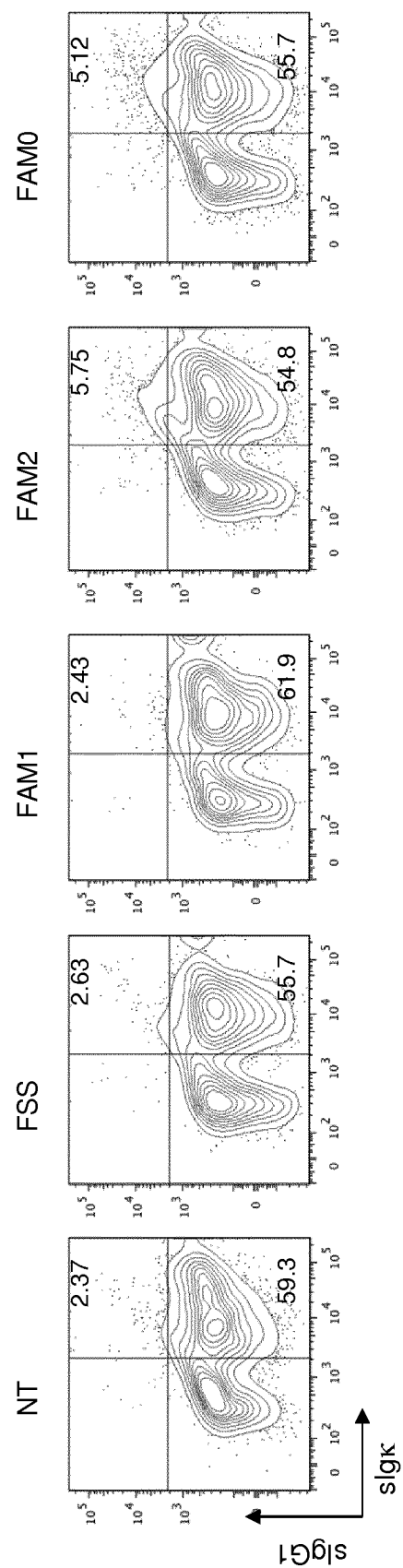
Figure 22:
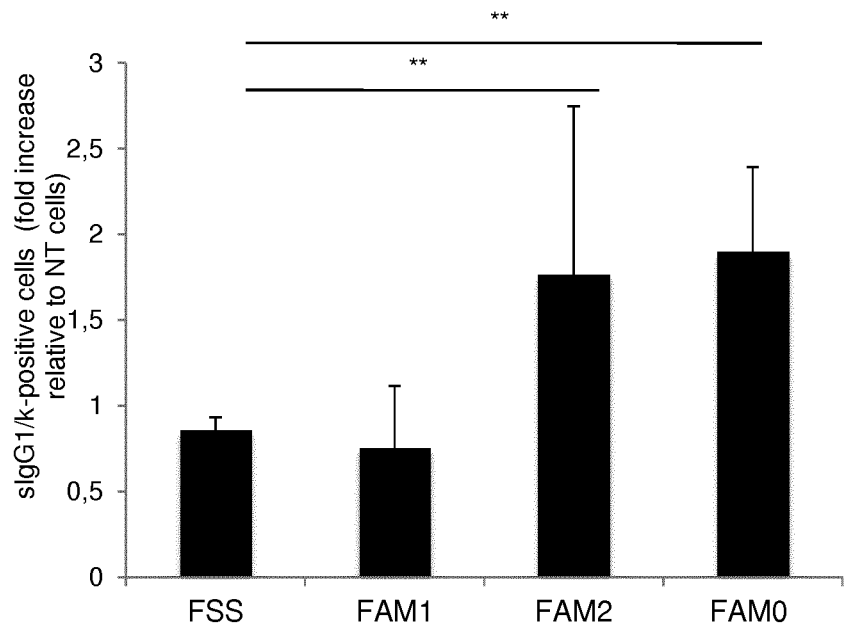
Figure 23:
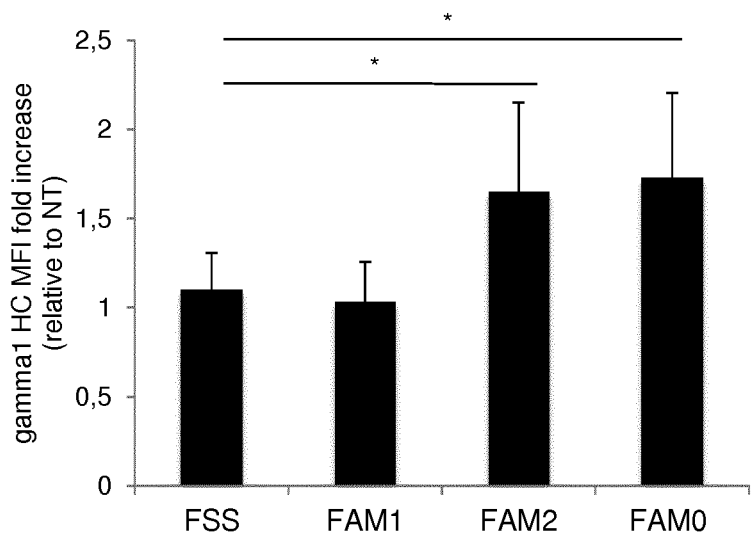

FIGS. 21-23: In vitro expression of the transgenic AR3A antibody in primary B cells. CD19+ B cells were purified from peripheral adult blood and transduced at MOI 10-15 with BAEV gp pseudotyped LVs in the presence of IL2 and pansorbin on retronectin coated wells. At day 3, cells were washed and co-cultured on MS5 in the presence of IL-2 and IL-15. Seven days post-transduction culture supernatants were collected and the cells were analyzed by flow cytometry for expression of IgG1/κ.

FIG. 21: Surface γ1 HC (sIgG1) and κ LC (staining of transduced primary CD19+ B cells analyzed by flow cytometry at day 7 post-transduction (shown as fold increase compared to non-transduced cells; data are representative of 3 experiments)

FIG. 22: Surface expression of γ1 HC (sIgG1) and κ LC on B cells (shown as fold increase compared to non-transduced cells (means±SD, n≥4; ** P≤0.01).

FIG. 23: Levels of expression of membrane-anchored γ1 HC (sIgG1) on transduced cells as expressed by fold increase in MFI as compared to non-transduced cells (means±SD, n≥4; * P≤0.05).

FIGS. 24-27: In vivo expression of the transgenic AR3A antibody in humanized mice. 7-weeks old NSG Mice were engrafted by IP injection of 4 $10^6$ CD4+ cells and 3 $10^6$ CD19+ cells transduced either with a GFP-encoding vector, FSS, FAM2 or FAM2 vector. The serum AR3A IgG1 levels were measured weekly starting from day 7 post-reconstitution.

Figure 24:
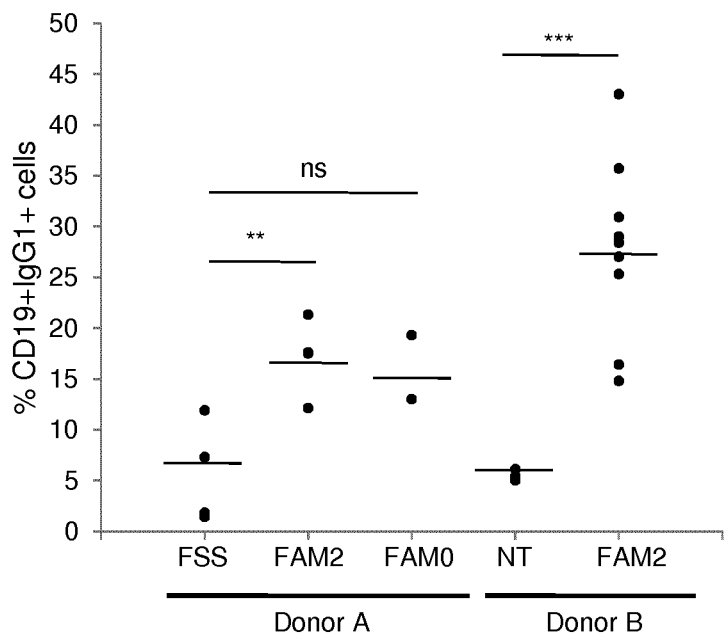

FIG. 24: Splenic human B cells (CD45+CD19+) were assessed for surface IgG1 expression.

Figure 25:
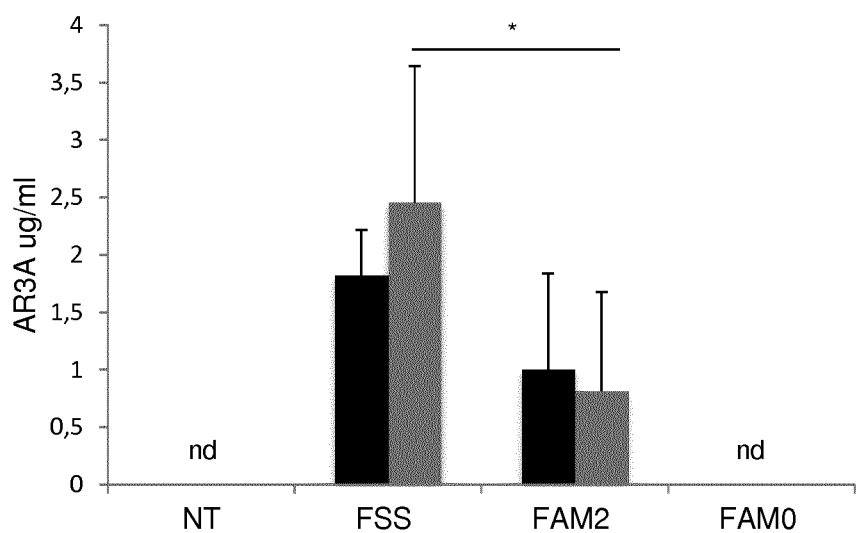

FIG. 25: Kinetics of the anti-E2 human IgG1 serum antibody production in humanized mice. The results expressed in μg/ml represent the Mean/SD of the experimental values gathered from 4 to 8 humanized mice depending on the group (P≤0.01; *P≤0.001). The anti-E2 hIgG1 production in mice reconstituted by B cells transduced with the GFP and FAM0 construct was consistently undetectable (nd) (d14: black bars, d21: grey bars).

Figure 26:
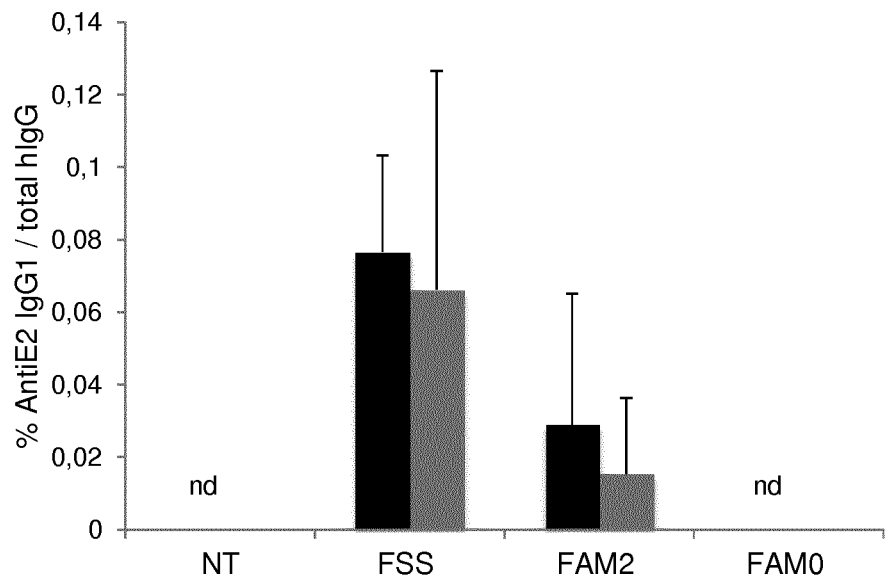

FIG. 26: Determination of the percentage of anti E2 hIgG/human IgG in mouse sera (d14: black bars, d21: grey bars) (means±SD, *P≤0.05).

Figure 27:
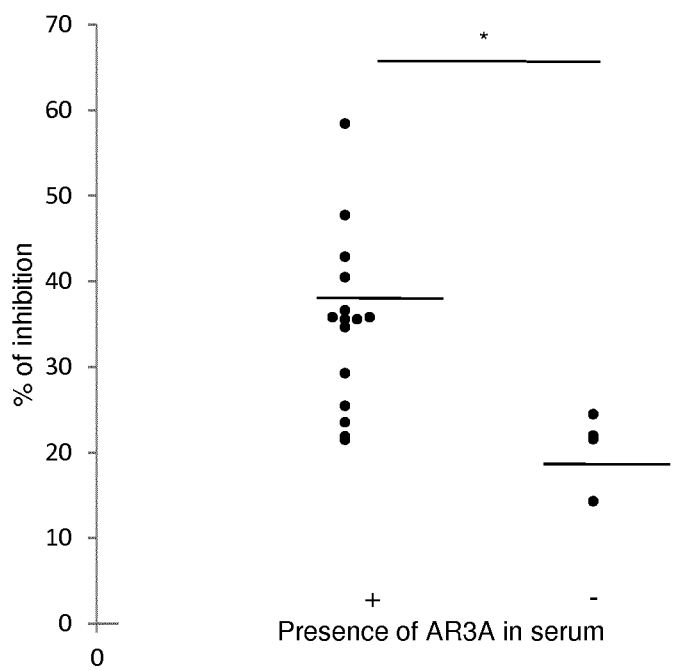

FIG. 27: Mouse sera were used for neutralization assays with HCVcc on HuH7 cell line. HCVcc particles were incubated with mouse sera during 1 h at 37° C. before HuH7 infection. Cells were wash 6 h later then subcultured during 5 days (means±SD, n≥6; *P=0.02).

Figure 28:
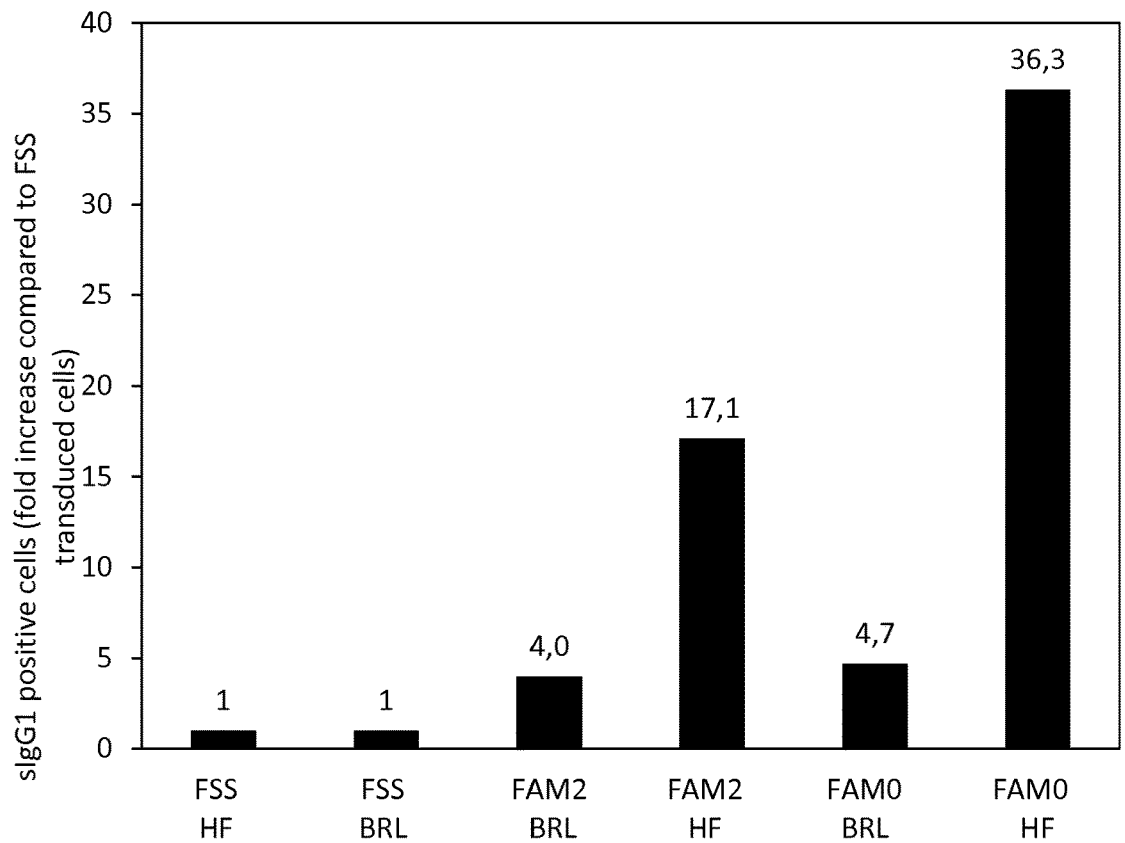
Figure 29:
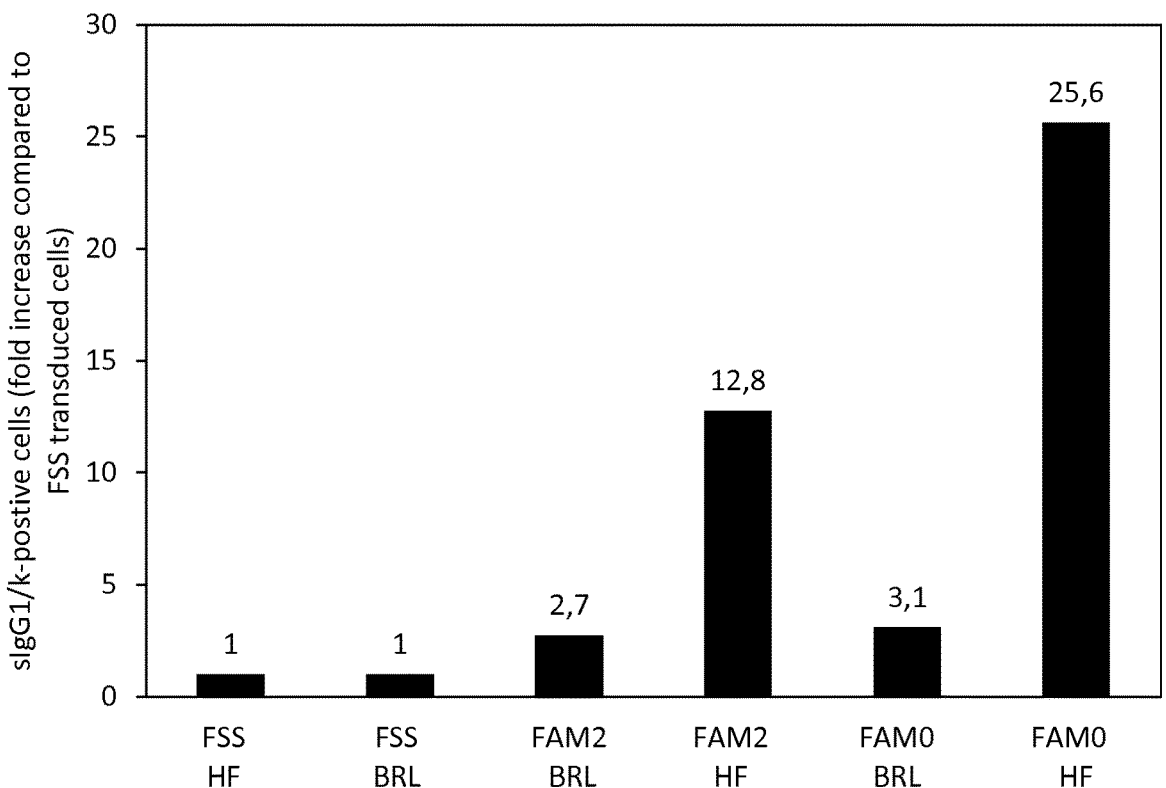

FIGS. 28-30: In vitro expression of the transgenic AR3A antibody in primary B cells transduced with lentiviral vectors pseudotyped with the glycoproteins from measles virus or Baboon endogenous virus (BaEV). CD19+ B cells were purified from peripheral adult blood and transduced at MOI 10-15 with BAEV gp (BRL) pseudotyped LVs or at MOI 1-10 with the measles virus gp (HF) pseudotyped LVs (FSS, FAM2, FAM0), in the presence of IL2 and pansorbin cultured on retronectin-coated wells. At day 3, cells were washed and co-cultured on MS5 cells in the presence of IL-2 and IL-15. Seven days post-transduction culture supernatants were collected and the cells were analyzed by flow cytometry for expression of IgG1/K.

FIG. 28: Surface expression of γ1 HC (sIgG1) (gated on CD19+ cells) shown as fold increase compared to FSS-transduced cells.

FIG. 29: Surface expression of γ1 HC (sIgG1) and κ LC on B cells shown as fold increase compared to FSS-transduced cells.

FIG. 30: Surface γ1 HC (sIgG1) staining of transduced primary CD19+ B cells analyzed by flow cytometry at day 7 post-transduction. Upper panels (HF): cells were transduced with the HF gp pseudotyped LVs. Lower panels (BRL): cells were transduced with the BRL gp pseudotyped LVs.

BRIEF DESCRIPTION OF THE SEQUENCES

| SEQ ID NO: | Description |
|---|---|
| 1 | 2A peptides consensus motif |
| 2 | F2A peptide |
| 3 | F2A peptide coding sequence |
| 4 | T2A peptide |
| 5 | T2A peptide coding sequence |
| 6 | P2A peptide |
| 7 | P2A peptide coding sequence |
| 8 | E2A peptide |
| 9 | E2A peptide coding sequence |
| 10 | codon optimized sequence encoding F2A peptide |
| 11 | codon optimized sequence encoding T2A peptide |
| 12 | codon optimized sequence encoding E2A peptide |
| 13 | furin cleavage site consensus sequence |
| 14 | furin cleavage site |
| 15 | sequence encoding a furin cleavage site |
| 16 | MH promoter |
| 17 | FEEK promoter |
| 18 | pAM signal |
| 19 | RRE |
| 20 | cPPT |
| 21 | WPRE |
| 22 | optimized WPRE |
| 23 | modified BaEV envelope glycoprotein |
| 24 | F2A/furin peptide sequence |
| 25 | F primer |
| 26 | R primer |
| 27 | Probe |
| 28 | actin F primer |
| 29 | actin R primer |
| 30 | Actin probe |
| 31 | Typical sequence of sequence B3 |
| 32 | Typical sequence of sequence B4 |

EXAMPLES

Example 1

The present example describes the design by the inventors of the multicistronic nucleic acid of the invention and its use to drive the expression of a membrane-anchored form and/or a secreted form of said antibody of interest depending on the maturation step of the B cell into which it was incorporated.
Material and Methods
Plasmid Constructions The light and heavy chain variable sequences of AR3A (Law et al. (2008) Nat. Med. 14:25-27) were amplified and inserted upstream of the human k chain constant and secretory IgG1 constant regions, respectively. Variable and constant domains were linked via the F2A/furin peptide of sequence 5'-cgggctaagaga gcaccggtgaaacagactttgaat-tttgaccttctcaagttggcgggagacgtggagtccaacccagggccc-3 (SEQ ID NO: 24) and subcloned downstream of the FEEK promoter of sequence SEQ ID NO: 17 into the FG12 vector described in Lois et al. (2002) Science 295/868-872 to create the FSS vector. The inventors removed the stop codon of the CH3 domain of the secretory version of human IgG1 and linked this domain to the transmembrane and cytoplasmic domains M1 and M2 of the human IgG1 BCR to create the FAM0 vector. Intronic sequences were inserted either between CH3 and M1 (FAM1 vector) or between CH3/M1 and M1/M2 (FAM2 vector). An unidirectional synthetic polyA sequence (SPA-TB1) of sequence SEQ ID NO: 18 was added after the stop codon. The lentiviral vectors carried the expression cassette in inverse orientation to preserve splicing sites during vector production. All vectors contain third generation self-inactivating lentiviral backbones. IgG1 heavy chains (HC) were optimized to limit inappropriate splicing due to cryptic splice donor and acceptor sites. Sequences were analyzed with an in silico splicing prediction algorithm and potential splicing site were mutated.
Lentiviral Vector Production and Titration The lentiviral vectors were generated by transient transfection of 293T cells. For pseudotyping with the BaeV glycoprotein described in Girard-Gagnepain et al. (2014) Blood 124:1221-1231, 7 µg of envelope plasmid was transfected together with a gagpol packaging plasmid (8.6 µg) and a plasmid encoding a LV-expressing AR3A (8.6 µg). For VSVg-pseudotyped LV, 2.3 µg of envelope plasmid was transfected. After 18 hours of transfection, the medium was replaced with Optimem supplemented with Hepes (Gibco, Invitrogen) for Baev-pseudotyped LV or DMEM complemented with 1% penicillin-streptomycin and 10% fetal calf serum (FCS) for VSVg-pseudotyped LV. Viral supernatants were harvested 48 hours after transfection and filtered. Low-speed concentration of the BaEV-vectors was performed by overnight centrifugation of the viral supernatants at 3,000 g at 4° C. VSVg-LV were concentrated by ultracentifugation with 20% sucrose at 25,000 g for 2 h at 4° C. Infectious titers (TU/ml) were detected by adding serial dilutions of the supernatants to 293T target cells as well as qPCR analysis of viral genome copy number at day 10 post-transduction.
Cell Lines and Transduction Protocols Namalwa (Burkitt lymphoma BL subtype PNT (ACC-69) IgM/λ purchased from DSMZ, Braunschweig, Germany) cells and U266 (plasmocytoma) cells were grown in RPMI medium (Gibco, Invitrogen, Aucklan, New Zealand) supplemented with 10% fetal calf serum and 50 µg/ml of penicillin/Streptomycin. 293T (human kidney epithelial cells) were grown in DMEM (Gibco, Invitrogen) medium supplemented in the same manner. For transduction, $3\times10^5$ cells were plated in 48 well plates and transduced with VSV-G-LV pseudotypes at an MOI of 10 to 20 to ensure similar transduction efficiency.
T and B Cell Isolation and Transduction Blood samples were obtained from healthy adult donors after informed consent in accordance with the Declaration of Helsinki and were collected in acid citrate dextrose. Peripheral blood mononuclear cells (PBMCs) were isolated on a Ficoll-gradient (Abcys Eurobio, France). CD19+ B cells and CD4+ T cells were isolated by negative magnetic selection using a B cell isolation kit and a CD4+ T cell isolation kit, respectively (Miltenyi Biotech, Paris, France). The purity of isolated B and T cells was assayed using anti-hCD19 and anti-hCD4 antibodies, respectively, and was analyzed by fluorescence-activated cell sorting (Cantoll; BD Biosciences, Le pont de Claix, France). Donors gave consent to use their blood specimen for research purposes, through deposit at the tumor bank of the Hospices Civils de Lyon, approved by French ethics law.

For in vitro transduction of primary B cells, cells were cultured in RPMI and prestimulated during 3-4 hours with 50 ng/mL IL2 (Miltenyi Biotech) and Pansorbin 200 ng/mL (Millipore calbiochem, Molsheim, France) followed by transduction at the indicated MOIs (10-20). Three days after transduction, the B cells were subcultured with MS5 feeder cells in the presence of IL2/IL15 (100 ng/ml) (Miltenyi Biotech).

For adoptive transfer experiments, B cells were immediately seeded for transduction in RPMI medium (Invitrogen) supplemented with 10% FCS in the presence of 50 ng/ml IL2 and 200 ng/ml of Pansorbin. Transductions were performed overnight with the BaEV-LVs at an MOI of 10. CD4$^+$ T cells were maintained on RPMI medium supplemented with 10% fetal calf serum (FCS) and 20 ng/mL of IL-7 overnight (Miltenyi Biotech).

ELISA

Supernatants from cultures of cell lines or mouse sera were analyzed using the human IgG ELISA Quantification set (Bethyl, Montgomery, USA), according to the manufacturer's instructions. The specific anti-E2 ELISA was described in Garrone et al. (2011) *Sci. Transl. Med.* 3:94ra71. Soluble HCV-E2 proteins were produced by transfection of phCMV plasmid encoding sequences of HCV-E2, fused at their C terminus to RGS-6×-histidine tag sequences. The threshold was about 7 ng/ml.

Neutralization Assays of HCVcc Viral Particles

Mouse sera were decomplemented during 1 h at 56° C. JC1 genotype HCVcc particles were incubated in different mouse sera (dilutions 1/20 and 1/40), before infection of Huh 7.5 cells. Antibody-mediated infection inhibition was determined for each sera by quantifying the foci forming-units per ml (FFU/ml) by immunohistochemistry, controlling for the known negative effect of murine serum on infection.

Reconstitution of Immunodeficient Mice

Immunodeficient mice NOD Scid$^{-/-}\gamma$c$^{-/-}$ (NSG) were housed in the PBES (Plateau de Biologie Expérimentale de la Souris), Lyon, France. Experiments were performed in accordance with the European Union guidelines following approval of the protocols by the local ethical committee (Authorization Agreement C2EA-15: Comité d'Evaluation Commun au Centre Léon Bérard, à l'Animalerie de transit de PENS, au PBES et au laboratoire P4, Lyon, France. Adult NSG (6-8 weeks old) were injected intra-peritoneally with $3\times10^6$ modified human primary B cells and $4\times10^6$ human primary CD4$^+$ T cells simultaneously. Blood samples were harvested weekly for FACS and ELISA analysis. Cell phenotyping in the spleen of these mice was performed after preparation of cellular suspension.

Flow Cytometry Analysis

For FACS analysis, monoclonal antibodies conjugated with either PE, APC, PeVio770, VioBlue, VioGreen, (VIT4)-APC coupled anti-human mAb targeting the following cell surface markers were used: IgM-APC (clone PJ2-22H3), IgG1-PE (clone IS11-12E4.23.20), Kappa-Vio770 (clone IS11-24D5), CD19-PEVIo770 (clone LT-19), CD45VioGreen (clone 5B1), from Myltenyi Biotech.

All washing and incubation steps were performed in PBS containing 2% FCS.

Flow cytometric analysis was performed using a FACScanto II and Diva software for acquisition (Becton Dickinson Immunocytometry Systems, Mountain View, Calif.) and FlowJo (Treestar, Ashland, Oreg.) software for analysis.

DNA Isolation and Copy Number Determination by qPCR/RT-PCR

Genomic DNA was extracted from the single cell suspension using the Nucleospin Blood kit (Macherey-Nagel, Düren, Germany) according to the manufacturer's instructions, and resuspended in 60 µl of the supplied elution buffer. Quantitative PCR (qPCR) was performed using the master mix applied (life technology) on a StepOnePlus system (Applied Biosystem, CA, USA). Specific primers for detection of integrated LV used: Primer F of sequence 5'-tgt gtg ccc gtc tgt tgt gt-3' (SEQ ID NO: 25), Primer R of sequence 5'-gag tcc tgc gtc gag aga gc-3' (SEQ ID NO: 26), Probe of sequence 5'-cag tgg cgc ccg aac agg ga-3' (SEQ ID NO: 27). Specific primer for human actin: Primer F of sequence 5'-tcc gtg tgg atc ggc ggc tcc a-3' (SEQ ID NO: 28), Primer R of sequence 5'-ctg ctt gct gat cca cat ctg-3' (SEQ ID NO: 29), Probe of sequence 5'-cct ggc ctc gct gtc cac ctt cca-3' (SEQ ID NO: 30).

Stimulation of BCR Signaling

At least 45 minutes before stimulation, $3\times10^5$ cells were aliquoted in 100 µL of PBS-BSA 0.5% in flow cytometry tubes and equilibrated at 37° C. in a waterbath. After equilibration, the cells were stimulated with a final concentration of 30 µg/ml of each of the F(ab')$_2$ immunoglobulins. Cross-linking of B cell receptors was performed using goat polyclonal anti-IgM and anti-IgG F(ab')$_2$ (Southern Biotech, Alabama, USA).

During signaling, cells were incubated 10 min at 37° C. to allow signal transduction and phosphorylation to occur. To determine the basal levels of phosphorylation, unstimulated cells were maintained in parallel with stimulated cells. Fixation and intracellular phospho-specific flow cytometry was performed using the perfix expose kit (Beckman coulter, California, USA) according to manufacturer instructions. For detection, anti BLNK-pY84 (AlexaFluor647, BD, clone J117-1278) was used. Samples were stored at 4° C. until staining for flow cytometry.

Western Blot

Protein extraction was performed with Ripah buffer and equal quantities of protein were electrophoresed in 8% SDS-PAGE gels under nonreducing conditions. Western blot analysis was performed with an anti-calnexin antibody (SPA-860, Stressgen Biotechnologies Corp, Canada) and anti-IgG heavy chain (LsBio60606, Cliniscience, France).

Statistical Analysis

Statisical analysis was performed using a paired Student t test. For the HCVcc neutralization assay with mouse sera, Statisical analysis was performed using a Mann Whitney test.

Results

Figure 1:
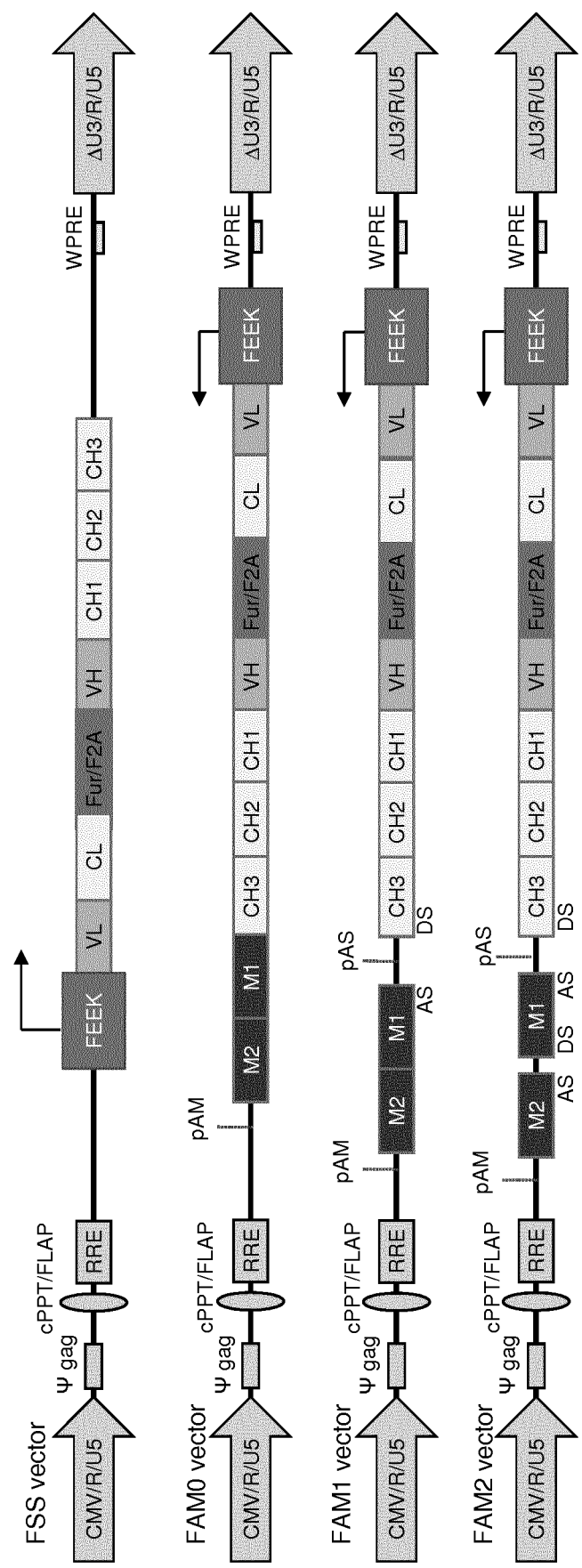
FIG. 1: Four lentiviral vector constructs encoding the membrane-anchored or secretory form of AR3A-IgG1 (directed against E2 HCV) driven by Ig light chain promoter (FEEK) were generated. The constant IgG1 heavy chain (CH) and kappa light chain (CL) genes were fused with the AR3A variable regions (VL and VH). Co-expression of CHs and VHs were obtained by introduction of the F2A peptide sequences. The FSS vector allows exclusively expression of the secreted form of AR3A. The FAM0 vector drives the expression of the membrane-bound form of AR3A. The FAM1 and FAM2 vectors were designed for the expression of both the secreted and membrane-anchored forms of AR3A. For the FAM1-LV, a short intronic sequence was introduced between the CH3 and M1 exons and for the FAM2-LV two short intronic sequences were included between the CH3 and M1 exons and between the M1 and M2 exons, respectively.

Design of Lentiviral Vectors for Conditional Expression of Both Secreted and Membrane-Anchored Forms of the AR3A Antibody The aim of the inventors was to produce a lentiviral vector (LV) conditionally expressing both the secreted and the membrane-anchored form of a transgenic immunoglobulin (Tg-Ig), in a manner regulated by the maturational state of transduced B cells. To this end, they constructed several LV variants incorporating alternative splicing and polyadenylation mechanisms regulated by the cellular machinery. These variants are depicted on FIG. 1. They linked the variable and constant regions from the λ1 heavy chain (HC) and κ light chain (LC) of the AR3A antibody via a furin/F2A "ribosome-skipping" peptide to allow coexpression of both subunits. The FEEK B cell-specific promoter was introduced into the LVs to allow native regulation of gene expression in target B cells. As natural intronic sequences represented more than 1 kb of the Ig sequence, the inventors trimmed them to prevent diminution of viral titers thereby avoiding loss of intron recognition.

To mimic the natural expression of secreted and surface-displayed Igs, the inventors designed two conditionally-expressing vectors, FAM1 and FAM2. The plasmid cards of these vectors are respectively represented on FIGS. 2 and 3. In these LVs, the minimal intronic sequences of γ1 HC gene containing both the splicing and polyadenylation signals of its 3' terminal exon as well as the transmembrane coding regions M1 and M2 of sequence were inserted. In the FAM1 LV, the intron was introduced between the M1M2 fused exons, which encode for the Ig transmembrane domain, and the CH3 exon, whereas in the FAM2 LV, an additional intronic sequence was introduced between the M1 and M2 exons. Importantly, both expression cassettes were cloned in reverse orientation in the vector in order to avoid intron excision during LV production. The inventors also designed two additional LVs: the FSS vector, which expresses only the secreted form of AR3A, and the FAM0 vector, which exclusively encodes the membrane-anchored form of the same AR3A antibody (Ab). In this latter vector, the coding regions of the M1 and M2 transmembrane domains of the IgG1 heavy chain were directly fused to the CH3 domain. The plasmid cards of these vectors are respectively represented on FIGS. 4 and 5.

In transduced cells, the inventors expected that the membrane-anchored form of the AR3A ab would be expressed by FAM0-transduced cells whereas the secreted form by FSS-transduced cells. Moreover, as Burkitt lymphoma (BL) cells have a mature B cell phenotype, the conditional FAM1 or FAM2-transduced BL cells should express the membrane-anchored form whereas in plasma cells, the opposite is expected, i.e., the FAM1 and FAM2 LVs should mediate predominant expression of the secreted form. The conditional expression of either membrane-anchored form (in mature B cells) vs secreted form (in plasma cells) from the host cell DNA-integrated lentiviral vector is schematized on FIG. 6.

LVs Mediate Conditional Expression of Secreted and Membrane-Anchored Antibody Forms To investigate whether these physiologically regulated vectors mediated expression of both the secreted and membrane-anchored forms of the AR3A ab, the inventors first transduced the Burkitt's lymphoma (BL) cell line with the different LV constructs. These cells are arrested at a mature B-cell differentiation stage and express endogenous membrane-bound Igs constituted of the association of the μ heavy chain with λ light chains forming a complete IgM molecule. It was shown that the PNT subtype of the Namalwa BL cells is also able to secrete some IgM in addition to the predominant membrane-anchored form. This indicates that such BL cells should be operational to process the constructs for selective expression of the membrane-anchored form of the transgenic Ig. Moreover, the endogenous BCR of this cell line belonging to the IgM isotype, it should not interfere with the detection of the transgenic IgG1/κ Ig.

AR3A Ig expression and secretion were assessed in supernatants and cells by Western blot and Elisa, five days post-transduction (FIGS. 7, 8 and 9). Flow cytometry was used to monitor the membrane expression of the transgene using anti-IgG1 Abs (FIG. 10).

To first characterize expression of the transgenic IgG γ1 heavy chain driven by each construct, the proteins of whole cell lysates of transduced cells were separated on SDS-PAGE gels under reducing conditions and subjected to western blot analysis for human γ HC. The addition of the M1 and M2 domains to the HC protein results in HCm (i.e., the membrane-anchored form of Ig heavy chain) being larger than HCs (i.e., the secreted form of Ig heavy chain) for all Ig isotypes. As expected, only HCs was readily detected in the FSS-transduced cell lysates while HCm was the only form detectable in FAM0-transduced cells lysates (FIG. 7). Transduction of Namalwa BL cells with the FAM1 vector did not drive the expression of HCm but only of HCs, suggesting that some polyadenylation and splicing signals are missing or not functional in this construct, hence preventing maturation to the HCm form. Interestingly, both HCm and HCs isovariants were detected when cells were modified with the conditional vector FAM2 (FIG. 7). Of note, HCs isoforms were also detected in mature B cell lines, as described by Price et al. (2009) *J. Immunol. Methods* 343:28-41.

Therefore, both membrane and secreted Ig expressions were detected in FAM2-transduced BL cells. Despite the fact that the production of the longer HCm form is more difficult to obtain than the short form HCs due to the presence of the intronic sequence and splicing events and considering that BL cells need to process their proper endogenous IgM Ig, the ratio HCm/HCs obtained with the FAM2 LV appeared to be good.

High transduction efficiencies (>97%) were obtained for each vector, as assessed by intracellular staining for the transgenic κ light chain, though the expression level (MFI) of the κ light chain was lower in the FAM2- and FAM0-transduced cells than in FSS-modified cells (FIG. 10). This might be explained by a difference in the LV RNA stability due to the presence of the RNA stabilizing WPRE sequence, which is only present in the FSS viral RNA.

Interestingly, the inventors detected the γ1 HC surface expression (surface IgG1) on the transduced cells with different intensities, depending on the vector design (FIGS. 10 and 8). Yet, although this vector expresses only the secreted form of the antibody, some level of surface γ1 HC was detected in BL cells transduced with the FSS LV. The fact that FSS-transduced cells do not express the membrane-anchored Ig form (FIG. 7) indicated that the global shift in surface γ1 HC expression levels in the entire population of transduced cells was not due to expression of a proper BCR form, in contrast to cells transduced with the FAM0 vector. Indeed, Namalwa BL cells express the Fc receptor (FcR) CD32, which has a high affinity for IgG1 subtype. Therefore, the inventors considered that the γ1 detection at the surface of transduced cells is likely due to the binding of the secreted AR3A Ab to CD32. Compared to the FSS LV, the FAM1 LV-transduced BL cells did not detectably express surface IgG1 (FIG. 10), in agreement with results of FIG. 7. Importantly, the FAM2 LV induced expression of transgenic IgG1 at the cell surface in a manner equivalent to that obtained with the FAM0 control vector, which encodes exclusively a membrane-anchored IgG1 form.

The inventors found that the levels of cell membrane-anchored AR3A Ab detected from the different LV constructs were inversely correlated to the secretion of the antibody in the supernatant, as determined with a specific anti-E2 ELISA (FIG. 9). No AR3A Ab was detected in the supernatant of cells transduced with the FAM0 LV expressing the BCR form, whereas cells transduced with the FSS vector expressed the highest levels of secreted AR3A (125±65 ng/ml). Interestingly, flow cytometry and ELISA analysis demonstrated that the FAM2 LV preferentially expressed the membrane-anchored form of AR3A (23±7%, FIG. 8) similar to the FAM0 control LV (27±9%, FIG. 8), but produced less of the soluble form (8.1±2.8 ng/ml, as compared to 132±80 ng/ml obtained with the FSS control LV, FIG. 9). This was expected, since Namalwa BL have a mature B cell phenotype and do not display the developed secretory apparatus of PCs.

Next, the inventors transduced the U266 plasmocytoma cells that represent a late stage of B cell maturation and that have an IgE/λ phenotype. In contrast to BL cells, U266 cells preferentially modify Ig mRNA to express secreted forms of Ig and do not process membrane-anchored Ig forms.

Importantly, U266 cells transduced with all LVs expressed low level of AR3A IgG1 at the cell surface (i.e., less than 4%, FIGS. 11 and 12), as expected for plasmocytoma cells because of the absence of Igα and Igβ BCR co-receptor required for the export at the cell surface. Furthermore, owing to the fact that these U266 cells do not express CD32 Fc receptor, no cell surface binding of the secreted form of AR3A Ab induced by the FSS and FAM1 LVs was observed, in contrast to BL cells. Consistently, in contrast to BL cells, the inventors readily detected the anti-E2 IgG1 antibody in the supernatant of U266 cells transduced FAM2 LV (125±65 ng/ml) conditional vectors (FIG. 13). Particularly, consistent with the plasma cell phenotype of U266 cells, FAM2 LV transduction of the U266 cells resulted in preferential expression of the secreted form compared to the surface BCR form (23.6±7.5% vs 3.6±1.8%, FIG. 12) and 16-fold more secreted AR3A Ab was detected in FAM2-transduced U266 cells compared to BL cells (125±65 vs 8.1±2.8, FIG. 13).

Altogether, these results indicated that the splicing and polyadenylation regulatory sequences in the FAM2 LV (between CH3 and the M1 domain and between the M1 and M2 domains), in association with the cellular machinery involved in the secretion or export of the BCR at the cell surface, allow the production of both membrane-anchored and secreted forms of AR3A Ig depending on the B cell maturation status.

Transgenic AR3A-BCR Expression Only Weakly Impacts Expression of Endogenous Ig

A concern related to ectopic expression of Abs is the potential change in the regulation or expression of endogenous antibodies, which may change the maturation state of the cells or may lead to autoimmune disorders or loss of immune reactivity. Therefore, the inventors evaluated the consequences of the ectopic expression of the AR3A Ab on the endogenous expression of Ig in LV-transduced Namalwa BL cells.

Interestingly, the intracellular level of the endogenous HCm was not affected, considering both the percentage of intracellular IgM+ (cyIgM) cells (FIGS. 14 and 15, black bars) as well as the IgM expression intensity (FIG. 16, black bars). The analysis of the endogenous surface IgM HC (sIgM) expression in transduced BL cells revealed a weak modification of the expression of the endogenous IgM HC. Indeed, both the percentage of surface IgM-positive cells (FIGS. 17 and 15, grey bars) and the surface IgM expression levels (FIGS. 17 and 16, grey bars) detected upon transduction with either FAM2 or FAM0 vectors was by ca. 20% reduced as compared to those obtained with FSS or FAM1 LVs.

Altogether, these results suggested that the intracellular trafficking and expression levels of the endogenous BCR were only weakly affected by ectopic expression of a transgenic BCR.

Stimulation of Ectopic BCR Expressed by FAM2 LV-Transduced Cells Triggers BCR Signaling Because one goal of the inventors was to generate Ig transgene-expressing B cells that could drive B cell maturation into Ab-secreting cells, they tested the functionality of the membrane-anchored form of the Ig constructs. They chose to monitor phosphorylation of the tyrosine Y84 of the proximal BCR BLNK adaptor, one of the most receptor proximal elements of the BCR signaling pathway. To amplify this signal, they sought to engage the BCR in primary B cells with the F(ab')$_2$ fragments of polyclonal anti-IgM vs. anti-IgG Abs. Such surrogate Ag allowed for a high degree of cross-linking of the transgenic BCR, as compared to that induced by E2 Ag, and the comparison of the signaling outcome of engagement of the transgenic or endogenous BCR. Phosphorylation of BLNK was detected in cells transduced with the Ig-expressing LVs as well as in non-transduced cells after stimulation of the IgM endogenous BCR (FIG. 18). This indicated that the endogenous BCR remained functional, in agreement with its only weak cell surface down-regulation upon LV transduction.

Importantly, signaling through the ectopically expressed BCR occurred only in the FAM2- and FAM0-transduced cells following stimulation by an anti-IgG F(ab')$_2$ (FIG. 19). The ratio between BLNK-Y84 phosphorylation under anti-IgG stimulation compared to anti-IgM stimulation was significantly higher with the FAM2- and FAM0-transduced cells, i.e., 38% and 47%, respectively, compared to non-transduced cells (FIG. 20).

Altogether, these results demonstrated that the FAM2 LV allows the expression of a functional BCR form of the transgenic IgG1.

The FAM2 Vector Allows the Expression of a Membrane-Anchored Form of the Transgenic IgG1 in Primary Human B Cells The inventors then evaluated IgG expression in primary human B cells. Hence, they used BaEV envelope-pseudotyped LVs, which can readily transduce both quiescent and BCR-stimulated human B cells. They transduced purified human primary CD19$^+$ B cells with the FSS, FAM0, FAM1 and FAM2 LVs to investigate the production of the two active forms of the AR3A Ab ex vivo. Primary B cells were transduced at an MOI of 10 with each vector and were further cultured for 7 days on MS5 stroma cells. During culture, the cells retained a CD19$^+$ CD20$^+$ mature B cell phenotype without differentiation into PCs.

The transduction efficiency of these cells ranged from 30 to 52% using a control GFP-expressing LV. The inventors found a significant and reproducible increase in the percentage of cells expressing surface IgG1/κ following transduction by the FAM2 (5.75%) and FAM0 LVs (5.12%), as compared to the non-transduced cells (2.37%) or to cells transduced with the FSS (2.63%) or FAM1 (2.43%) LVs (FIGS. 21 and 22). In addition, the MFI of γ1 HC at the cell surface was significantly increased with the FAM0 and FAM2 LVs (FIG. 23) compared to non-transduced cells or to FSS LV- and FAM1 LV-transduced cells. These results indicated that the FAM2 conditional vector allows the expression of the BCR form of the transgenic IgG AR3A in a fraction of primary human B cells. Soluble AR3A was quantified at 10.45 ng/ml (mean±0.65) in the supernatant of FSS LV-transduced cells but was below the detection limit for cells transduced with the FAM0 LV or the FAM1 or FAM2 conditional LVs. This was expected since the mature B cell phenotype of these cells correlates with the preferential production of surface Ig.

Adoptive Transfer of FAM2 LV-Transduced B Cells Induce Neutralizing Antibody In Vivo.

To further demonstrate the ability of the FAM2 construct to drive expression of both the membrane and secreted forms of the Ig transgene, the inventors analyzed the secretion of the AR3A Ab by the plasma cell progeny of human B cells transduced with the different constructs.

Human B cells can be differentiated into plasma cells (PCs) by adoptive transfer of CD19$^+$ B cells and autologous CD4$^+$ T cells into the immunodeficient mice. The inventors used the NOD/SCIDγ$_c$$^{-/-}$ (NSG) mouse model, which has been shown to be suitable for the study of the production of human Ig (Hasui et al. (1994) *Clin. Exp. Immunol.* 95:357-361; Martensson et al. (1995) *Immunology* 86:224-230). The inventors transduced purified human B cells with the FSS, FAM0, and FAM2 LVs and induced their differentiation by adoptive transfer into NSG mice. In this context, B cells are activated and differentiated into PC under the polyclonal activation signal triggered by the xenograft, possibly consecutive to massive activation of human CD4+ T cells by the mouse xenoantigens. This allowed the inventors to induce the expression of the AR3A Ab upon in vivo maturation of LV-transduced B cells into plasmocytes, induced by this xenogeneic reaction.

Human CD19+ B cells constituted 20-30% of cells in mouse spleens, independent of the LV used to transduce these cells. Importantly, the inventors observed significant increase in the CD19+ IgG1+ B cell subpopulation in mice engrafted with FAM2 and FAM0 LV-transduced B cells compared to mice engrafted with non-transduced or FSS modified cells (FIG. 24, donor B). These results confirmed the in vitro data obtained with primary B cells and demonstrated that the FAM2 conditional vector allows the expression of BCR form of the transgenic IgG AR3A in human B cells in vivo.

The blood plasma of the engrafted mice was harvested weekly and assessed by ELISA for the presence of total human IgG and of HCV E2-specific antibodies (i.e., AR3A Ab). As expected, no secreted AR3A Ab was detected in the plasma from mice engrafted with non-transduced cells or with cells transduced by the FAM0 LV (FIG. 25). Importantly, the AR3A Ab was readily detected in plasma of mice engrafted with FSS and FAM2 LV-transduced human B cells (2.45±1.18 µg/ml and 0.81±0.85 µg/ml, respectively). As expected, mice engrafted with human B cells transduced with the FSS LV produced the highest quantities of AR3A antibody. AR3A antibodies comprised a low percentage of total huIgG (0.02%) in mouse sera at day 21 post-transfer with FAM2 LV-transduced cells (FIG. 26), representing the basal expression of transgenic IgG1 without specific activation of modified B cells. This basal level of transgenic IgG secretion was expected in the absence of an antigen-specific amplification of the pool of modified B cells expressing the membrane-anchored form.

Finally, to ensure that the secreted AR3A Ab present in the mouse sera was functional, the inventors performed an in vitro neutralization assay using HCVcc particles. They found that HCVcc infection of Huh-7.5 hepatoma cells was significantly neutralized by mouse sera containing secreted AR3A antibody (range final concentration of AR3A in mouse sera: 0.06-1 µg/ml) compared to a low non-specific HCVcc inhibition by AR3A-negative serum (FIG. 27), likely due to the presence of serum-derived inhibitors.

Altogether these data demonstrate that FAM-2-modified B cells can express the membrane-bound form and secrete the soluble active form of the ARA3 neutralizing Ab in vivo.

DISCUSSION

This example describes the first lentiviral vector allowing the expression of physiologically active form of a human monoclonal Ab by employing the natural mechanism of Ig maturation during B cell development. These data provide attractive tools for active immunotherapy against infectious disease and tumoral antigens.

Previous studies have used a variety of approaches to express both the membrane-anchored and/or secreted form of the same human Ab in B or non B cell. However, in these studies, the relative levels of either form remained constant and could not switch according to B cell maturation. In the present example, the approach used involves the modification of human B cells by LV that induce Ig expression in a physiologically adaptable manner.

Reproducing the physiological regulation of Ig expression and mRNA processing in the context of a lentiviral vector is challenging. Previous attempts to produce anti-HIV antibodies were only partially successful in achieving this goal. Hence, the ability to use the natural regulation of Ig pre-mRNA processing is a major step forward in the field of immunotherapy. In particular, in the context of lentiviral vectors, the use of splicing and poly-adenylation mechanisms to obtain physiological expression of both membane-anchored and secreted forms of human Igs has been unsuccessful so far (Yu et al. (2012) PLoS One 7:e50438). Alternatively, this study used mutated self-cleaving F2A peptides to modulate the ratio between secreted and membrane-bound Ig, which remains, however, independent of the B-cell maturation status.

Here, the inventors provided evidence that B cells can be successfully modified to express both transgenic Ig forms depending on the B cell maturation status by using minimal required alternative splicing and polyadenylation signals. Overall, the inventors demonstrated that Ig expression from a FAM2 lentiviral responded well to the specific secretory and export machinery of these cells.

Achieving long-term gene transfer into primary human B cells has been notoriously difficult because the classical VSV-G envelope glycoprotein used to produce pseudo-typed-LVs is not efficient. Therefore, LVs pseudotyped with an envelope glycoprotein derived from the Baboon endogenous virus (BaEV) were developed, which permits efficient transduction of resting and BCR-stimulated human B cells. The combination of this specific envelope pseudotype together with the FAM2 LV described herein enabled the inventors to express membrane and secreted AR3A Ab in proportions that were modulated by the B cell differentiation state in cell lines and primary human cells. Indeed, using B cell lines that are biased toward either secretory (PC-like) or non-secretory (mature B cell-like) phenotypes, the inventors highlighted the production of both membrane-anchored IgG1 BCR and secreted antibody in vitro using the FAM2 vector. Expression of Ig membrane-anchored form was inversely correlated with their secretion in supernatants.

FAM1 and FAM2 vectors were designed to determine whether the intronic sequence between M1 and M2 was essential for correct Ig mRNA splicing. The inventors found that the FAM1 LV-modified B cells behaved with an intermediate profile between FSS and FAM2 and FAM0-transduced cells, since they permitted predominantly the expression of the secreted Ab form, but not membrane-bound form. Therefore, the inventors demonstrated that, in the context of a LV, the short intronic sequence separating the M1 and M2 exons as in the FAM2 LV is crucial for appropriate splicing of the Ig mRNA.

Previous studies aiming at determining the Ig forms produced during B cell maturation used in vivo differentiation assays of B cells to PCs in mice co-injected with T cells enhanced Ig production. The inventors therefore co-injected human CD4+ helper T cells and B cells into immunodeficient mice and found that transduced B cells were able to differentiate into PCs after adoptive transfer into NSG mice. Importantly, they detected a high level of Ig secretion after in vivo B cell maturation with significant production of secreted AR3A in sera of mice engrafted with FAM2 LV-transduced B cells, which demonstrated that B cell modification by the conditional FAM2 LV did not interfere with B cell maturation. AR3A represented approximately 0.02% of total IgG Ab in mouse sera. By comparison, anti-tetanus toxin IgG1 antibody represents approximately 0.08% of total IgG in vaccinated adults.

HCV Ag-specific presentation to modified B cells should permit the amplification of BCR-expressing B cells and concomitant maturation into AR3A-secreting PC. An important objective of the present conditional Ig expression strategy was to maintain a basal level of AR3A secretion along, in the absence of stimulation, with membrane anchored BCR form to avoid continuous high and potentially deleterious production of Ab. Considering that the expression of the transgenic Ab from the FAM2 vector is more complex than expression of a secreted form lacking intronic sequences (such as e.g., from the FSS LV), the inventors demonstrated effective production of the soluble Ab form in in vivo-differentiated human PC. Indeed, AR3A concentration in mouse sera following adoptive transfer of stimulated B cells was sufficient to neutralize HCVcc infection in vitro. In parallel, the secreted transgenic IgG1 represented about 0.02% of the total huIgG in the mouse sera, in the absence of specific activation by HCV antigens. The goal of this vector is to maintain basal level of the transgenic IgG1 without immunogenic activation. After specific HCV-E2 antigenic stimulation, amplification and differentiation of the transgenic mature B cell expressing the BCR form should provide a pool of secreting cells able to produce AR3A Ab.

Vectored immunoprophylaxis (VIP) is an attractive alternative to passive immunotherapy, as this requires a single in vivo inoculation of viral vectors to produce continuous and sustained expression of specific antibodies. AAV-based vectors are the most commonly vectors used for such a strategy in cancerology or infectious diseases. However, in vivo administration of AAV-based vectors may have low efficiency due to the high prevalence of pre-existing anti-AAV antibodies in most human populations. Most importantly, continuous high-level Ab production would be expected to be deleterious to patients. Thus, the conditional LV of the invention provides an attractive alternative strategy by mimicking the natural regulation of Ab production after ex vivo modification of targeted cells, namely B cells or hematopoietic stem cells.

Example 2

This example confirms that the results described in Example 1 using lentiviral vectors pseudotyped with BaEV glycoprotein can also be obtained with lentiviral vectors pseudotyped with other glycoproteins specifically targeting B cells or $CD34^+$ hematopoietic stem cells.

Material and Methods

Plasmid Constructions

The plasmid constructions FSS, FAM0 and FAM2 were obtained as described in Example 1.

Lentiviral Production and Titration

The lentiviral vectors were obtained as described in Example 1, except that, in the case of the lentiviral vectors pseudotyped with the measles virus glycoprotein, the envelope plasmid encoded the modified measles virus HΔ24 and FΔ30 glycoproteins described in Frecha et al. (2008) Blood 112:4843-4852.

B Cell Isolation and Transduction

B cells were isolated and transduction as described in Example 1.

Flow Cytometry Analysis

Flow cytometry analysis was carried out as described in Example 1.

Results

The inventors evaluated IgG expression in primary B human B cells. They used both BaEV envelope-pseudotyped LVs and measles virus HF envelope-pseudotyped LVs. They transduced purified human primary $CD19^+$ B cells with the FSS, FAM0 and FAM2 LVs to investigate the production of the two active forms of the AR3A Ab ex vivo. Primary B cells were transduced at an MOI of 10-15 with each vector for vectors pseudotyped with BaEV envelope and at an MOI of 1-10 with each vector for vectors pseudotyped with measles virus HF envelope, and were further cultured for 7 days on MS5 stroma cells.

The inventors found a significant increase in the percentage of cells expressing surface IgG1/κ following transduction by the FAM2 and FAM0 HF-pseudotyped LVs (respectively 12.8 and 25.6 fold increase) as compared to cells transduced with the FSS LVs (FIGS. 28 to 30).

The results observed with HF-pseudotyped LVs as thus similar to those observed with BaEV-pseudotyped LVs.

The invention claimed is:

1. A multicistronic nucleic acid allowing physiologically-regulated expression of a membrane-anchored and/or secreted antibody by B cells comprising:
   A) a sequence comprising successively:
      A1) a sequence encoding a light chain variable domain of an antibody of interest, fused in the frame with
      A2) a sequence encoding a constant region of the light chain of an immunoglobulin Ig; and
   B) a sequence comprising successively:
      B1) a sequence encoding a heavy chain variable domain of said antibody of interest, fused in the frame with
      B2) a sequence encoding constant regions of the heavy chain of an immunoglobulin Ig' in secretory form;
      B3) an intronic sequence of a gene of the heavy chain of said immunoglobulin Ig', said intronic sequence consisting of between 350 and 380 nucleotides and comprising an internal 5' splice site enabling the splicing of said intronic sequence B3) and a secretory-specific poly(A) (pAS) signal from the 3' terminal exon of said gene of the heavy chain;
      B4) a sequence, in frame with sequence B1), encoding transmembrane and cytoplasmic domains M1 and M2 of an immunoglobulin Ig' BCR, wherein said sequence B4) comprises, between the coding sequences of the M1 and M2 domains, an intronic sequence containing a splice site enabling the splicing of said intronic sequence between the M1 and M2 domains coding sequences, wherein said intronic sequence consists of between 200 and 250 nucleotides; and
      B5) a membrane-anchored specific poly(A) signal (pAM), after the stop codon of the M2 domain,
   wherein the multicistronic nucleic acid enables the co-expression of the sequences A and B into separate proteins and wherein said sequences A and B are linked by a linking sequence enabling the co-expression of the sequences A and B in a single mRNA.

2. The multicistronic nucleic acid according to claim 1 comprising before said sequence A a B-cell specific promoter operably linked to said sequence A.

3. The multicistronic nucleic acid according to claim 1, wherein the sequences B3), B4) and/or B5) are codon-optimized to limit inappropriate splicing due to the possible presence of cryptic splice donor and acceptor sites.

4. A method for inducing the physiologically-regulated expression of a membrane-anchored and/or secreted antibody of interest by a B cell ex vivo, comprising by exposing the B cell to a plasmid comprising the multicistronic nucleic acid according to claim 1.

5. A multicistronic nucleic acid encoding an antigen-binding domain/effector protein chimera allowing physiologically-regulated expression of a membrane-anchored and/or secreted antigen-binding domain/effector protein chimera by B cells, the antigen-binding domain and/or the effector protein being respectively formed by two subunits, said nucleic acid comprising:
   A) a sequence comprising successively:
      A1) a sequence encoding a first subunit AbD1 of an antigen-binding domain AbD, fused in the frame with
      A2) a first subunit EfP1 of an effector protein EfP, or optionally a sequence encoding an effector protein EfP; and
   B) a sequence comprising successively:
      B1) a sequence encoding a second subunit AbD2 of the antigen-binding domain AbD, AbD2 forming in combination with AbD1 an antigen-binding domain specifically interacting with an antigen of interest, said sequence B1 being fused in the frame with
      B2) a sequence encoding a second subunit EfP2 of the effector protein EfP or a sequence encoding the effector protein EfP;
      B3) an intronic sequence of a gene of a heavy chain of an immunoglobulin Ig', said intronic sequence consisting of between 350 and 380 nucleotides and comprising an internal 5' splice site enabling the splicing of said intronic sequence B3) and a secretory-specific poly(A) (pAS) signal from the 3' terminal exon of said gene of the heavy chain;
      B4) a sequence, in frame with sequence B1), encoding transmembrane and cytoplasmic domains M1 and M2 of an immunoglobulin Ig' BCR, wherein said sequence B4) comprises, between the coding sequences of the M1 and M2 domains, an intronic sequence containing a splice site enabling the splicing of said intronic sequence between the M1 and M2 coding sequences, wherein said intronic sequence consists of between 200 and 250 nucleotides; and
      B5) a membrane-anchored specific poly(A) signal (pAM), after the stop codon of the M2 domain,
   wherein the multicistronic nucleic acid enables the co-expression of the sequences A and B into separate proteins and wherein said sequences A and B are linked by a linking sequence enabling the co-expression of the sequences A and B in a single mRNA.

6. A nucleic acid encoding an antigen-binding domain/effector protein chimera allowing physiologically-regulated expression of a membrane-anchored and/or secreted antigen-binding domain/effector protein chimera by B cells, said nucleic acid comprising:

A) a sequence encoding an antigen-binding domain AbD specifically interacting with an antigen of interest; and
B) a sequence comprising successively:
   B2) a sequence encoding an effector protein EfP;
   B3) an intronic sequence of a gene of a heavy chain of an immunoglobulin Ig', said intronic sequence consisting of between 350 and 380 nucleotides and comprising an internal 5' splice site enabling the splicing of said intronic sequence B3) and a secretory-specific poly(A) (pAS) signal from the 3' terminal exon of said gene of the heavy chain;
   B4) a sequence, in frame with sequence B2), encoding transmembrane and cytoplasmic domains M1 and M2 of an immunoglobulin Ig' BCR, wherein said sequence B4) comprises, between the coding sequences of the M1 and M2 domains, an intronic sequence containing a splice site enabling the splicing of said intronic sequence between the M1 and M2 coding sequences, wherein said intronic sequence consists of between 200 and 250 nucleotides; and
   B5) a membrane-anchored specific poly(A) signal (pAM), after the stop codon of the M2 domain,
wherein the nucleic acid enables the expression of the sequences A and B into a single protein.

7. A transfer retroviral vector allowing physiologically-regulated expression of a membrane-anchored and/or secreted antibody or antigen-binding domain/effector protein chimera by B cells comprising:
   (i) a transfer retroviral backbone, and
   (ii) a multicistronic nucleic acid comprising:
   A) a sequence comprising successively:
      A1) a sequence encoding a light chain variable domain of an antibody of interest, fused in the frame with
      A2) a sequence encoding a constant region of the light chain of an immunoglobulin Ig; and
   B) a sequence comprising successively:
      B1) a sequence encoding a heavy chain variable domain of said antibody of interest, fused in the frame with
      B2) a sequence encoding constant regions of the heavy chain of an immunoglobulin Ig' in secretory form;
      B3) an intronic sequence of a gene of the heavy chain of said immunoglobulin Ig', said intronic sequence consisting of between 350 and 380 nucleotides and comprising an internal 5' splice site enabling the splicing of said intronic sequence B3) and a secretory-specific poly(A) (pAS) signal from the 3' terminal exon of said gene of the heavy chain;
      B4) a sequence, in frame with sequence B1), encoding transmembrane and cytoplasmic domains M1 and M2 of an immunoglobulin Ig' BCR, wherein said sequence B4) comprises, between the coding sequences of the M1 and M2 domains, an intronic sequence containing a splice site enabling the splicing of said intronic sequence between the M1 and M2 domains coding sequences, wherein said intronic sequence consists of between 200 and 250 nucleotides; and
      B5) a membrane-anchored specific poly(A) signal (pAM), after the stop codon of the M2 domain,
   wherein the multicistronic nucleic acid enables the co-expression of the sequences A and B into separate proteins and wherein said sequences A and B are linked by a linking sequence enabling the co-expression of the sequences A and B in a single m RNA; or
a multicistronic nucleic acid encoding an antigen-binding domain/effector protein chimera, the antigen-binding domain and/or the effector protein being respectively formed by two subunits, said nucleic acid comprising:
   A) a sequence comprising successively:
      A1) a sequence encoding a first subunit AbD1 of an antigen-binding domain AbD, fused in the frame with
      A2) a first subunit EfP1 of an effector protein EfP, or optionally a sequence encoding an effector protein EfP; and
   B) a sequence comprising successively:
      B1) a sequence encoding a second subunit AbD2 of the antigen-binding domain AbD, AbD2 forming in combination with AbD1 an antigen-binding domain specifically interacting with an antigen of interest, said sequence B1 being fused in the frame with B2) a sequence encoding a second subunit EfP2 of the effector protein EfP or a sequence encoding the effector protein EfP;
      B3) an intronic sequence of a gene of a heavy chain of an immunoglobulin Ig', said intronic sequence consisting of between 350 and 380 nucleotides and comprising an internal 5' splice site enabling the splicing of said intronic sequence B3) and a secretory-specific poly(A) (pAS) signal from the 3' terminal exon of said gene of the heavy chain;
      B4) a sequence, in frame with sequence B1), encoding transmembrane and cytoplasmic domains M1 and M2 of an immunoglobulin Ig' BCR, wherein said sequence B4) comprises, between the coding sequences of the M1 and M2 domains, an intronic sequence containing a splice site enabling the splicing of said intronic sequence between the M1 and M2 coding sequences, wherein said intronic sequence consists of between 200 and 250 nucleotides; and
      B5) a membrane-anchored specific poly(A) signal (pAM), after the stop codon of the M2 domain,
   wherein the multicistronic nucleic acid enables the co-expression of the sequences A and B into separate proteins and wherein said sequences A and B are linked by a linking sequence enabling the co-expression of the sequences A and B in a single mRNA; or
a nucleic acid encoding an antigen-binding domain/effector protein chimera, said nucleic acid comprising:
   A) a sequence encoding an antigen-binding domain AbD specifically interacting with an antigen of interest; and
   B) a sequence comprising successively:
      B2) a sequence encoding an effector protein EfP;
      B3) an intronic sequence of a gene of a heavy chain of an immunoglobulin Ig', said intronic sequence consisting of between 350 and 450 nucleotides and comprising an internal 5' splice site enabling the splicing of said intronic sequence B3) and a secretory-specific poly(A) (pAS) signal from the 3' terminal exon of said gene of the heavy chain;
      B4) a sequence, in frame with sequence B2), encoding transmembrane and cytoplasmic domains M1 and M2 of an immunoglobulin Ig' BCR, wherein said sequence B4) comprises, between the coding sequences of the M1 and M2 domains, an intronic sequence containing a splice site enabling the splicing of said intronic sequence between the M1 and M2 coding sequences, wherein said intronic sequence consists of between 200 and 250 nucleotides; and B5) a membrane-anchored specific poly(A) signal (pAM), after the stop codon of the M2 domain, wherein the nucleic acid enables the expression of the sequences A and B into a single protein;

in inverse orientation.

8. The transfer retroviral vector according to claim 7 comprising successively:
   (i1) a modified 5' LTR comprising a CMV enhancer substituted for the U3 region,
   (i2) a psi and gag sequence,
   (i3) a central polypurine tract (cPPT)/DNA flap sequence,
   (i4) a Rev responsive element sequence (RRE),
   (i5) a Woodchuck hepatitis virus posttranscriptional regulatory element sequence (WPRE), and
   (i6) a self-inactivating 3' LTR comprising a deletion in the U3 region that renders the 5' LTR of the integrated provirus transcriptionally inactive,
wherein the multicistronic nucleic acid or nucleic acid (ii) is located in inverse orientation between the sequences (i4) and (i5).

9. A method for producing a conditional pseudotyped viral vector particle allowing physiologically-regulated expression of membrane-anchored and/or secreted antibody or chimera by B cells, comprising:
   a) transfecting a cell with
      (i) the transfer retroviral vector according to claim 7,
      (ii) a second nucleic acid comprising a cDNA encoding core proteins from the same retrovirus as the transfer retroviral vector (i), and
      (iii) a third nucleic acid comprising a cDNA encoding a viral envelope glycoprotein targeting B cells or CD34+ hematopoietic stem cells,
   to yield a producer cell;
   b) maintaining the producer cell in culture for sufficient time to allow expression of the cDNAs to produce the encoded viral proteins; and
   c) allowing the encoded viral proteins to form conditional pseudotyped viral vector particles.

10. A kit comprising:
   (i) the transfer retroviral vector according to claim 7,
   (ii) a second nucleic acid comprising a cDNA encoding core proteins from the same retrovirus as the retroviral vector (i), and
   (iii) a third nucleic acid comprising a cDNA encoding a viral envelope glycoprotein targeting B cells or CD34+ hematopoietic stem cells.

11. A conditional pseudotyped viral vector particle allowing physiologically-regulated expression of a membrane-anchored and/or secreted antibody or antigen-binding domain/effector protein chimera by B cells, wherein said conditional pseudotyped viral vector particle comprises:
   a multicistronic nucleic acid comprising:
   A) a sequence comprising successively:
      A1) a sequence encoding a light chain variable domain of an antibody of interest, fused in the frame with
      A2) a sequence encoding a constant region of the light chain of an immunoglobulin Ig; and
   B) a sequence comprising successively:
      B1) a sequence encoding a heavy chain variable domain of said antibody of interest, fused in the frame with
      B2) a sequence encoding constant regions of the heavy chain of an immunoglobulin Ig' in secretory form;
      B3) an intronic sequence of a gene of the heavy chain of said immunoglobulin Ig', said intronic sequence consisting of between 350 and 380 nucleotides and comprising an internal 5' splice site enabling the splicing of said intronic sequence B3) and a secretory-specific poly(A) (pAS) signal from the 3' terminal exon of said gene of the heavy chain;
      B4) a sequence, in frame with sequence B1), encoding transmembrane and cytoplasmic domains M1 and M2 of an immunoglobulin Ig' BCR, wherein said sequence B4) comprises, between the coding sequences of the M1 and M2 domains, an intronic sequence containing a splice site enabling the splicing of said intronic sequence between the M1 and M2 domains coding sequences, wherein said intronic sequence consists of between 200 and 250 nucleotides; and
      B5) a membrane-anchored specific poly(A) signal (pAM), after the stop codon of the M2 domain,
   wherein the multicistronic nucleic acid enables the co-expression of the sequences A and B into separate proteins and wherein said sequences A and B are linked by a linking sequence enabling the co-expression of the sequences A and B in a single m RNA; or
a multicistronic nucleic acid encoding an antigen-binding domain/effector protein chimera, the antigen-binding domain and/or the effector protein being respectively formed by two subunits, said nucleic acid comprising:
   A) a sequence comprising successively:
      A1) a sequence encoding a first subunit AbD1 of an antigen-binding domain AbD, fused in the frame with
      A2) a first subunit EfP1 of an effector protein EfP, or optionally a sequence encoding an effector protein EfP; and
   B) a sequence comprising successively:
      B1) a sequence encoding a second subunit AbD2 of the antigen-binding domain AbD, AbD2 forming in combination with AbD1 an antigen-binding domain specifically interacting with an antigen of interest, said sequence B1 being fused in the frame with
      B2) a sequence encoding a second subunit EfP2 of the effector protein EfP or a sequence encoding the effector protein EfP;
      B3) an intronic sequence of a gene of a heavy chain of an immunoglobulin Ig', said intronic sequence consisting of between 350 and 380 nucleotides and comprising an internal 5' splice site enabling the splicing of said intronic sequence B3) and a secretory-specific poly(A) (pAS) signal from the 3' terminal exon of said gene of the heavy chain;
      B4) a sequence, in frame with sequence B1), encoding transmembrane and cytoplasmic domains M1 and M2 of an immunoglobulin Ig' BCR, wherein said sequence B4) comprises, between the coding sequences of the M1 and M2 domains, an intronic sequence containing a splice site enabling the splicing of said intronic sequence between the M1 and M2 coding sequences, wherein said intronic sequence consists of between 200 and 250 nucleotides; and
      B5) a membrane-anchored specific poly(A) signal (pAM), after the stop codon of the M2 domain, wherein the multicistronic nucleic acid enables the co-expression of the sequences A and B into separate proteins and wherein said sequences A and B are linked by a linking sequence enabling the co-expression of the sequences A and B in a single mRNA; or
a nucleic acid encoding an antigen-binding domain/effector protein chimera, said nucleic acid comprising:
  A) a sequence encoding an antigen-binding domain AbD specifically interacting with an antigen of interest; and
  B) a sequence comprising successively:
    B2) a sequence encoding an effector protein EfP;
    B3) an intronic sequence of a gene of a heavy chain of an immunoglobulin Ig', said intronic sequence consisting of between 350 and 380 nucleotides and comprising an internal 5' splice site enabling the splicing of said intronic sequence B3) and a secretory-specific poly(A) (pAS) signal from the 3' terminal exon of said gene of the heavy chain;
    B4) a sequence, in frame with sequence B2), encoding transmembrane and cytoplasmic domains M1 and M2 of an immunoglobulin Ig' BCR, wherein said sequence B4) comprises, between the coding sequences of the M1 and M2 domains, an intronic sequence containing a splice site enabling the splicing of said intronic sequence between the M1 and M2 coding sequences, wherein said intronic sequence consists of between 200 and 250 nucleotides; and
    B5) a membrane-anchored specific poly(A) signal (pAM), after the stop codon of the M2 domain,
  wherein the nucleic acid enables the expression of the sequences A and B into a single protein;
and is pseudotyped with a viral envelope glycoprotein targeting B cells or CD34+ hematopoietic stem cells.

12. A stable virus packaging cell line producing the conditional pseudotyped viral vector particle according to claim 11.

13. A medicament comprising:
(i) a conditional pseudotyped viral vector particle according to claim 11,
(ii) a plasmid comprising
  a multicistronic nucleic acid comprising:
    A) a sequence comprising successively:
      A1) a sequence encoding a light chain variable domain of an antibody of interest, fused in the frame with
      A2) a sequence encoding a constant region of the light chain of an immunoglobulin Ig; and
    B) a sequence comprising successively:
      B1) a sequence encoding a heavy chain variable domain of said antibody of interest, fused in the frame with
      B2) a sequence encoding constant regions of the heavy chain of an immunoglobulin Ig' in secretory form;
      B3) an intronic sequence of a gene of the heavy chain of said immunoglobulin Ig', said intronic sequence consisting of between 350 and 380 nucleotides and comprising an internal 5' splice site enabling the splicing of said intronic sequence B3) and a secretory-specific poly(A) (pAS) signal from the 3' terminal exon of said gene of the heavy chain;
      B4) a sequence, in frame with sequence B1), encoding transmembrane and cytoplasmic domains M1 and M2 of an immunoglobulin Ig' BCR, wherein said sequence B4) comprises, between the coding sequences of the M1 and M2 domains, an intronic sequence containing a splice site enabling the splicing of said intronic sequence between the M1 and M2 domains coding sequences, wherein said intronic sequence consists of between 200 and 250 nucleotides; and
      B5) a membrane-anchored specific poly(A) signal (pAM), after the stop codon of the M2 domain,
    wherein the multicistronic nucleic acid enables the co-expression of the sequences A and B into separate proteins and wherein said sequences A and B are linked by a linking sequence enabling the co-expression of the sequences A and B in a single m RNA; or
  a multicistronic nucleic acid encoding an antigen-binding domain/effector protein chimera, the antigen-binding domain and/or the effector protein being respectively formed by two subunits, said nucleic acid comprising:
    A) a sequence comprising successively:
      A1) a sequence encoding a first subunit AbD1 of an antigen-binding domain AbD, fused in the frame with
      A2) a first subunit EfP1 of an effector protein EfP, or optionally a sequence encoding an effector protein EfP; and
    B) a sequence comprising successively:
      B1) a sequence encoding a second subunit AbD2 of the antigen-binding domain AbD, AbD2 forming in combination with AbD1 an antigen-binding domain specifically interacting with an antigen of interest, said sequence B1 being fused in the frame with
      B2) a sequence encoding a second subunit EfP2 of the effector protein EfP or a sequence encoding the effector protein EfP;
      B3) an intronic sequence of a gene of a heavy chain of an immunoglobulin Ig', said intronic sequence consisting of between 350 and 380 nucleotides and comprising an internal 5' splice site enabling the splicing of said intronic sequence B3) and a secretory-specific poly(A) (pAS) signal from the 3' terminal exon of said gene of the heavy chain;
      B4) a sequence, in frame with sequence B1), encoding transmembrane and cytoplasmic domains M1 and M2 of an immunoglobulin Ig' BCR, wherein said sequence B4) comprises, between the coding sequences of the M1 and M2 domains, an intronic sequence containing a splice site enabling the splicing of said intronic sequence between the M1 and M2 coding sequences, wherein said intronic sequence consists of between 200 and 250 nucleotides; and
      B5) a membrane-anchored specific poly(A) signal (pAM), after the stop codon of the M2 domain,
    wherein the multicistronic nucleic acid enables the co-expression of the sequences A and B into separate proteins and wherein said sequences A and B are linked by a linking sequence enabling the co-expression of the sequences A and B in a single mRNA; or
  a nucleic acid encoding an antigen-binding domain/effector protein chimera, said nucleic acid comprising:

A) a sequence encoding an antigen-binding domain AbD specifically interacting with an antigen of interest; and
B) a sequence comprising successively:
  B2) a sequence encoding an effector protein EfP;
  B3) an intronic sequence of a gene of a heavy chain of an immunoglobulin Ig', said intronic sequence consisting of between 350 and 380 nucleotides and comprising an internal 5' splice site enabling the splicing of said intronic sequence B3) and a secretory-specific poly(A) (pAS) signal from the 3' terminal exon of said gene of the heavy chain;
  B4) a sequence, in frame with sequence B2), encoding transmembrane and cytoplasmic domains M1 and M2 of an immunoglobulin Ig' BCR, wherein said sequence B4) comprises, between the coding sequences of the M1 and M2 domains, an intronic sequence containing a splice site enabling the splicing of said intronic sequence between the M1 and M2 coding sequences, wherein said intronic sequence consists of between 200 and 250 nucleotides; and
  B5) a membrane-anchored specific poly(A) signal (pAM), after the stop codon of the M2 domain,
  wherein the nucleic acid enables the expression of the sequences A and B into a single protein;
(iii) CD34+ hematopoietic stem cells and/or B cells transduced with the conditional pseudotyped viral vector particle defined at (i), or
(iv) CD34+ hematopoietic stem cells and/or B cells transfected with the plasmid defined at (ii),
as active ingredient
wherein the antibody or antigen-binding domain/effector protein chimera are able to treat and/or prevent an infectious disease, an inflammatory disease, or a cancer in a subject.

14. A vaccine composition comprising:
(a1) a conditional pseudotyped viral vector particle according to claim 11,
(a2) a plasmid comprising a multicistronic nucleic acid comprising:
  A1) a sequence encoding the light chain variable domain of an antibody of interest, fused in the frame with
  A2) a sequence encoding the constant region of the light chain of an immunoglobulin Ig; and
  B) a sequence comprising successively:
  B1) a sequence encoding the heavy chain variable domain of said antibody of interest, fused in the frame with
  B2) a sequence encoding the constant regions of the heavy chain of an immunoglobulin Ig' in secretory form;
  B3) an intronic sequence of the gene of the heavy chain of said immunoglobulin Ig', said intronic sequence consisting of between 350 and 380 nucleotides and comprising an internal 5' splice site enabling the splicing of said intronic sequence B3) and a secretory-specific poly(A) (pAS) signal from the 3' terminal exon of said gene;
  B4) a sequence, in frame with sequence B1), encoding the transmembrane and cytoplasmic domains M1 and M2 of the immunoglobulin Ig' BCR, wherein said sequence B4) comprises, between the coding sequences of the M1 and M2 domains, an intronic sequence containing a splice site enabling the splicing of said intronic sequence between the M1 and M2 domains coding sequences, wherein said intronic sequence consists of between 200 and 250 nucleotides; and
  B5) a membrane-anchored specific poly(A) signal (pAM), after the stop codon of the M2 domain,
  wherein the multicistronic nucleic acid enables the co-expression of the sequences A and B into separate proteins and wherein said sequences A and B are linked by a linking sequence enabling the co-expression of the sequences A and B in a single mRNA,
(a3) CD34+ hematopoietic stem cells and/or B cells transduced with the conditional pseudotyped viral vector particle defined at (a1), or
(a4) CD34+ hematopoietic stem cells and/or B cells transfected with the plasmid defined at (a2),
and (b) a pharmaceutically acceptable carrier.

15. A method for inducing the physiologically-regulated expression of a membrane-anchored and/or secreted antibody of interest by a B cell ex vivo, comprising exposing the B cell to the conditional pseudotyped viral vector particle according to claim 11.

16. A method for treating disease in a subject comprising administering a therapeutically effective amount of:
(i) a conditional pseudotyped viral vector particle according to claim 11,
(ii) a plasmid comprising
a multicistronic nucleic acid comprising:
A) a sequence comprising successively:
  A1) a sequence encoding a light chain variable domain of an antibody of interest, fused in the frame with
  A2) a sequence encoding a constant region of the light chain of an immunoglobulin Ig; and
B) a sequence comprising successively:
  B1) a sequence encoding a heavy chain variable domain of said antibody of interest, fused in the frame with
  B2) a sequence encoding constant regions of the heavy chain of an immunoglobulin Ig' in secretory form;
  B3) an intronic sequence of a gene of the heavy chain of said immunoglobulin Ig', said intronic sequence consisting of between 350 and 380 nucleotides and comprising an internal 5' splice site enabling the splicing of said intronic sequence B3) and a secretory-specific poly(A) (pAS) signal from the 3' terminal exon of said gene of the heavy chain;
  B4) a sequence, in frame with sequence B1), encoding transmembrane and cytoplasmic domains M1 and M2 of an immunoglobulin Ig' BCR, wherein said sequence B4) comprises, between the coding sequences of the M1 and M2 domains, an intronic sequence containing a splice site enabling the splicing of said intronic sequence between the M1 and M2 domains coding sequences, wherein said intronic sequence consists of between 200 and 250 nucleotides; and
  B5) a membrane-anchored specific poly(A) signal (pAM), after the stop codon of the M2 domain,
wherein the multicistronic nucleic acid enables the co-expression of the sequences A and B into separate proteins and wherein said sequences A and B are linked by a linking sequence enabling the co-expression of the sequences A and B in a single m RNA; or
a multicistronic nucleic acid encoding an antigen-binding domain/effector protein chimera, the antigen-binding domain and/or the effector protein being respectively formed by two subunits, said nucleic acid comprising:

A) a sequence comprising successively:
   A1) a sequence encoding a first subunit AbD1 of an antigen-binding domain AbD, fused in the frame with
   A2) a first subunit EfP1 of an effector protein EfP, or optionally a sequence encoding an effector protein EfP; and
B) a sequence comprising successively:
   B1) a sequence encoding a second subunit AbD2 of the antigen-binding domain AbD, AbD2 forming in combination with AbD1 an antigen-binding domain specifically interacting with an antigen of interest, said sequence B1 being fused in the frame with
   B2) a sequence encoding a second subunit EfP2 of the effector protein EfP or a sequence encoding the effector protein EfP;
   B3) an intronic sequence of a gene of a heavy chain of an immunoglobulin Ig', said intronic sequence consisting of between 350 and 380 nucleotides and comprising an internal 5' splice site enabling the splicing of said intronic sequence B3) and a secretory-specific poly(A) (pAS) signal from the 3' terminal exon of said gene of the heavy chain;
   B4) a sequence, in frame with sequence B1), encoding transmembrane and cytoplasmic domains M1 and M2 of an immunoglobulin Ig' BCR, wherein said sequence B4) comprises, between the coding sequences of the M1 and M2 domains, an intronic sequence containing a splice site enabling the splicing of said intronic sequence between the M1 and M2 coding sequences, wherein said intronic sequence consists of between 200 and 250 nucleotides; and
   B5) a membrane-anchored specific poly(A) signal (pAM), after the stop codon of the M2 domain,
wherein the multicistronic nucleic acid enables the co-expression of the sequences A and B into separate proteins and wherein said sequences A and B are linked by a linking sequence enabling the co-expression of the sequences A and B in a single mRNA; or
a nucleic acid encoding an antigen-binding domain/effector protein chimera, said nucleic acid comprising:
A) a sequence encoding an antigen-binding domain AbD specifically interacting with an antigen of interest; and
B) a sequence comprising successively:
   B2) a sequence encoding an effector protein EfP;
   B3) an intronic sequence of a gene of a heavy chain of an immunoglobulin Ig', said intronic sequence consisting of between 350 and 380 nucleotides and comprising an internal 5' splice site enabling the splicing of said intronic sequence B3) and a secretory-specific poly(A) (pAS) signal from the 3' terminal exon of said gene of the heavy chain;
   B4) a sequence, in frame with sequence B2), encoding transmembrane and cytoplasmic domains M1 and M2 of an immunoglobulin Ig' BCR, wherein said sequence B4) comprises, between the coding sequences of the M1 and M2 domains, an intronic sequence containing a splice site enabling the splicing of said intronic sequence between the M1 and M2 coding sequences, wherein said intronic sequence consists of between 200 and 250 nucleotides; and
   B5) a membrane-anchored specific poly(A) signal (pAM), after the stop codon of the M2 domain,
wherein the nucleic acid enables the expression of the sequences A and B into a single protein;
(iii) CD34+ hematopoietic stem cells and/or B cells transduced with the conditional pseudotyped viral vector particle defined at (i), or
(iv) CD34+ hematopoietic stem cells and/or B cells transfected with the plasmid defined at (ii),
to a subject in need thereof,
wherein the antibody or antigen-binding domain/effector protein chimera are able to treat the disease in the subject.

17. A method of vaccination of a subject comprising administering in a subject in need thereof a prophylactically effective amount of:
(i) the conditional pseudotyped viral vector particle according to claim 11,
(ii) a plasmid comprising a multicistronic nucleic acid comprising:
A) a sequence comprising successively:
   A1) a sequence encoding a light chain variable domain of an antibody of interest, fused in the frame with
   A2) a sequence encoding a constant region of the light chain of an immunoglobulin Ig; and
B) a sequence comprising successively:
   B1) a sequence encoding a heavy chain variable domain of said antibody of interest, fused in the frame with
   B2) a sequence encoding constant regions of the heavy chain of an immunoglobulin Ig' in secretory form;
   B3) an intronic sequence of a gene of the heavy chain of said immunoglobulin Ig', said intronic sequence consisting of between 350 and 380 nucleotides and comprising an internal 5' splice site enabling the splicing of said intronic sequence B3) and a secretory-specific poly(A) (pAS) signal from the 3' terminal exon of said gene of the heavy chain;
   B4) a sequence, in frame with sequence B1), encoding transmembrane and cytoplasmic domains M1 and M2 of an immunoglobulin Ig' BCR, wherein said sequence B4) comprises, between the coding sequences of the M1 and M2 domains, an intronic sequence containing a splice site enabling the splicing of said intronic sequence between the M1 and M2 domains coding sequences, wherein said intronic sequence consists of between 200 and 250 nucleotides; and
   B5) a membrane-anchored specific poly(A) signal (pAM), after the stop codon of the M2 domain,
wherein the multicistronic nucleic acid enables the co-expression of the sequences A and B into separate proteins and wherein said sequences A and B are linked by a linking sequence enabling the co-expression of the sequences A and B in a single m RNA;
(iii) CD34+ hematopoietic stem cells and/or B cells transduced with the conditional pseudotyped viral vector defined at (i), or
(iv) CD34+ hematopoietic stem cells and/or B cells transfected with the plasmid defined at (ii),
wherein the antibody or antigen-binding domain/effector protein chimera are able to prevent an infectious disease, an inflammatory disease, or a cancer in a subject.

18. A method of providing vectored immunoprophylaxis to a subject, comprising administering to said subject a therapeutically effective amount of
(i) the conditional pseudotyped viral vector particle according to claim 11,
(ii) a plasmid comprising a multicistronic nucleic acid comprising:
A) a sequence comprising successively:
A1) a sequence encoding a light chain variable domain of an antibody of interest, fused in the frame with
A2) a sequence encoding a constant region of the light chain of an immunoglobulin Ig; and
B) a sequence comprising successively:
B1) a sequence encoding a heavy chain variable domain of said antibody of interest, fused in the frame with
B2) a sequence encoding constant regions of the heavy chain of an immunoglobulin Ig' in secretory form;
B3) an intronic sequence of a gene of the heavy chain of said immunoglobulin Ig', said intronic sequence consisting of between 350 and 380 nucleotides and comprising an internal 5' splice site enabling the splicing of said intronic sequence B3) and a secretory-specific poly(A) (pAS) signal from the 3' terminal exon of said gene of the heavy chain;
B4) a sequence, in frame with sequence B1), encoding transmembrane and cytoplasmic domains M1 and M2 of an immunoglobulin Ig' BCR, wherein said sequence B4) comprises, between the coding sequences of the M1 and M2 domains, an intronic sequence containing a splice site enabling the splicing of said intronic sequence between the M1 and M2 domains coding sequences, wherein said intronic sequence consists of between 200 and 250 nucleotides; and
B5) a membrane-anchored specific poly(A) signal (pAM), after the stop codon of the M2 domain,
wherein the multicistronic nucleic acid enables the co-expression of the sequences A and B into separate proteins and wherein said sequences A and B are linked by a linking sequence enabling the co-expression of the sequences A and B in a single m RNA;
(iii) CD34+ hematopoietic stem cells and/or B cells transduced with the conditional pseudotyped viral vector particle defined at (i), or
(iv) CD34+ hematopoietic stem cells and/or B cells transfected with the plasmid defined at (ii),
wherein the antibody or antigen-binding domain/effector protein chimera are able to treat and/or prevent an infectious disease, an inflammatory disease, or a cancer in a subject.

19. A method for treating and/or preventing an infectious disease, an inflammatory disease or a cancer in a subject, comprising administering a prophylactically or therapeutically effective amount of:
(i) the conditional pseudotyped viral vector particle according to claim 11,
(ii) a plasmid comprising
a multicistronic nucleic acid comprising:
A) a sequence comprising successively:
A1) a sequence encoding a light chain variable domain of an antibody of interest, fused in the frame with
A2) a sequence encoding a constant region of the light chain of an immunoglobulin Ig; and
B) a sequence comprising successively:
B1) a sequence encoding a heavy chain variable domain of said antibody of interest, fused in the frame with
B2) a sequence encoding constant regions of the heavy chain of an immunoglobulin Ig' in secretory form;
B3) an intronic sequence of a gene of the heavy chain of said immunoglobulin Ig', said intronic sequence consisting of between 350 and 380 nucleotides and comprising an internal 5' splice site enabling the splicing of said intronic sequence B3) and a secretory-specific poly(A) (pAS) signal from the 3' terminal exon of said gene of the heavy chain;
B4) a sequence, in frame with sequence B1), encoding transmembrane and cytoplasmic domains M1 and M2 of an immunoglobulin Ig' BCR, wherein said sequence B4) comprises, between the coding sequences of the M1 and M2 domains, an intronic sequence containing a splice site enabling the splicing of said intronic sequence between the M1 and M2 domains coding sequences, wherein said intronic sequence consists of between 200 and 250 nucleotides; and
B5) a membrane-anchored specific poly(A) signal (pAM), after the stop codon of the M2 domain,
wherein the multicistronic nucleic acid enables the co-expression of the sequences A and B into separate proteins and wherein said sequences A and B are linked by a linking sequence enabling the co-expression of the sequences A and B in a single m RNA; or
a multicistronic nucleic acid encoding an antigen-binding domain/effector protein chimera, the antigen-binding domain and/or the effector protein being respectively formed by two subunits, said nucleic acid comprising:
A) a sequence comprising successively:
A1) a sequence encoding a first subunit AbD1 of an antigen-binding domain AbD, fused in the frame with
A2) a first subunit EfP1 of an effector protein EfP, or optionally a sequence encoding an effector protein EfP; and
B) a sequence comprising successively:
B1) a sequence encoding a second subunit AbD2 of the antigen-binding domain AbD, AbD2 forming in combination with AbD1 an antigen-binding domain specifically interacting with an antigen of interest, said sequence B1 being fused in the frame with
B2) a sequence encoding a second subunit EfP2 of the effector protein EfP or a sequence encoding the effector protein EfP;
B3) an intronic sequence of a gene of a heavy chain of an immunoglobulin Ig', said intronic sequence consisting of between 350 and 380 nucleotides and comprising an internal 5' splice site enabling the splicing of said intronic sequence B3) and a secretory-specific poly(A) (pAS) signal from the 3' terminal exon of said gene of the heavy chain;
B4) a sequence, in frame with sequence B1), encoding transmembrane and cytoplasmic domains M1 and M2 of an immunoglobulin Ig'

BCR, wherein said sequence B4) comprises, between the coding sequences of the M1 and M2 domains, an intronic sequence containing a splice site enabling the splicing of said intronic sequence between the M1 and M2 coding sequences, wherein said intronic sequence consists of between 200 and 250 nucleotides; and B5) a membrane-anchored specific poly(A) signal (pAM), after the stop codon of the M2 domain, wherein the multicistronic nucleic acid enables the co-expression of the sequences A and B into separate proteins and wherein said sequences A and B are linked by a linking sequence enabling the co-expression of the sequences A and B in a single mRNA; or a nucleic acid encoding an antigen-binding domain/effector protein chimera, said nucleic acid comprising:

A) a sequence encoding an antigen-binding domain AbD specifically interacting with an antigen of interest; and B) a sequence comprising successively:
B2) a sequence encoding an effector protein EfP;
B3) an intronic sequence of a gene of a heavy chain of an immunoglobulin Ig', said intronic sequence consisting of between 350 and 380 nucleotides and comprising an internal 5' splice site enabling the splicing of said intronic sequence B3) and a secretory-specific poly(A) (pAS) signal from the 3' terminal exon of said gene of the heavy chain;

B4) a sequence, in frame with sequence B2), encoding transmembrane and cytoplasmic domains M1 and M2 of an immunoglobulin Ig' BCR, wherein said sequence B4) comprises, between the coding sequences of the M1 and M2 domains, an intronic sequence containing a splice site enabling the splicing of said intronic sequence between the M1 and M2 coding sequences, wherein said intronic sequence consists of between 200 and 250 nucleotides; and B5) a membrane-anchored specific poly(A) signal (pAM), after the stop codon of the M2 domain, wherein the nucleic acid enables the expression of the sequences A and B into a single protein;

(iii) CD34+ hematopoietic stem cells and/or B cells transduced with the conditional pseudotyped viral vector particle defined at (i), or (iv) CD34+ hematopoietic stem cells and/or B cells transfected with the plasmid defined at (ii), in a subject in need thereof, wherein the antibody or antigen-binding domain/effector protein chimera are able to treat and/or prevent the infectious disease, the inflammatory disease, or the cancer in the subject.

* * * * *